United States Patent
Sonderegger et al.

(10) Patent No.: US 10,758,721 B2
(45) Date of Patent: Sep. 1, 2020

(54) INFUSION DEVICE WITH RELEASABLE FLUID CONNECTOR

(71) Applicant: Becton, Dickinson and Company, Franklin Lakes, NJ (US)

(72) Inventors: Ralph Sonderegger, Farmington, UT (US); Ronald Marsh, Hackettstown, NJ (US); Charles Hwang, Wellesley, MA (US); Stephen Richards, Carrywood, ID (US); Victor Politis, Natick, MA (US); Joshua Horvath, San Ramon, CA (US); Benjamin Glace, Dunbarton, NH (US); James Sullivan, Shrewsbury, MA (US); Ryan Lambert, San Francisco, CA (US); Gregory Venditto, Goshen, NY (US); Eric Bené, Lynn, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 229 days.

(21) Appl. No.: 15/714,861

(22) Filed: Sep. 25, 2017

(65) Prior Publication Data

US 2018/0008815 A1     Jan. 11, 2018

Related U.S. Application Data

(63) Continuation of application No. 14/362,104, filed as application No. PCT/US2012/068632 on Dec. 7, 2012, now Pat. No. 9,795,777.

(Continued)

(51) Int. Cl.
*A61M 39/10*     (2006.01)
*A61M 5/158*     (2006.01)
(Continued)

(52) U.S. Cl.
CPC ........ *A61M 39/1055* (2013.01); *A61M 5/158* (2013.01); *A61M 5/3202* (2013.01);
(Continued)

(58) Field of Classification Search
CPC .. A61M 2005/1581; A61M 2005/1585; A61M 2005/1586; A61M 2005/1587;
(Continued)

(56) References Cited

U.S. PATENT DOCUMENTS 2,748,769 A    6/1956   Huber
2,928,633 A    6/1957   Holmes et al.
(Continued)

FOREIGN PATENT DOCUMENTS

EP        2598188 A1    1/1982
EP        0795280 A2    9/1997
(Continued)

OTHER PUBLICATIONS

Introducing the i-port Advance—The i-port with an inserter, http://www.i-port.com/i-port-advance.html (last visited Oct. 10, 2013).

*Primary Examiner* — Quynh-Nhu H. Vu
(74) *Attorney, Agent, or Firm* — Dickinson Wright PLLC

(57) ABSTRACT

An infusion set system includes a base and a fluid connector removably coupleable thereto. The fluid connector includes a fluid path portion and at least one connector latch displaceably connected to the fluid path portion and displaceable to a latching position in which at least a portion of the connector latch extends into the fluid path portion, which includes a cannula extending from a top interior surface thereof, and a plurality of internal sidewalls corresponding to at least two of a plurality of flat side surfaces of at least one of a base section and a base latch, thereby facilitating connection between the base and the fluid connector in a plurality of discrete rotational connecting positions. When (Continued)

the fluid connector is locked to the base, the at least one connector latch engages a base latching portion of the base and restricts proximal displacement of the fluid connector.

13 Claims, 47 Drawing Sheets

Related U.S. Application Data

(60) Provisional application No. 61/719,755, filed on Oct. 29, 2012, provisional application No. 61/692,985, filed on Aug. 24, 2012, provisional application No. 61/568,074, filed on Dec. 7, 2011.

(51) Int. Cl.
| | |
|---|---|
| A61M 5/32 | (2006.01) |
| A61M 39/04 | (2006.01) |
| A61M 25/06 | (2006.01) |
| A61M 39/00 | (2006.01) |
| A61M 5/142 | (2006.01) |

(52) U.S. Cl.
CPC ........ *A61M 5/3213* (2013.01); *A61M 5/14248* (2013.01); *A61M 25/0606* (2013.01); *A61M 39/045* (2013.01); *A61M 2005/1581* (2013.01); *A61M 2005/1585* (2013.01); *A61M 2005/1586* (2013.01); *A61M 2005/1587* (2013.01); *A61M 2039/0036* (2013.01); *A61M 2039/0072* (2013.01); *A61M 2207/00* (2013.01)

(58) Field of Classification Search
CPC .. A61M 2039/0036; A61M 2039/0072; A61M 2207/00; A61M 25/0606; A61M 39/045; A61M 39/1055; A61M 5/14248; A61M 5/158; A61M 5/3202; A61M 5/3213
See application file for complete search history.

(56) References Cited

U.S. PATENT DOCUMENTS

| | | | |
|---|---|---|---|
| 3,658,061 A | | 4/1972 | Hall |
| 3,782,671 A | | 1/1974 | Igwe |
| 4,123,091 A | | 10/1978 | Cosentino et al. |
| 4,219,912 A | | 9/1980 | Adams |
| 4,311,137 A | | 1/1982 | Gerard |
| 4,362,156 A | | 12/1982 | Feller, Jr. et al. |
| D269,571 S | | 7/1983 | Geshwind |
| 4,752,292 A | | 6/1988 | Lopez et al. |
| 4,755,173 A | * | 7/1988 | Konopka .......... A61M 25/0606 128/DIG. 26 |
| 4,781,680 A | | 11/1988 | Redmond et al. |
| 4,834,718 A | | 5/1989 | McDonald |
| 4,894,055 A | | 1/1990 | Sudnak |
| 4,938,514 A | | 7/1990 | D'Addezio |
| 4,982,842 A | | 1/1991 | Hollister |
| 5,017,189 A | | 5/1991 | Boumendil |
| 5,137,529 A | | 8/1992 | Watson et al. |
| 5,151,089 A | | 9/1992 | Kirk, III et al. |
| 5,257,980 A | | 11/1993 | Van Antwerp et al. |
| 5,273,545 A | | 12/1993 | Hunt et al. |
| 5,300,034 A | | 4/1994 | Behnke et al. |
| 5,312,363 A | | 5/1994 | Ryan et al. |
| 5,350,363 A | | 9/1994 | Goode et al. |
| 5,360,408 A | | 11/1994 | Vaillancourt |
| 5,368,801 A | | 11/1994 | Vaillancourt |
| 5,472,138 A | | 12/1995 | Ingram |
| 5,490,841 A | | 2/1996 | Landis |
| 5,522,803 A | | 6/1996 | Teissen-Simony |
| 5,538,505 A | | 7/1996 | Weinstein et al. |
| 5,545,143 A | | 8/1996 | Fischell |
| 5,562,631 A | | 10/1996 | Bogert |
| 5,575,769 A | | 11/1996 | Vaillancourt |
| 5,591,138 A | | 1/1997 | Vailancourt |
| 5,613,956 A | | 3/1997 | Patterson et al. |
| 5,688,254 A | | 11/1997 | Lopez et al. |
| 5,725,503 A | | 3/1998 | Arnett |
| 5,776,116 A | | 7/1998 | Lopez et al. |
| 5,797,897 A | | 8/1998 | Jepson et al. |
| 5,810,792 A | | 9/1998 | Fangrow et al. |
| 5,817,074 A | | 10/1998 | Racz |
| 5,848,990 A | | 12/1998 | Cirelli et al. |
| 5,851,197 A | | 12/1998 | Marano et al. |
| 5,871,500 A | | 2/1999 | Jepson et al. |
| 5,891,099 A | | 4/1999 | Nakajima et al. |
| 5,935,109 A | | 8/1999 | Donnan |
| 5,968,011 A | | 10/1999 | Larsen et al. |
| 6,017,328 A | | 1/2000 | Fischell et al. |
| 6,056,718 A | | 5/2000 | Funderburk et al. |
| 6,093,172 A | | 7/2000 | Funderburk et al. |
| 6,126,637 A | | 10/2000 | Kriesel et al. |
| 6,162,206 A | | 12/2000 | Bindokas et al. |
| 6,261,272 B1 | | 7/2001 | Gross et al. |
| 6,273,869 B1 | | 8/2001 | Vaillancourt |
| 6,293,925 B1 | | 9/2001 | Safabash et al. |
| 6,302,866 B1 | | 10/2001 | Marggi |
| 6,346,095 B1 | | 2/2002 | Gross et al. |
| 6,355,021 B1 | | 3/2002 | Nielsen et al. |
| D461,891 S | | 8/2002 | Moberg |
| 6,447,498 B1 | | 9/2002 | Jepson et al. |
| 6,485,473 B1 | | 11/2002 | Lynn |
| 6,520,938 B1 | | 2/2003 | Funderburk et al. |
| 6,605,076 B1 | | 8/2003 | Jepson et al. |
| 6,607,509 B2 | | 8/2003 | Bobroff et al. |
| 6,685,674 B2 | | 2/2004 | Douglas et al. |
| 6,689,100 B2 | | 2/2004 | Connelly et al. |
| 6,702,779 B2 | | 3/2004 | Connelly et al. |
| D488,230 S | | 4/2004 | Ignotz et al. |
| 6,736,797 B1 | | 5/2004 | Larsen et al. |
| 6,740,063 B2 | | 5/2004 | Lynn |
| 6,830,562 B2 | | 12/2004 | Mogensen et al. |
| 6,840,922 B2 | | 1/2005 | Nielsen et al. |
| 6,926,694 B2 | | 8/2005 | Marano-Ford et al. |
| 6,949,084 B2 | | 9/2005 | Marggi et al. |
| 6,972,002 B2 | | 12/2005 | Thorne |
| 6,991,620 B2 | | 1/2006 | Marano-Ford et al. |
| 6,997,907 B2 | | 2/2006 | Safabash et al. |
| 7,022,108 B2 | | 4/2006 | Marano-Ford et al. |
| 7,070,580 B2 | | 7/2006 | Nielsen |
| D526,409 S | | 8/2006 | Nielsen et al. |
| 7,128,730 B2 | | 10/2006 | Marano-Ford et al. |
| 7,129,389 B1 | | 10/2006 | Watson |
| D532,436 S | | 11/2006 | Kruse et al. |
| 7,147,623 B2 | | 12/2006 | Mathiasen |
| 7,207,974 B2 | | 4/2007 | Safabash et al. |
| 7,297,138 B2 | | 11/2007 | Fangrow et al. |
| 7,300,419 B2 | | 11/2007 | Fangrow et al. |
| 7,303,544 B2 | | 12/2007 | Buetikofer et al. |
| 7,309,326 B2 | | 12/2007 | Fangrow |
| 7,311,694 B2 | | 12/2007 | Fangrow |
| 7,314,463 B2 | | 1/2008 | Fangrow |
| 7,331,939 B2 | | 2/2008 | Fangrow |
| 7,338,465 B2 | | 3/2008 | Patton |
| 7,377,908 B2 | | 5/2008 | Buetikofer et al. |
| 7,407,491 B2 | | 8/2008 | Fangrow |
| 7,407,493 B2 | | 8/2008 | Cane |
| D576,267 S | | 9/2008 | Mogensen et al. |
| 7,481,794 B2 | | 1/2009 | Jensen |
| 7,494,481 B2 | | 2/2009 | Moberg et al. |
| 7,520,867 B2 | | 4/2009 | Bowman et al. |
| 7,524,300 B2 | | 4/2009 | Patton |
| 7,594,902 B2 | | 9/2009 | Horisberger et al. |
| 7,621,395 B2 | | 11/2009 | Mogensen et al. |
| 7,682,341 B2 | | 3/2010 | Nakajima |
| 7,699,807 B2 | | 4/2010 | Faust et al. |
| 7,699,808 B2 | | 4/2010 | Marrs et al. |
| 7,704,228 B2 | | 4/2010 | Patton |
| 7,727,198 B2 | | 6/2010 | Nakajima |
| 7,731,691 B2 | | 6/2010 | Cote et al. |
| 7,744,568 B2 | | 6/2010 | Douglas et al. |
| 7,744,570 B2 | | 6/2010 | Fangrow |
| D620,491 S | | 7/2010 | Wu |

(56) References Cited

U.S. PATENT DOCUMENTS

| | | |
|---|---|---|
| 7,731,680 B2 | 7/2010 | Patton |
| 7,771,412 B2 | 8/2010 | Anderson et al. |
| 7,850,658 B2 | 12/2010 | Faust et al. |
| 7,879,010 B2 | 2/2011 | Hunn et al. |
| 7,892,216 B2 | 2/2011 | Fangrow |
| 7,931,615 B2 | 4/2011 | Fangrow |
| 7,935,090 B2 | 5/2011 | Patton |
| 7,985,199 B2 | 7/2011 | Kornerup et al. |
| 7,993,306 B2 | 8/2011 | Marrs et al. |
| 8,012,126 B2 | 9/2011 | Tipsmark et al. |
| 8,105,279 B2 | 1/2012 | Mernoe et al. |
| 8,152,769 B2 | 4/2012 | Douglas et al. |
| 8,152,771 B2 | 4/2012 | Mogensen et al. |
| 8,162,892 B2 | 4/2012 | Mogensen et al. |
| D659,177 S | 5/2012 | Chan |
| 8,172,805 B2 | 5/2012 | Mogensen et al. |
| 8,177,745 B2 | 5/2012 | Brechbuehler et al. |
| 8,216,208 B2 | 7/2012 | Patton |
| 8,221,361 B2 | 7/2012 | Patton |
| 8,221,362 B2 | 7/2012 | Patton |
| 8,221,386 B2 | 7/2012 | Patton |
| 8,226,614 B2 | 7/2012 | Turner et al. |
| 8,231,577 B2 | 7/2012 | Carter et al. |
| 8,262,627 B2 | 9/2012 | Patton |
| 8,317,759 B2 | 11/2012 | Moberg et al. |
| 8,366,683 B2 | 2/2013 | Patton |
| 8,449,504 B2 | 5/2013 | Carter et al. |
| D684,685 S | 6/2013 | Schneider et al. |
| D685,083 S | 6/2013 | Schneider et al. |
| 8,469,929 B2 | 6/2013 | Hunn et al. |
| 8,551,047 B2 | 10/2013 | Burns et al. |
| 8,628,498 B2 * | 1/2014 | Safabash ............... A61M 5/158 604/164.01 |
| 8,657,788 B2 | 2/2014 | Fangrow |
| 8,771,227 B2 | 7/2014 | Connelly et al. |
| 8,777,925 B2 | 7/2014 | Patton |
| 8,790,311 B2 * | 7/2014 | Gyrn ................... A61M 5/158 604/180 |
| 8,795,309 B2 | 8/2014 | Lacy |
| 8,801,660 B2 | 8/2014 | Nunn et al. |
| 8,808,254 B2 | 8/2014 | Lynn |
| 8,814,833 B2 | 8/2014 | Farrell et al. |
| 8,827,957 B2 | 9/2014 | Searle et al. |
| 8,905,974 B2 | 12/2014 | Carter et al. |
| 8,945,057 B2 | 2/2015 | Gyrn et al. |
| 8,956,330 B2 | 2/2015 | Fangrow, Jr. |
| 2002/0173774 A1 | 11/2002 | Olsen |
| 2003/0018303 A1 | 1/2003 | Sharp |
| 2003/0105431 A1 | 6/2003 | Howell |
| 2003/0220610 A1 | 11/2003 | Lastovich et al. |
| 2004/0092893 A1 | 5/2004 | Haider et al. |
| 2004/0102740 A1 | 5/2004 | Meloul |
| 2004/0158207 A1 | 8/2004 | Hunn et al. |
| 2004/0199123 A1 * | 10/2004 | Nielsen .................. A61M 5/14 604/180 |
| 2005/0038378 A1 | 2/2005 | Lastovich et al. |
| 2005/0090784 A1 | 4/2005 | Nielsen et al. |
| 2005/0101932 A1 | 5/2005 | Cote et al. |
| 2005/0245895 A1 | 11/2005 | Haider et al. |
| 2005/0267487 A1 | 12/2005 | Christensen et al. |
| 2006/0129090 A1 * | 6/2006 | Moberg ................. A61M 5/158 604/93.01 |
| 2007/0049874 A1 | 3/2007 | Patton |
| 2007/0088271 A1 | 4/2007 | Richards |
| 2007/0191771 A1 | 8/2007 | Moyer |
| 2007/0191772 A1 | 8/2007 | Wojcik |
| 2007/0191774 A1 | 8/2007 | Carrez et al. |
| 2007/0244448 A1 | 10/2007 | Lastovich et al. |
| 2007/0276355 A1 | 11/2007 | Nielsen et al. |
| 2008/0173783 A1 | 7/2008 | Bunker |
| 2008/0243051 A1 | 10/2008 | DeStefano |
| 2008/0249471 A1 | 10/2008 | DeStefano et al. |
| 2008/0277874 A1 | 11/2008 | Scoccia |
| 2008/0281297 A1 | 11/2008 | Pesach et al. |
| 2008/0287874 A1 | 11/2008 | Elmouelhi |
| 2008/0302204 A1 | 12/2008 | Lee |
| 2009/0069752 A1 | 3/2009 | Raj et al. |
| 2009/0076453 A1 | 3/2009 | Mejqqhede et al. |
| 2009/0082734 A1 | 3/2009 | Walters et al. |
| 2009/0143741 A1 | 6/2009 | Burn |
| 2009/0143763 A1 | 6/2009 | Wyss et al. |
| 2009/0264825 A1 | 10/2009 | Cote et al. |
| 2009/0299289 A1 | 12/2009 | Kamen et al. |
| 2010/0179508 A1 | 7/2010 | Mogensen et al. |
| 2010/0191189 A1 | 7/2010 | Harding et al. |
| 2011/0060287 A1 * | 3/2011 | Ambruzs ............... A61M 5/158 604/164.12 |
| 2011/0130722 A1 | 6/2011 | Fangrow |
| 2011/0213340 A1 | 9/2011 | Howell et al. |
| 2011/0288482 A1 | 11/2011 | Farrell et al. |
| 2011/0295209 A1 | 12/2011 | Fangrow et al. |
| 2011/0313357 A1 | 12/2011 | Skutnik et al. |
| 2012/0123344 A1 | 5/2012 | Hornig et al. |
| 2012/0179106 A1 | 7/2012 | Cote et al. |
| 2012/0226242 A1 | 9/2012 | Nielsen et al. |
| 2013/0006216 A1 | 1/2013 | Taylor et al. |
| 2013/0012881 A1 | 1/2013 | Lacy |
| 2013/0023834 A1 | 1/2013 | Turner et al. |
| 2013/0245555 A1 | 9/2013 | Dirac et al. |
| 2013/0281974 A1 | 10/2013 | Karmen et al. |
| 2013/0282974 A1 | 10/2013 | Joisha |
| 2014/0039453 A1 | 2/2014 | Sonderegger |
| 2014/0039458 A1 | 2/2014 | Constantineau et al. |
| 2014/0058353 A1 | 2/2014 | Politis et al. |
| 2014/0074033 A1 | 3/2014 | Sonderegger et al. |
| 2014/0074037 A1 | 3/2014 | Bornhoft |
| 2014/0088509 A1 | 3/2014 | Sonderegger et al. |
| 2014/0088549 A1 | 3/2014 | Cole et al. |
| 2014/0088550 A1 | 3/2014 | Bene et al. |
| 2014/0100544 A1 | 4/2014 | Hwang |
| 2014/0135696 A1 | 5/2014 | Ruan et al. |
| 2014/0276416 A1 | 9/2014 | Nelson et al. |
| 2014/0276576 A1 | 9/2014 | Cole et al. |
| 2014/0316379 A1 | 10/2014 | Sonderegger et al. |
| 2014/0371715 A1 | 12/2014 | Farrell et al. |
| 2015/0045745 A1 | 2/2015 | Patton |

FOREIGN PATENT DOCUMENTS

| | | |
|---|---|---|
| EP | 1704889 A1 | 9/2006 |
| EP | 1949926 A1 | 7/2008 |
| JP | 54-77494 U | 6/1979 |
| JP | 62-281966 A | 12/1987 |
| JP | 63-38535 U | 3/1988 |
| JP | 02-029269 A | 1/1990 |
| JP | 2007-510497 A | 4/2007 |
| JP | 2010-507457 A | 3/2010 |
| JP | 2011-520507 A | 7/2011 |
| WO | WO-9109637 A1 | 7/1991 |
| WO | WO-03026728 A1 | 4/2003 |
| WO | WO-2006062680 A1 | 6/2006 |
| WO | WO-2006085176 A1 | 8/2006 |
| WO | WO-2006097111 A3 | 9/2006 |
| WO | WO-2006116613 A1 | 11/2006 |
| WO | WO-2007056309 A2 | 5/2007 |
| WO | WO-2008014792 A1 | 2/2008 |
| WO | WO-2008092958 A2 | 8/2008 |
| WO | WO-2009139857 A1 | 11/2009 |
| WO | WO-2010/122988 A1 | 10/2010 |
| WO | WO-2010112521 A1 | 10/2010 |
| WO | WO-2010142641 A1 | 12/2010 |

* cited by examiner

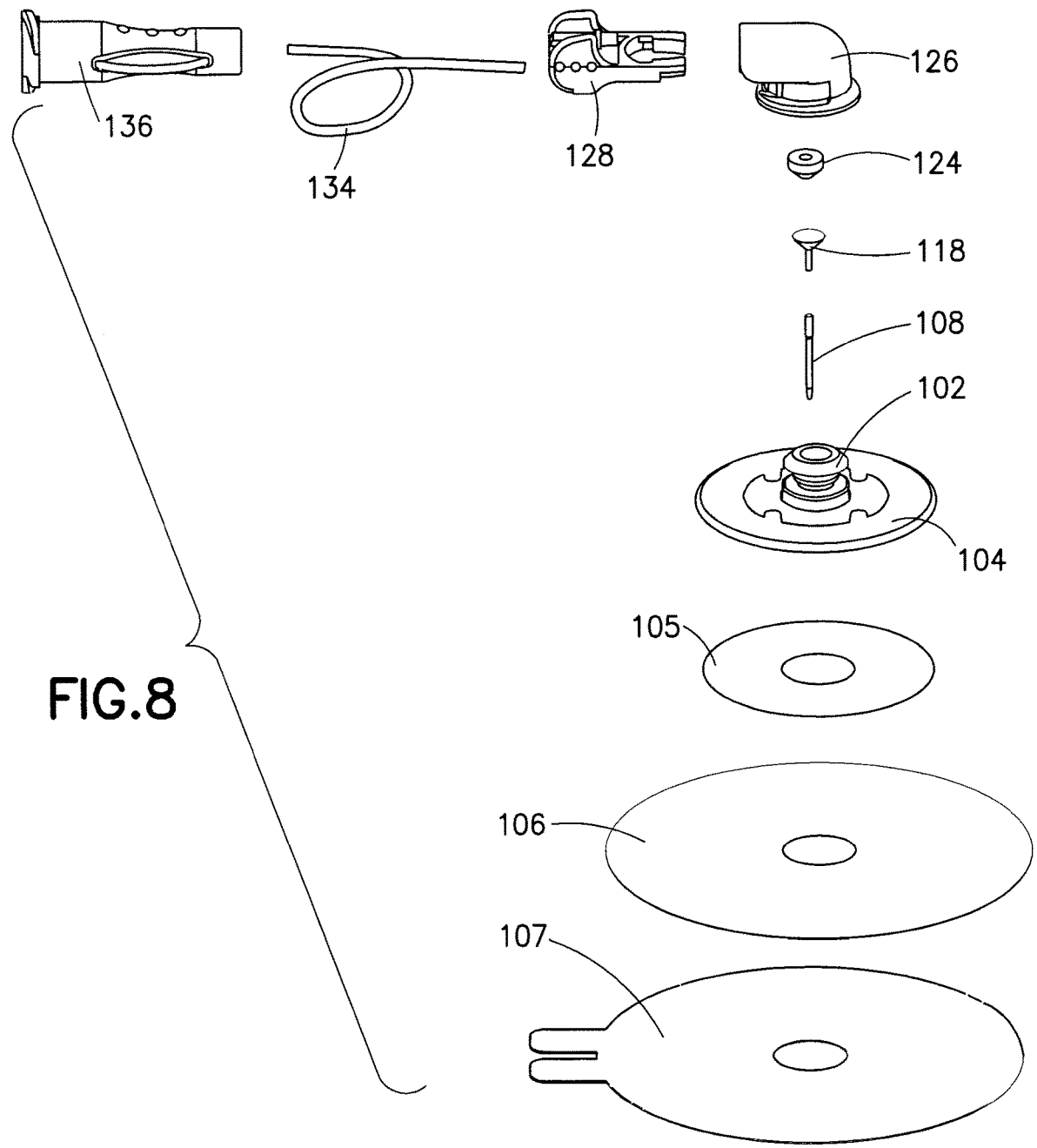

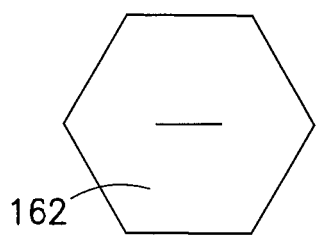 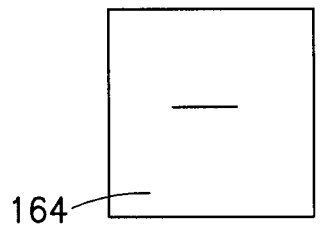 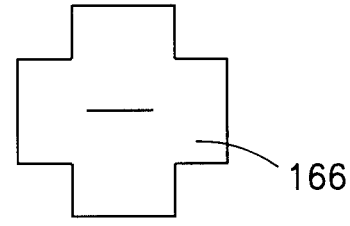
FIG.15  FIG.16  FIG.17
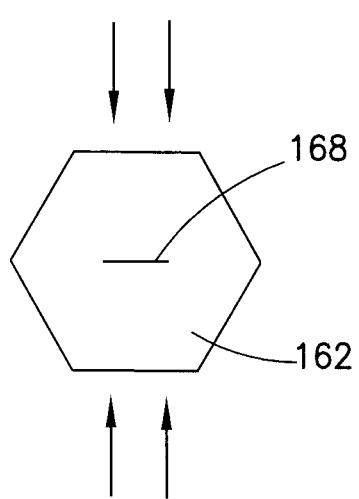 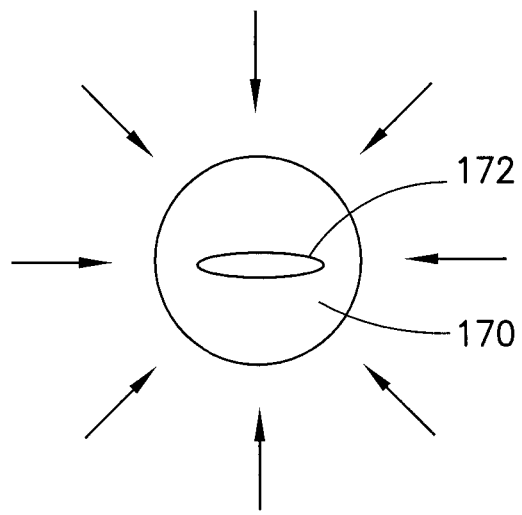
FIG.18  FIG.19
CONVENTIONAL ART

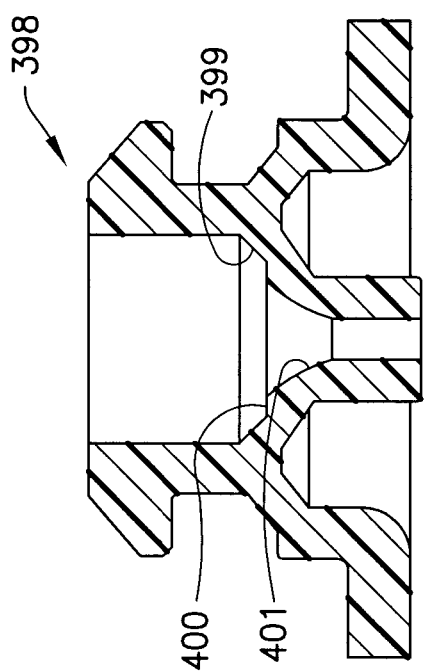
FIG.78
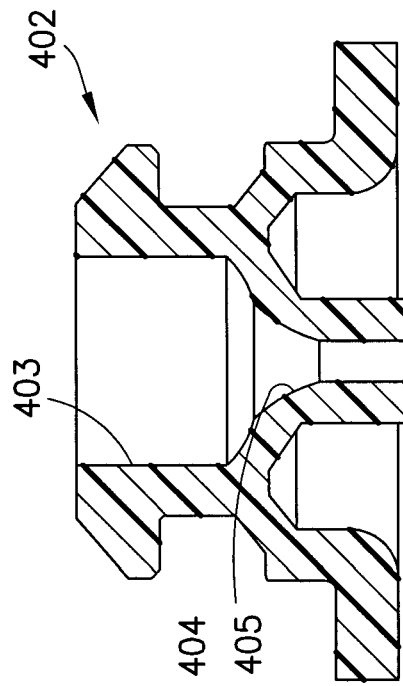
FIG.79
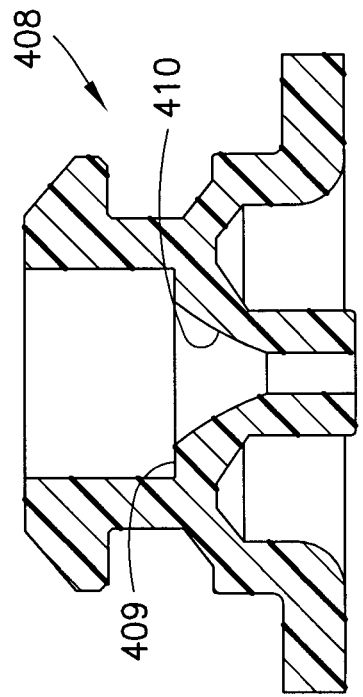
FIG.80
FIG.81

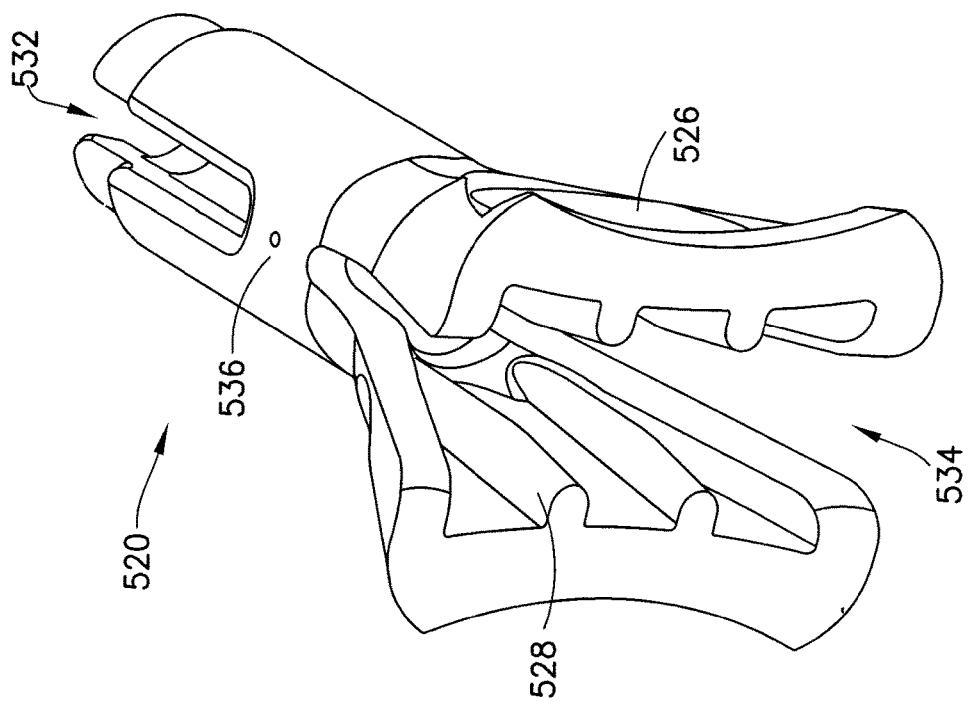
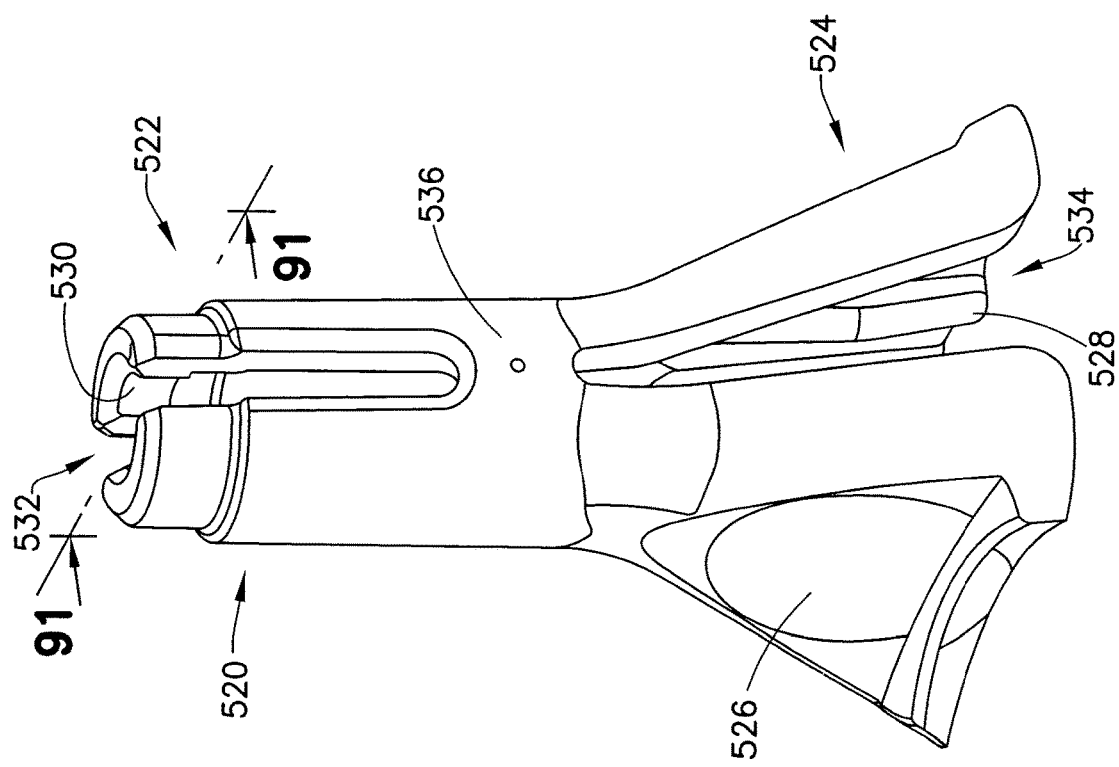

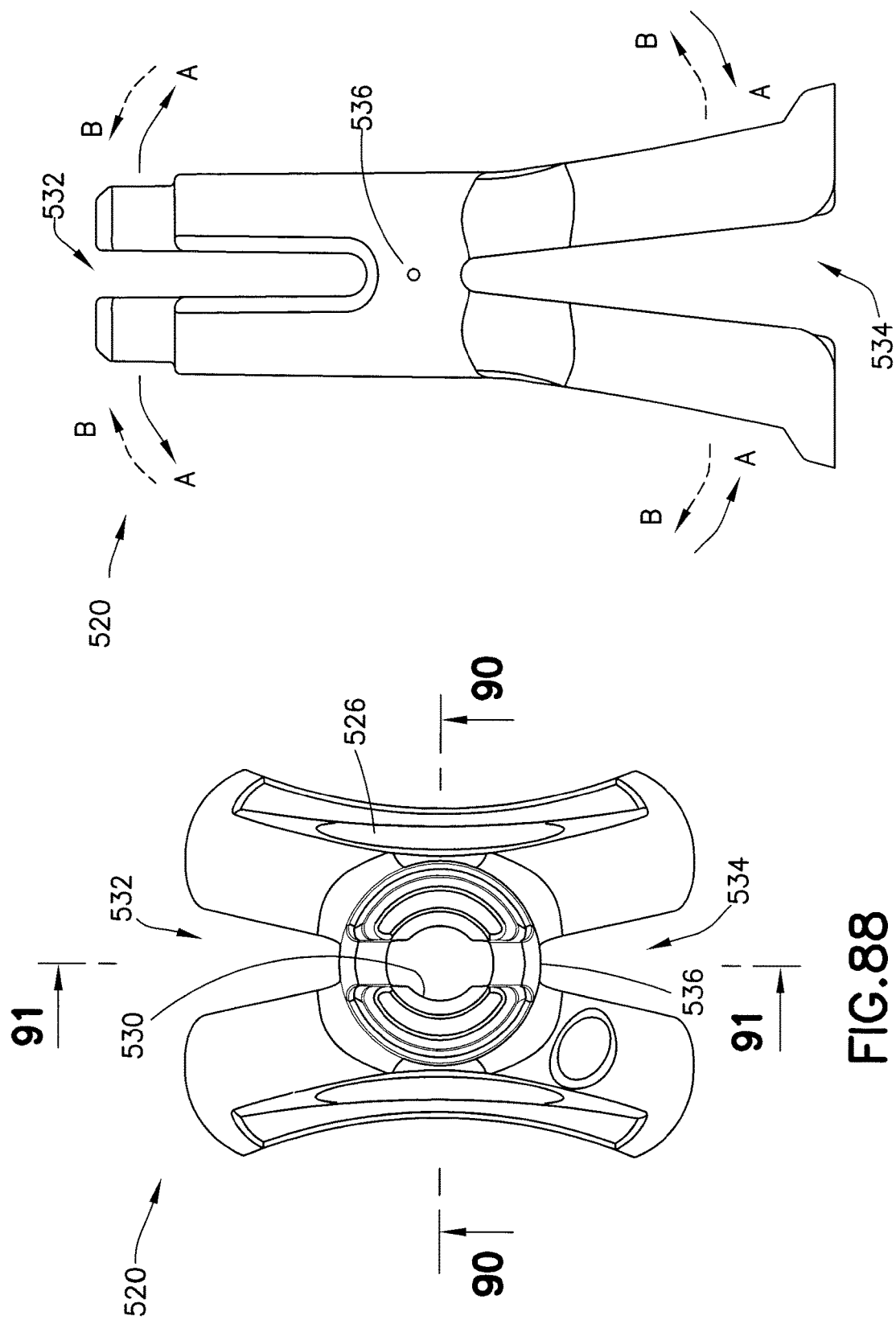

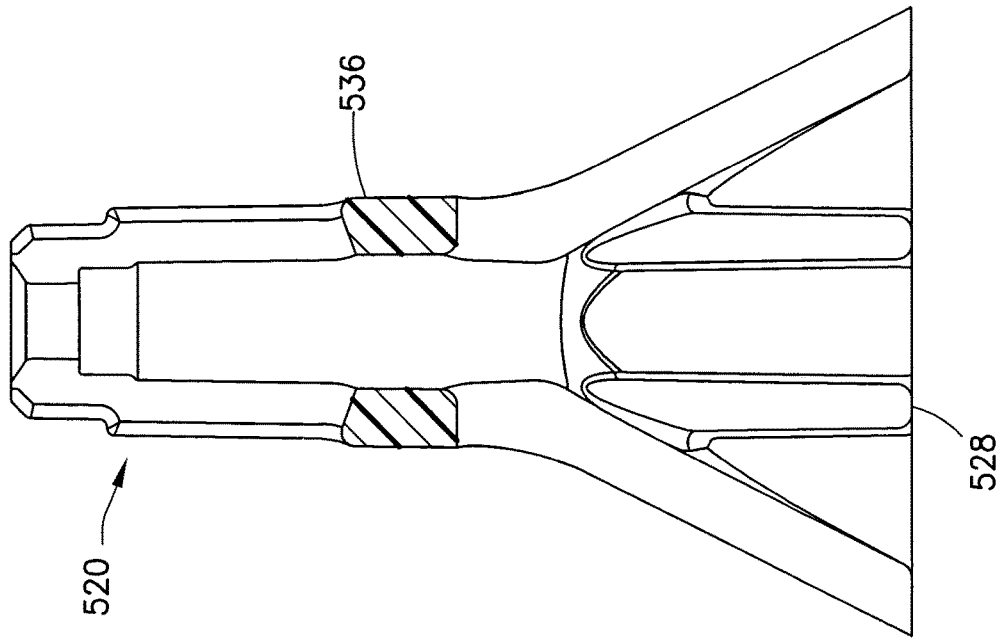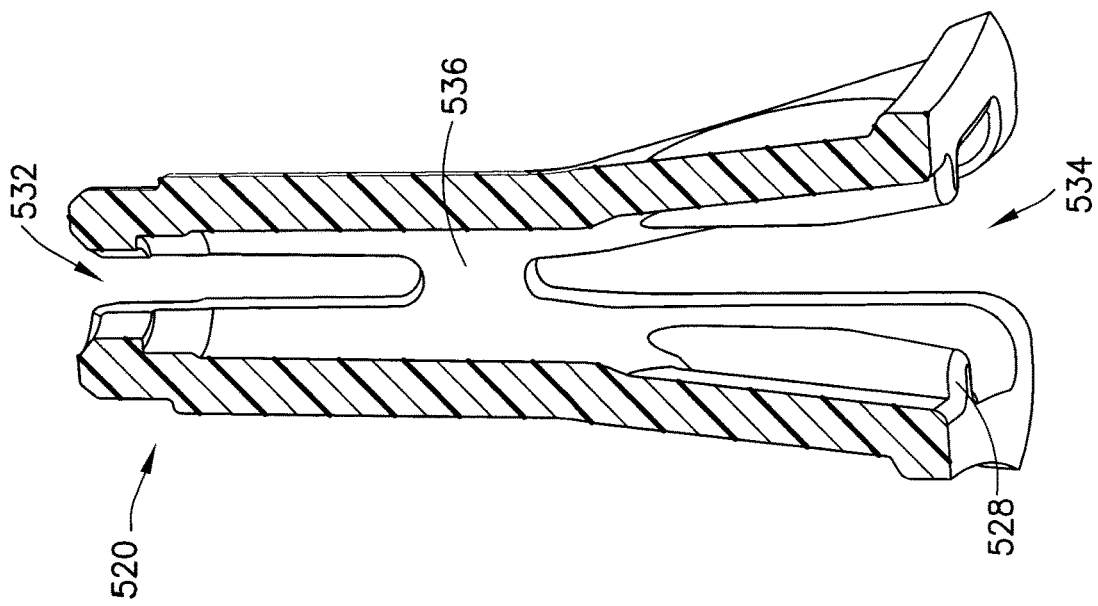

INFUSION DEVICE WITH RELEASABLE FLUID CONNECTOR

CROSS-REFERENCE TO RELATED APPLICATIONS

This application is a continuation of U.S. patent application Ser. No. 14/362,104, filed on May 30, 2014, which is the U.S. national stage of International Application No. PCT/US12/68632, filed on Dec. 7, 2012, which claims priority under 35 USC § 119(e) from U.S. Provisional Application Nos. 61/568,074, 61/692,985, and 61/719,755 filed on Dec. 7, 2011, Aug. 24, 2012, and Oct. 29, 2012 respectively. The disclosure of each of these applications is incorporated herein by reference in its entirety.

FIELD OF THE INVENTION

The present invention relates generally to infusion devices, and more particularly, to subcutaneous infusion devices to be used in conjunction with an infusion pump in the infusion of insulin and other medicaments.

BACKGROUND OF THE INVENTION

One mode of insulin infusion treatment includes infusion pump therapy via a catheter, needle or other type of cannula. Infusion pumps offer the advantages of continuous infusion of insulin, precision dosing, and programmable delivery schedules. Together, these advantages result in more accurate blood glucose control. In this mode of insulin infusion treatment, the infusion pump remains attached to the user and required doses of insulin are delivered to the user via the pump.

One type of cannula is a catheter, which generally is a tube that can be inserted into the body to permit the administration of fluids. In infusion pump therapy, the types and sizes of the catheter may vary, but generally, the catheter is a thin, flexible tube. In some uses, however, it may be larger and/or rigid. A rigid, hollow, metal needle may also be used in place of a soft plastic catheter.

One type of conventional infusion set is sold as the Quick-Set® infusion set by Medtronic. In such devices, the infusion pump includes a catheter assembly connected to a pump via a tubing set, and a separate insertion device inserts and/or attaches the catheter assembly into/to a user via an introducer needle provided as part of the infusion set. The infusion set and insertion device can also be combined, as in the Mio® infusion set sold by Medtronic, which is an "all-in-one" design that combines the infusion set and insertion device into one unit.

Another type of insulin infusion device, known as a "patch pump," has recently become available. Unlike a conventional infusion pump, a patch pump is an integrated device that combines most or all of the fluid components in a single housing that is adhesively attached to an infusion site, and does not require the use of a separate infusion (tubing) set. A patch pump adheres to the skin, contains insulin (or other medication), and delivers the drug over a period of time, either transdermally, or via an integrated subcutaneous mini-catheter. Some patch pumps communicate with a separate controller device wirelessly (such as one sold under the brand name OmniPod®), while others are completely self-contained.

A conventional infusion device can include a fluid connector, which may be releasably attached to a base that can be secured to a user's skin. An infusion pump supplies fluid to a catheter via the fluid connector/base engagement.

With such devices, however, there are concerns over the difficulty of balancing the force required to disconnect the tubing without pulling the catheter from the user's skin versus having enough retention force to secure the infusion components for everyday infusion. Another concern is that there may be a need to design a rotational lock between the fluid connector and the base. Yet another concern is that the separation force needs to be designed such that if a user accidentally snags the extension tubing on an external structure (e.g., a doorknob), the extension tubing will disconnect from the fluid connector without removing the catheter from the user's skin, thus saving the patient from the need to obtain, connect and re-insert a new infusion set.

Additionally, to protect the cannula and/or introducer needle prior to insertion, conventional devices often include a needle guard that is removed prior to use. These needle guards, however, are often very small and may be difficult to grasp, particularly for people with impaired dexterity. Additionally, conventional needle guards are often held in place by friction alone. To remove such needle guards, patients must pull and/or twist the needle guard, and the axial force required to remove such needle guards may vary widely, for example, based on manufacturing tolerances. Further, with such needle guards, once the coefficient of static friction is overcome, the guard may separate quickly, without providing an opportunity for a user to modify the applied force and potentially resulting in a needle-stick injury. Further, there is a risk that the needle guard can contact the needle during removal, potentially dulling the cannula or introducer needle.

SUMMARY OF THE INVENTION

An object of embodiments of the present invention is to substantially address the above and other concerns, and provide improved infusion devices. Another object of embodiments of the present invention is to provide an infusion device configured to balance the separation force needed to separate an extension tube from an inserted catheter with the retention force needed to maintain engagement between the extension tube and inserted catheter, to provide efficient infusion while preventing accidental removal of the catheter.

These and other objects are substantially achieved by providing an infusion set system, including a base attachable on a distal side thereof to a patient at an infusion site, and a fluid connector removably coupleable to the base. The base includes a base section extending proximally from a surface of the base, a latching portion extending proximally from the base section, and a base latch extending proximally from the latching portion. The latching portion has a smaller lateral width than the base latch. At least one of the base section and the base latch has a plurality of substantially flat side surfaces.

The fluid connector includes a fluid path portion and at least one connector latch displaceably connected to the fluid path portion and displaceable to a latching position in which at least a portion of the connector latch extends into the fluid path portion. The fluid path portion includes a cannula extending from a top interior surface of the fluid path portion, and a plurality of internal sidewalls corresponding to at least two of the plurality of the flat side surfaces of the at least one of the base section and the base latch, thereby facilitating connection between the base and the fluid connector in a plurality of discrete rotational connecting positions. When the fluid connector is locked to the base, the at least one connector latch engages the latching portion of the base and restricts proximal displacement of the fluid connector relative to the base.

These and other objects are also substantially achieved by providing a two-piece fluid connector that includes a fluid path portion and a latching portion secured to the fluid path portion and having at least one displaceable arm. The fluid path portion includes a cannula integral with and extending from a proximal interior surface of the fluid path portion. The arm includes a connector latch disposed at a first end of the arm, and an activation lever disposed at an opposite end of the arm. The connector latch is displaceable to a latching position in which at least a portion of the connector latch extends into an interior of the fluid path portion through side walls of the fluid path portion.

These and other objects are also substantially achieved by providing a septum that includes a peripheral portion having a substantially straight external side and a peripheral thickness along a first axis substantially parallel to the external side, and a web portion surrounded by the peripheral portion, the web portion having a central portion surrounded by a connecting portion connecting the central portion with the peripheral portion. The central portion has a maximum central thickness along the first axis that is substantially less than the peripheral thickness and greater than a minimum thickness of the connecting portion along the first axis.

These and other objects are also substantially achieved by providing a needle guard for guarding a sharp cannula of an infusion device. The needle guard includes a proximal portion for connecting to the base of the infusion device, and a distal portion for user interaction. The proximal and distal portions each include at least one axial cutout that divides the needle guard into first and second lateral sides. A fulcrum web is disposed between the proximal and distal axial cutouts to join the first and second lateral sides of the needle guard and provide a fulcrum for relative rotation of the first and second lateral sides of the needle guard.

Additional and/or other aspects and advantages of the present invention will be set forth in the description that follows, or will be apparent from the description, or may be learned by practice of the invention.

BRIEF DESCRIPTION OF THE DRAWINGS

The various objects, advantages and novel features of the exemplary embodiments of the present invention will be more readily appreciated from the following detailed description when read in conjunction with the accompanying drawings, in which:

FIG. 8 is an exploded view of the fluid connector and base of FIG. 5;

FIG. 15 is a top view of a straight-sided split septum having a hexagonal shape in accordance with an exemplary embodiment of the present invention;

FIG. 16 is a top view of a straight-sided split septum having a square shape in accordance with an exemplary embodiment of the present invention;

FIG. 17 is a top view of a straight-sided split septum having a polygonal shape in accordance with an exemplary embodiment of the present invention;

FIG. 18 is a top view of a straight-sided split septum having a hexagonal shape in accordance with an exemplary embodiment of the present invention, the figures schematically illustrating retention forces acting on center slit;

FIG. 19 is a top view of a related art straight-sided split septum having a circular shape, the figure schematically illustrating retention forces acting on a center slit;

FIGS. 78-81 are partial cross-sectional views of bases in accordance with exemplary embodiments of the present invention;

FIG. 86 is a perspective view of a needle guard in accordance with an embodiment of the present invention;

FIG. 87 is a bottom perspective view of the needle guard of FIG. 86;

FIG. 88 is a top view of the needle guard of FIG. 86;

FIG. 89 is a side view of the needle guard of FIG. 86;

FIG. 90 is a perspective cross-sectional view of the needle guard of FIG. 86 taken along the line 90-90 of FIG. 89;

FIG. 91 is a perspective cross-sectional view of the needle guard of FIG. 86 taken along the line 91-91 of FIG. 88;

DETAILED DESCRIPTION OF EXEMPLARY EMBODIMENTS

Figure 1:
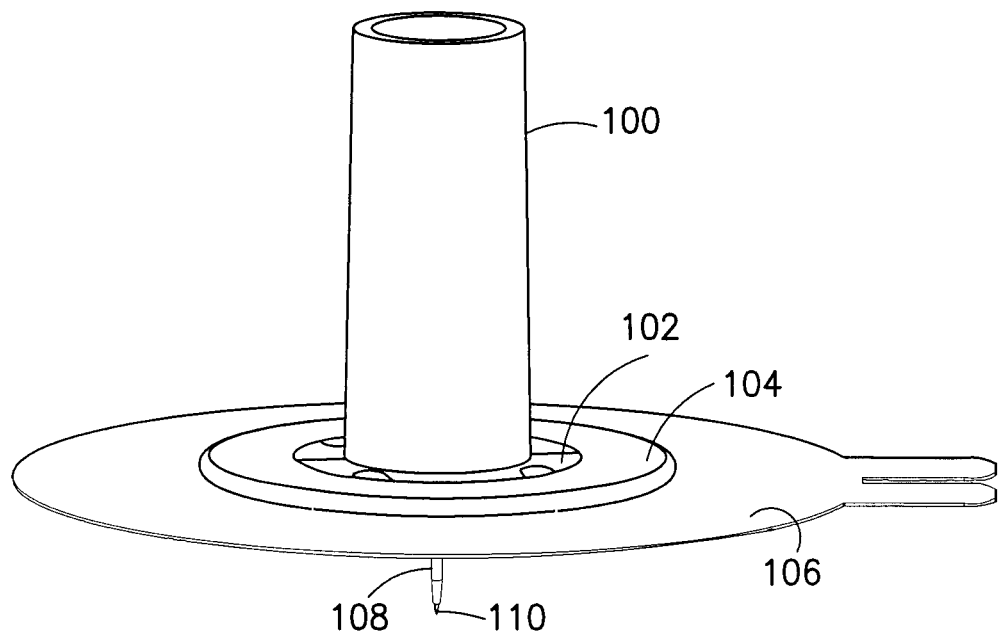
FIG. 1 is a perspective view of a needle hub connected to an infusion set base in accordance with an exemplary embodiment of the present invention.

Reference will now be made in detail to an embodiment of the present invention, which is illustrated in the accompanying drawings, wherein like reference numerals refer to like elements throughout. The embodiment described herein exemplifies, but does not limit, the present invention by referring to the drawings. As will be understood by one skilled in the art, terms such as up, down, bottom, top, proximal, and distal are relative, and are employed to aid illustration, but are not limiting.

FIG. 1 illustrates an exemplary embodiment of an infusion set comprising an introducer needle hub 100 engaged with a base 102. The base 102 engages a flexible disc 104 positioned between the base 102 and a user. The flexible disc 104 provides improved comfort and mobility of the device because it moves with the user during physical activity while minimizing contact of the rigid portions of the base 102 with the user. The flexible disc 104 is attached to an adhesive patch or pad 106 having an adhesive backing, which is used to secure the base 102 to the user's skin. FIG. 1 illustrates a state in which the introducer needle hub 100 and base 102 are ready to facilitate insertion of a soft (flexible) catheter 108 and an introducer needle 110 into the user.

Figure 2:
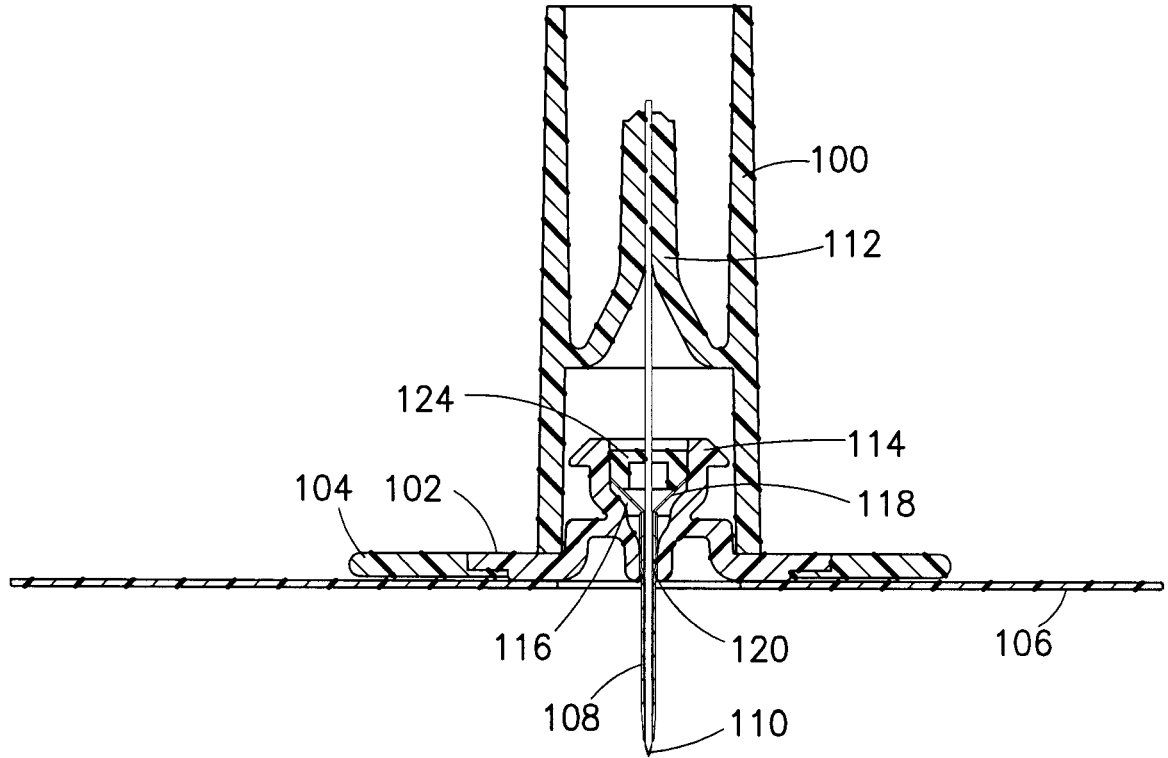
FIG. 2 is a cross-sectional view the needle hub and base of FIG. 1.

FIG. 2 is a cross-sectional view of the base 102 and introducer needle hub 100 configuration shown in FIG. 1. The introducer needle 110 is fixed to a needle mounting structure 112 within the introducer needle hub 100, thus fixing the introducer needle 110 against axial movement relative to the hub 100. The introducer needle hub 100 is used to insert the introducer needle 110 and the catheter 108 into the user without requiring the user to hold or manipulate the introducer needle 110 directly. The introducer needle 110 is preferably a hollow stainless steel needle with a sharp beveled distal end.

Figure 3:
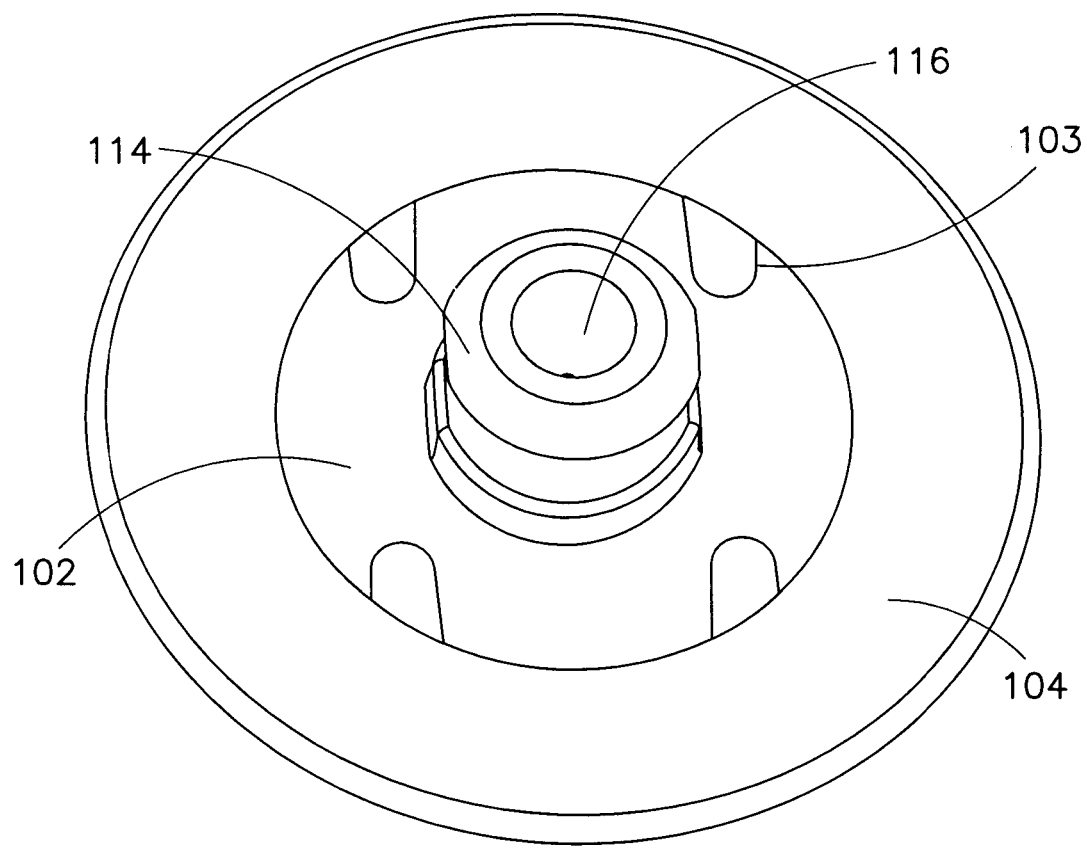
FIG. 3 is a perspective view of the base of FIG. 1.
Figure 4:
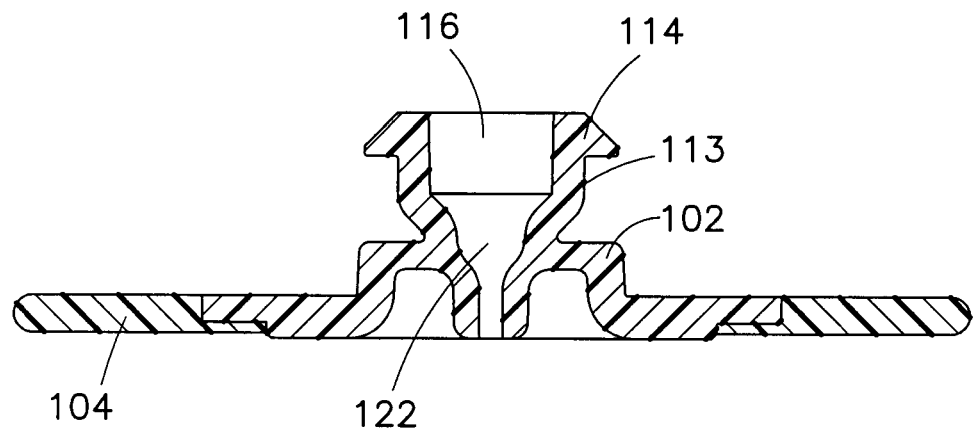
FIG. 4 is a cross-sectional view of the base of FIG. 1.

FIGS. 2-4 further illustrate features of the base 102. The base 102 includes a columnar post 113 surrounding an internal cavity 116. A mushroom-shaped base latch 114 is disposed at the proximal end of the post 113. The internal cavity 116 generally extends through the center of the base 102 providing a fluid passageway through the base 102. As shown, for example, in FIG. 2, the internal cavity 116 of the base 102 receives a retaining wedge 118 and a catheter 108. The wedge 118 has a funnel shape with a hollow center portion that narrows from a broad end to a narrow end 120. The narrow end 120 of the wedge 118 has a tapered end used to receive a terminal end of the catheter 108. The catheter 108 is forced over the narrow end 120 of the wedge 118 and the wedge/catheter assembly is inserted into the internal cavity 116 of the base 102.

Due to the flexible characteristics of the catheter 108, it may have a tendency to bunch up within the base 102 and therefore, the base 102 provides an additional cavity area 122 to accommodate excess catheter 108 material that may accumulate within the base 102 during the installation of the catheter onto the wedge 118. A pre-slit resilient septum 124 is also retained within the internal cavity 116 of the base 102. According to an exemplary embodiment, the septum 124 is held in place within the base 102 by a press fit, which provides a friction force between the septum 124 and both the base 102 and the wedge 118. Alternatively, the septum 124 may be fixed within the base 102 by an adhesive or by swaging plastic material from the base 102 over the top of the septum, or a combination of the above-described methods.

FIGS. 3 and 4 also illustrate first and second molded shots used in manufacturing base 102. The second molded shot (disc 104) may be of the same material as the first shot or may be of a different, more flexible material, which may include a silicone or thermoplastic elastomer, and thus, may be the flexible disc 104. As shown in FIG. 3, cutouts or holes 103 in the base 102 become filled with the material for the flexible disc 104, and thus, facilitate bonding between the base 102 and the flexible disc 104.

Figure 5:
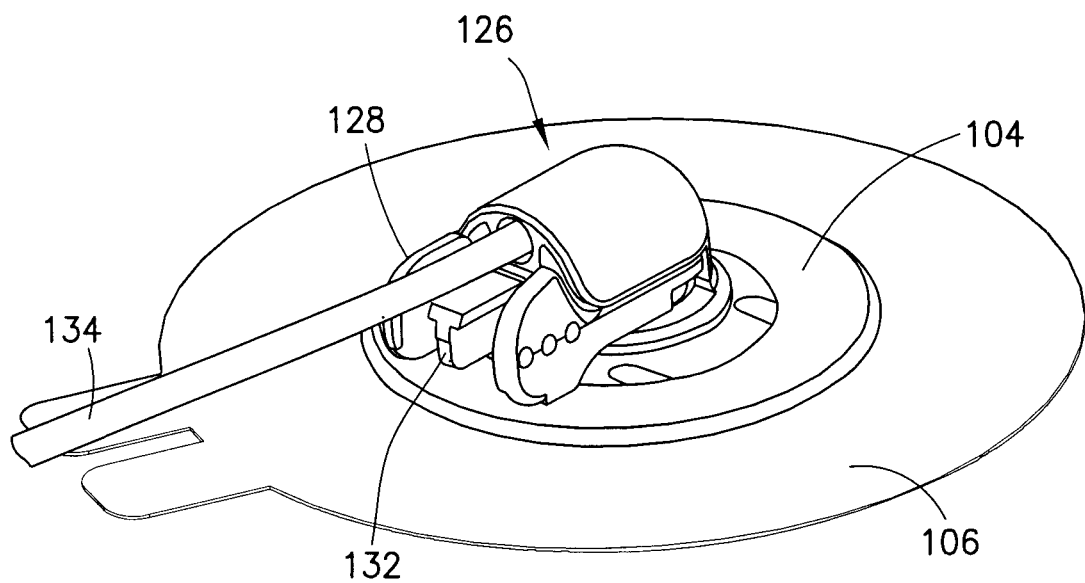
FIG. 5 is a perspective view of a fluid connector attached to the base of FIG. 1 in accordance with an embodiment of the present invention.
Figure 6:
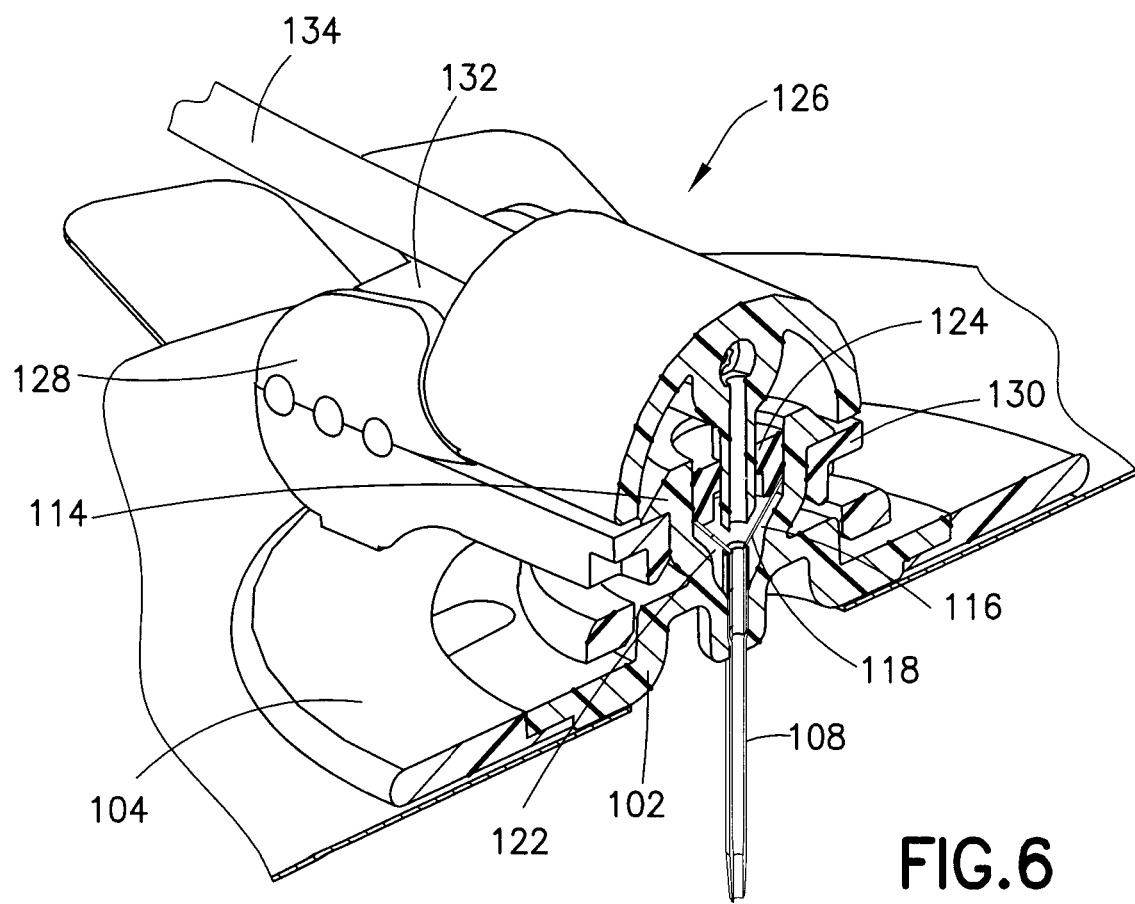
FIG. 6 is a cross-sectional view of the fluid connector and base of FIG. 5.
Figure 7:
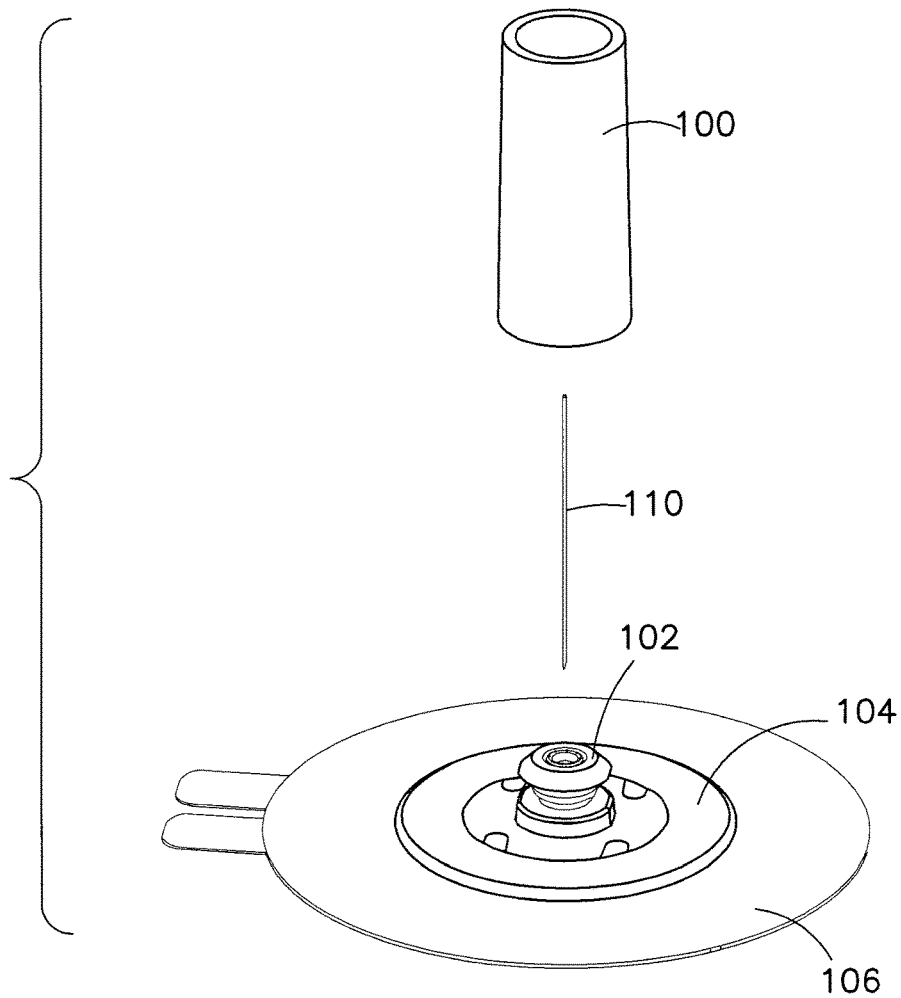
FIG. 7 is an exploded view of the needle hub of FIG. 1.

FIGS. 5 and 6 illustrate a fluid connector or fluid connector 126 connected to the base 102, and FIG. 7 illustrates an exploded view of the introducer needle hub 100 and base 102. The fluid connector 126 includes activation levers 128, fluid connector latches 130, and a rigid stop 132 (best shown in FIG. 11). The user attaches the fluid connector 126 to the base 102 by pressing the fluid connector axially down onto the base 102 and snapping it in place. In this process, the latches 130 and activation levers 128 resiliently deflect to allow the latches to pass over the mushroom-shaped base latch 114. Subsequently, the latches 130 and activation levers 128 return substantially to their undeformed or less deformed positions with the latches resiliently engaging the underside of the mushroom-shaped base latch 114 to prevent axial displacement of the fluid connector 126 relative to the base 102. In other words, during connection, the fluid connector latches 130 slide over the mushroom-shaped base latch 114 and resiliently return to a position where they snap and engage the base 102 via engagement with the post 113 and the base latch 114.

The user removes the fluid connector 126 by pressing the activation levers 128 together until they engage the rigid stop 132, thereby disengaging the latches 130 from the mushroom-shaped base latch 114. Then the user then lifts the fluid connector 126 axially away from the base 102

In this exemplary embodiment, the activation levers 128 and the fluid connector latches 130 are molded from a resilient plastic material as a separate component from the fluid connector 126. The activation levers 128 and fluid connector latches 130 pivot on a living hinge. This may simplify manufacturing and reduce mold complexity. The rigid stop 132 ensures that both of the fluid connector latches 130 travel far enough to completely disengage from the mushroom-shaped base latch 114. The rigid stop 132 also provides a stable anchor for the activation levers 128 during the handling of the fluid connector 126. Further, the rigid stop 132 prevents the fluid connector 126 from rocking when connected to the base 102. Additionally, according to one embodiment, the fluid connector 126 can freely rotate 360 degrees about the base 102, which provides the user with the ability to position the extension tubing 134, which connects the fluid connector 126 to an infusion pump.

Figure 9:
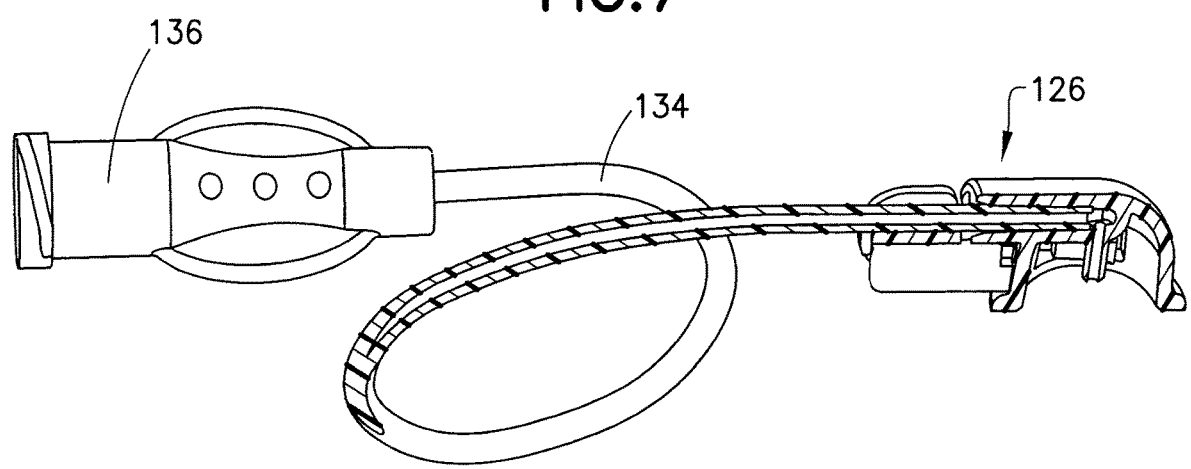
FIG. 9 is perspective view of the fluid connector of FIG. 5 and a reservoir connector.

FIGS. 8 and 9 illustrate an exploded and perspective view, respectively, of the components of an exemplary embodiment of an infusion set. The infusion set includes the fluid connector 126 and the base 102 as described above, and also includes the extension tubing 134 connecting the fluid connector 126 to a reservoir connector 136 that connects to an infusion pump, as well as a base adhesive 105 for connecting the adhesive patch 106 to the base 102 and/or the flexible disc 104, and an adhesive backing 107 for selectively protecting the distal adhesive surface of the adhesive patch 106.

Figure 10:
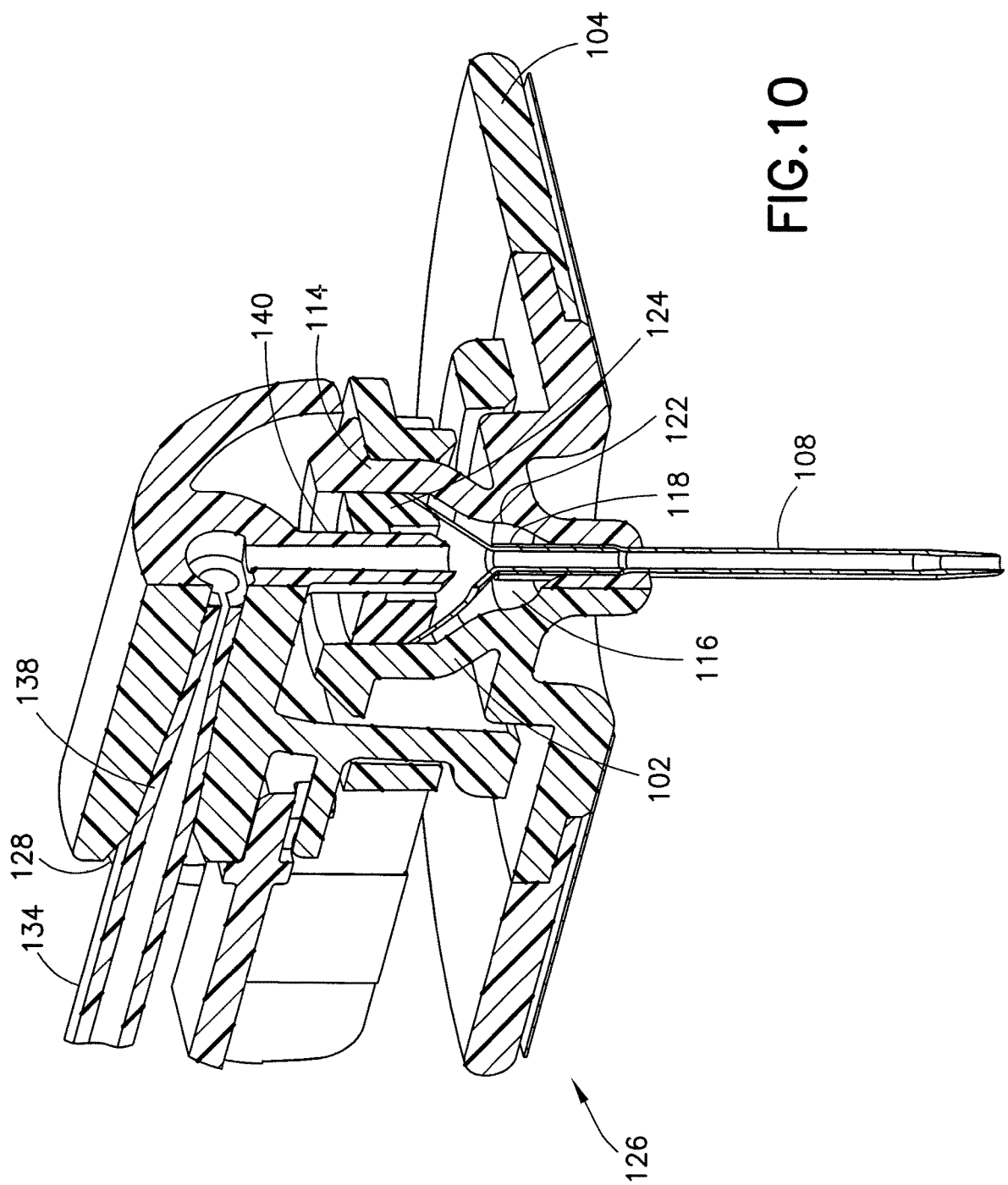
FIG. 10 is another cross-sectional view of the fluid connector and the base of FIG. 5.

FIG. 10 is a sectional view depicting a connected fluid path provided by the fluid connector 126 and the base 102. In this embodiment, the extension tubing 134 is connected to a tubing port 138 on the fluid connector 126. According to one embodiment, the tubing port 138 provides a press fit connection for the extension tubing 134, facilitating fluid flow from the infusion pump, through the extension tubing 134 and into the fluid connector 126. According to another embodiment, glue, or another bonding mechanism, such as solvent bonding, is used to secure the extension tubing 134 to the tubing port 138. The fluid path continues from the tubing port 138 into a molded cannula 140.

The molded cannula 140 extends in a direction substantially perpendicular to the longitudinal direction of the tubing port 138. In this embodiment, the molded cannula 140 is a rigid, substantially tubular member made of plastic and having either a tapered or rounded terminal end. The terminal end of the molded cannula 140 is used to penetrate through a pre-formed slit in the septum 124, thus providing a sealed fluid connection between the extension tubing 134 and the catheter 108. Fluid flows through the molded cannula 140, through the septum 124, then through the wedge 118 and into the catheter 108. The septum 124 provides a self-sealing feature, preventing fluid from exiting or leaking out of the base 102, except through the catheter 108. According to one embodiment, the molded cannula 140 is formed as an integral part of the fluid connector 126.

Figure 11:
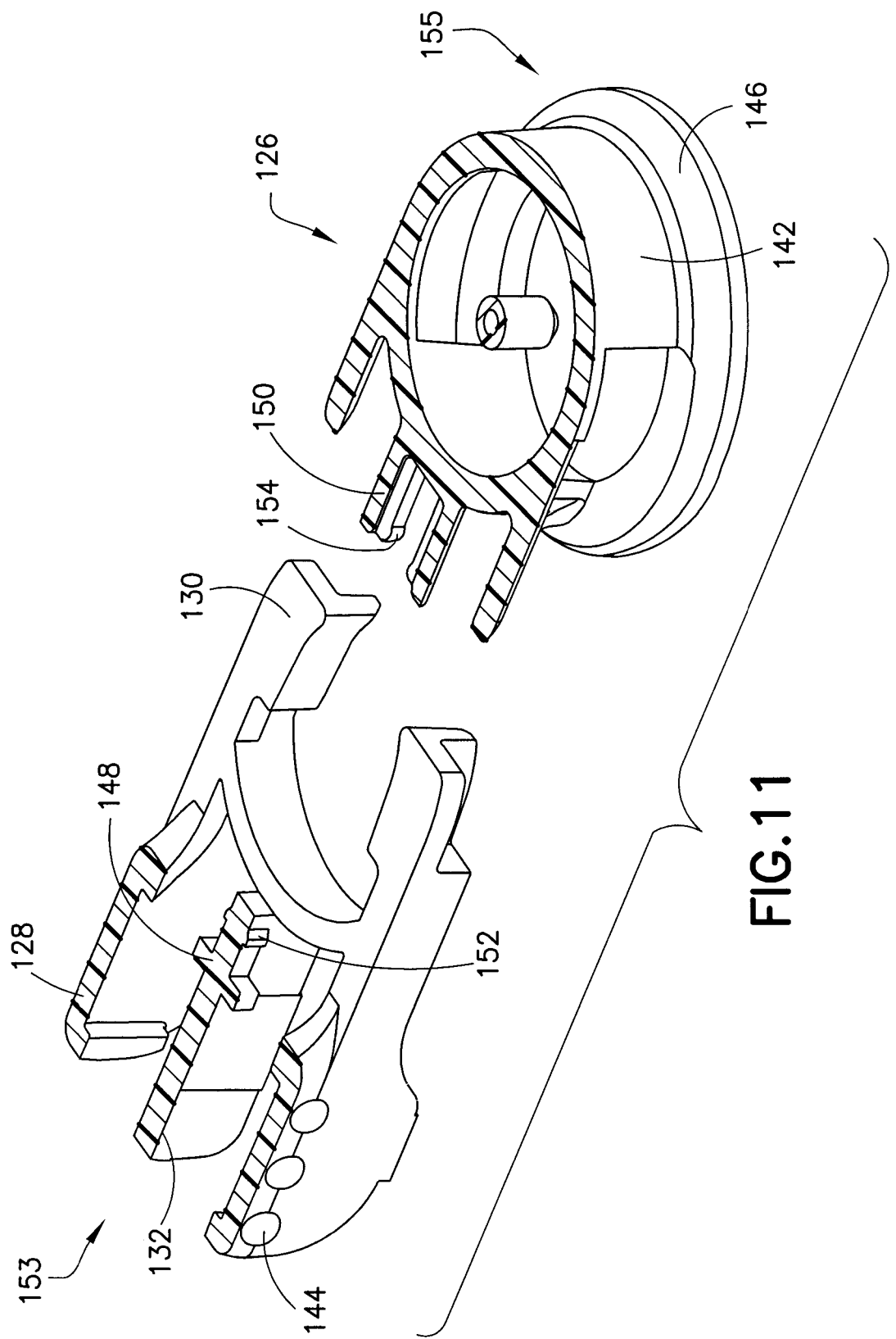
FIG. 11 is an exploded view of the fluid connector of FIG. 5.

FIG. 11 is an exploded, perspective, cross-sectional view of the fluid connector 126. In this exemplary embodiment, the fluid connector 126 is formed using two distinct components: a first component 153, including the fluid connector latches 130 and the corresponding activation levers 128, and a second component 155, including the fluid connector shroud 142 (the top half of each component being omitted for clarity). The activation levers 128 have finger bumps 144 to aid the user in locating and using the activation levers 128. Alternatively, the finger bumps 144 may be replaced with a ridge or divots that can provide tactile feedback to the user regarding where to press to release the fluid connector 126 from the base 102. According to one embodiment, the activation levers 128 can have a different color than the fluid connector 126 to provide a visual indicator for the same purpose. The fluid connector shroud 142 of the fluid connector 126 has a smooth rounded exterior surface that aids in minimizing snagging or catching the fluid connector 126 on clothing or other objects during use. At the base of the fluid connector 126 there is a circular anchoring ring 146. The anchoring ring 146 forms a foundation and provides added stability around the base 102 when the fluid connector 126 engages with the base 102.

FIG. 11 also illustrates how the fluid connector shroud 142 and the fluid connector latches 130 are assembled. A male T-slot 148 feature on the first component 153 engages with a female T-slot 150 feature on the second component 155. Detents 152 and 154 on the first and second components 153 and 155 provide a mechanical lock between the two components. Alternatively, the fluid connector latches 130 and the fluid connector shroud 142 can be formed as a single integral molded plastic piece.

Figure 12:
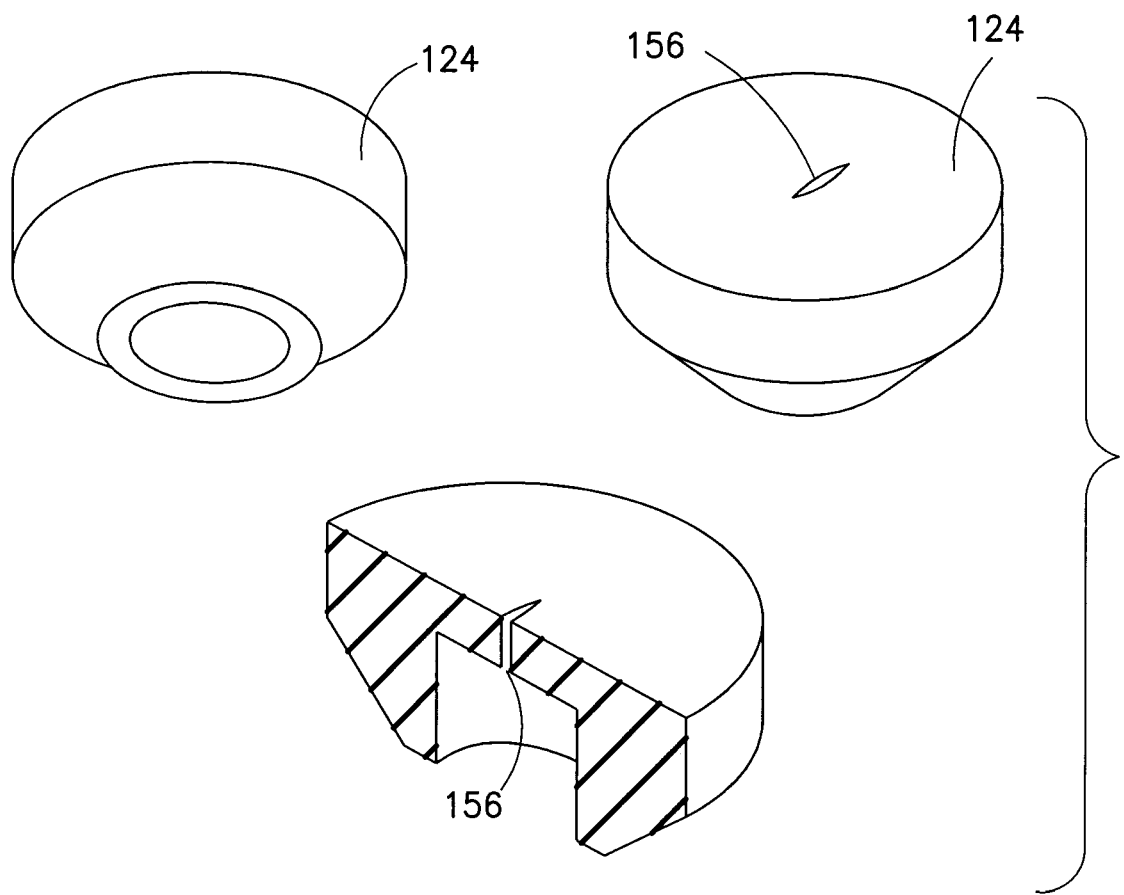
FIG. 12 illustrates opposing perspective views and a cross-sectional view of a split septum in accordance with an exemplary embodiment of the present invention.

FIG. 12 illustrates the self-sealing resilient septum 124, which has a pre-pierced center 156 (shown partially opened for illustrative purposes) to receive the blunt molded cannula 140 from the fluid connector 126 and facilitate penetration of the septum 124. According to one embodiment, the septum 124 is under inward radial compression to ensure a seal at all times, with or without the molded cannula 140 being present. The septum 124 can be made of a soft resilient material including, but not limited to silicones, isoprene rubbers, or bromobutyl rubbers. The septum 124 can be made from a combination of these materials as well. The septum 124 ensures a complete seal during infusion and when the fluid connector 126 is disconnected from the base 102. The slit geometry of the septum 124 may be a single straight slit or multiple, intersecting straight slits. The slit may also be curved to ensure a complete seal during infusion and while the connecter hub 126 is disconnected from the base 102.

Figures 13, 14:
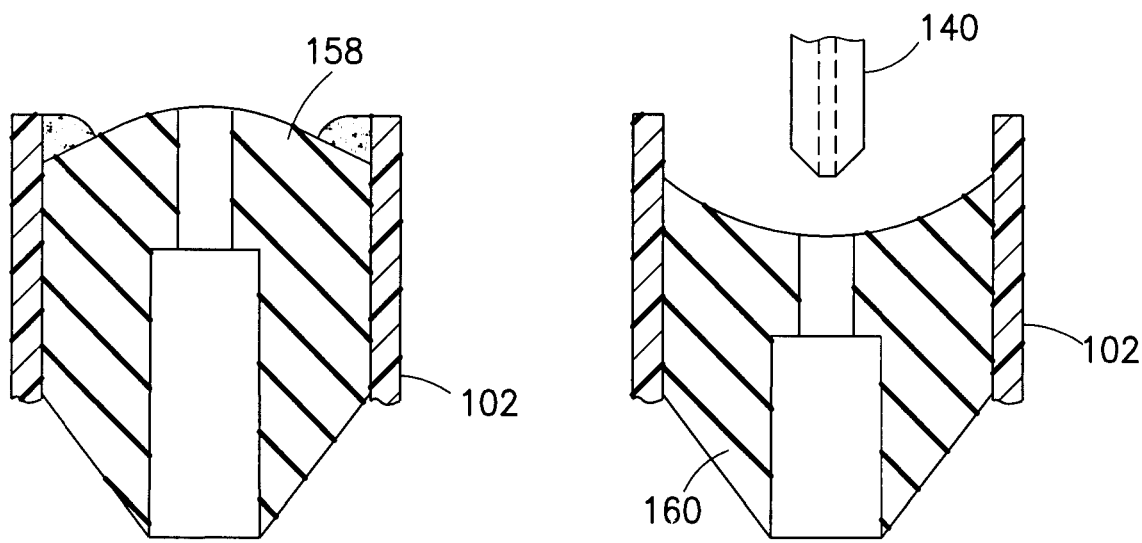
FIG. 13 illustrates a side view of a septum having a convex top surface and a cross-sectional view of a base receiving the septum in accordance with an exemplary embodiment of the present invention.
FIG. 14 is a side view of a septum having a concave top surface and a cross-sectional view of a base receiving the septum in accordance with an exemplary embodiment of the present invention.

FIG. 13 illustrates another exemplary embodiment of a septum 158 for use in the base 102. In this embodiment, the septum 158 has a convex top surface that can be more easily swabbed and can also aid in keeping the top center portion of the septum 158 free from glue or debris that may remain on the septum after it is secured to the base 102. All the septa described herein can be secured to the base by a friction fit, swaging, an adhesive, or a combination thereof. The convex top surface of the septum 158 also provides additional sealing pressure, keeping the pre-pierced slit sealed, particularly when external forces are applied to the septum 158 when a fluid connector is disconnected from the base 102.

FIG. 14 illustrates an alternative exemplary embodiment of the septum 160 for use in the base 102. In this embodiment, the septum 160 has a concave top surface that can aid in centering the molded cannula 140 when the fluid connector 126 is engaged with the base 102.

FIG. 15 is a top view of a straight-sided split septum 162 having a hexagonal shape. Assuming the base 102 has a corresponding hexagonal shape, the straight sides allow compression of the septum 162 to have at least a component of the force that acts in a direction that is perpendicular to the slit in the septum 162. And for the sides that are parallel to the slit, all of the compression forces from those sides are directed perpendicular to the slit. Further, if the septum 162 is only compressed on sides parallel to the slit, then all the compression force is directed perpendicular to the slit. This ensures that the septum 162 is always sealed.

Similarly, FIG. 16 is a top view of a straight-sided split septum 164 having a square shape, and FIG. 17 is a top view of a straight-sided split septum 166 having a polygonal shape.

Figure 23:
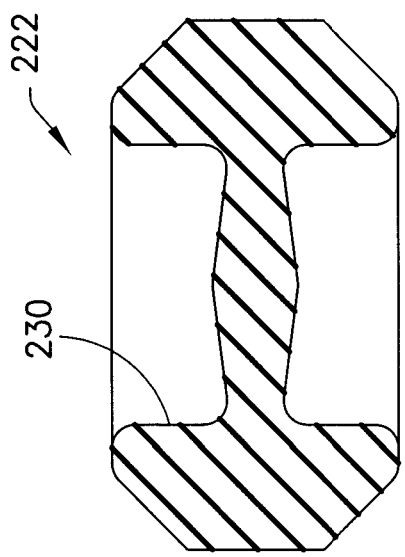

FIG. 18 schematically illustrates the direction of the retention forces acting on the center slit 168 of the septum 162. In contrast, FIG. 19 is a top view of a conventional straight-sided split septum 170 having a circular-shaped cross-section. FIG. 23 also schematically illustrates the retention forces acting on the center slit 172, creating forces that act to both open and close the slit 172.

Figure 20:
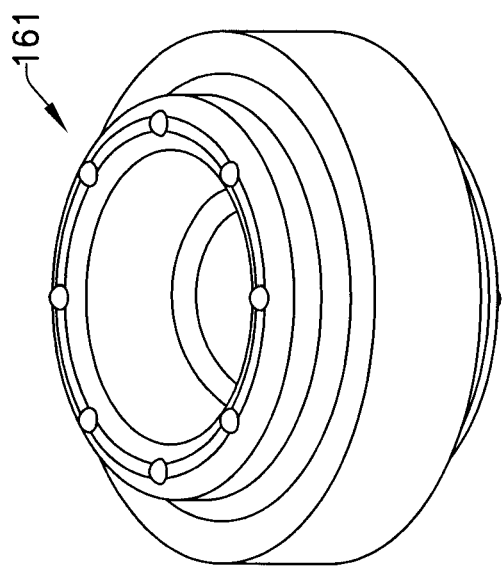
FIGS. 20 and 21 are perspective and cross-sectional views, respectively, of a septum in accordance with an exemplary embodiment of the present invention.
Figure 21:
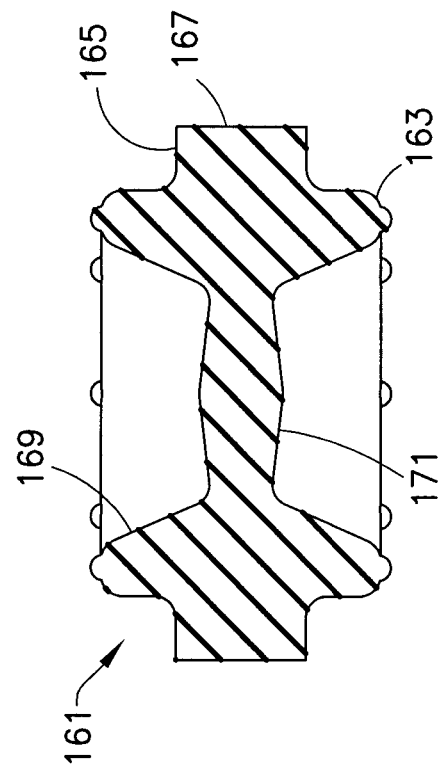

Respectively, FIGS. 20 and 21 are perspective and cross-sectional views of a septum 161 in accordance with another exemplary embodiment of the present invention. The septum is substantially a rotational solid with a thick inner wall 163 (about 0.07" (1.7 mm)), an outer band 165 with an exterior face 167 that has a reduced thickness (about 0.03" (0.76 mm)), compared with the thick inner wall 163, to reduce surface area contact, and thus friction, with the base 102. According to one embodiment, the septum 161 has a diameter of about 0.126" (3.2 mm).

The radially inward face 169 of the inner wall 163 is sloped, and has an included angle of about 45 degrees. Connecting the face 169 is a central horizontal portion or web 171 that is slightly thicker at its central portion than where it meets the face 169, and vertically, is centrally located. The angle α represents the taper of the web 171, and is about fourteen degrees. According to one embodiment, the septum 161 has a central slit. The web 171 includes convex top and bottom surfaces that contain the slit. These convex surfaces provide additional sealing pressure, keeping the slit sealed, particularly when external forces are applied to the septum 161 when the fluid connector 126 is disconnected from the base 102.

The septum 161 includes symmetric concave surfaces (formed by the sloped inward face 169) on both the top and bottom surfaces that aide in centering a cannula (such as cannula 140) through the slit in the septum 161 during assembly and improve the sealing ability of the septum 161 with respect to the cannula.

Figure 22:
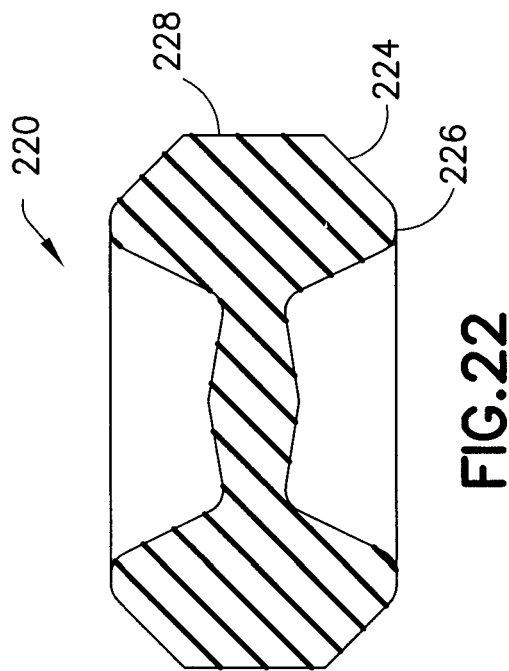
FIGS. 22 and 23 are cross-sectional vies of respective septa in accordance with exemplary embodiments of the present invention.

FIGS. 22 and 23 are cross-sectional views of septa 220 and 222 that are similar to septum 161 in most respects. In septum 220, the face 224 connecting the inner wall 226 with the exterior face 228 is beveled at about 45 degrees, in contrast to the concave shape of the septum 161. Septum 222 is substantially similar to septum 220, except that the inward face 230 is substantially vertical, rather than being sloped.

Figure 24:
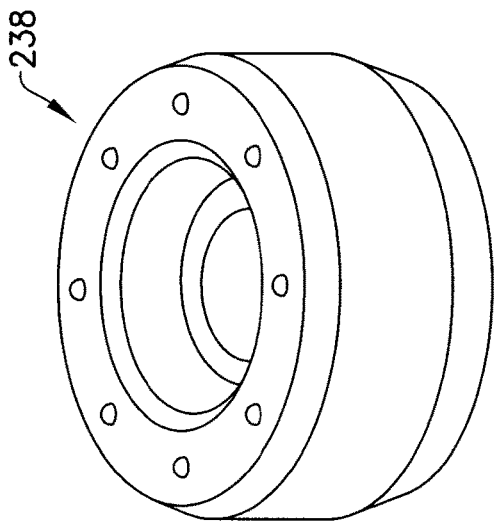
FIGS. 24 and 25 are perspective and cross-sectional views, respectively, of a septum in accordance with an exemplary embodiment of the present invention.
Figure 25:
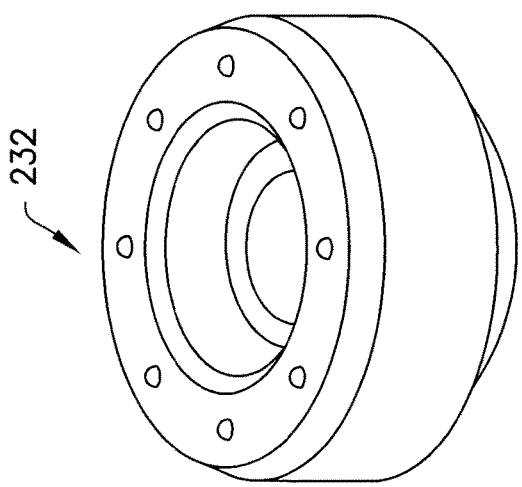

Respectively, FIGS. 24 and 25 are perspective and cross-sectional views of a septum 232 in accordance with another exemplary embodiment of the present invention. In comparison to the septa of FIGS. 20-23, the septum 232 has a thicker central web 234 (about 0.03" (0.76 mm)). The angle α of the slope of the web 234 is about thirteen degrees. The bottom of septum 232, however, is substantially similar to the bottom of septum 161. It will be understood by one skilled in the art that the terms "bottom" and "top" are used in reference to the drawings, and are not limiting. The bevel angle β at the top of the septum 232 is about 41 degrees. The included angle γ is about 46 degrees. Also, in comparison to the septa of FIGS. 20-23, the exterior face 236 is thicker, thereby increasing the surface area contact with the base 102.

Figure 26:
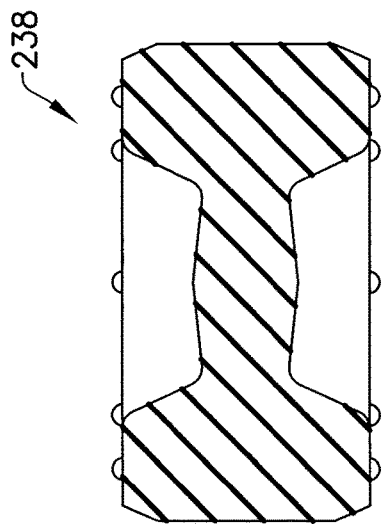
FIGS. 26 and 27 are perspective and cross-sectional views, respectively, of a septum in accordance with an exemplary embodiment of the present invention.
Figure 27:
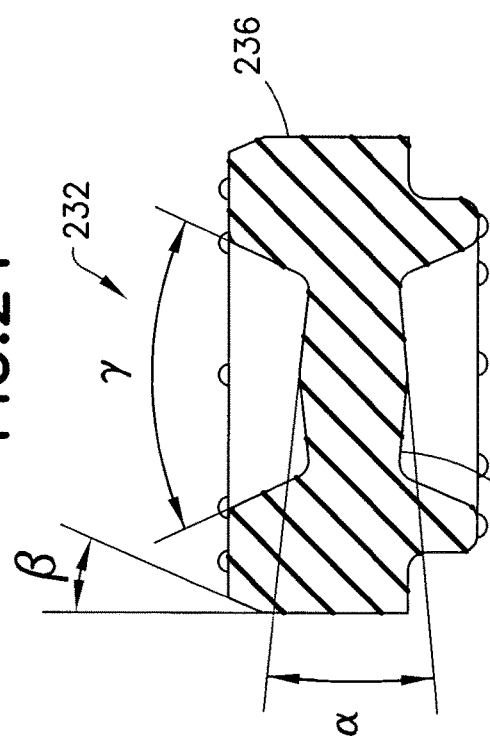

Respectively, FIGS. 26 and 27 are perspective and cross-sectional views of a septum 238 in accordance with another exemplary embodiment of the present invention. The top of septum 238 is substantially similar to the top of septum 232 of FIGS. 24 and 25. The bottom of septum 238, however, is substantially a mirror image of its top. In other words, the septum 238 is substantially symmetrical, both vertically and horizontally.

Figure 28:
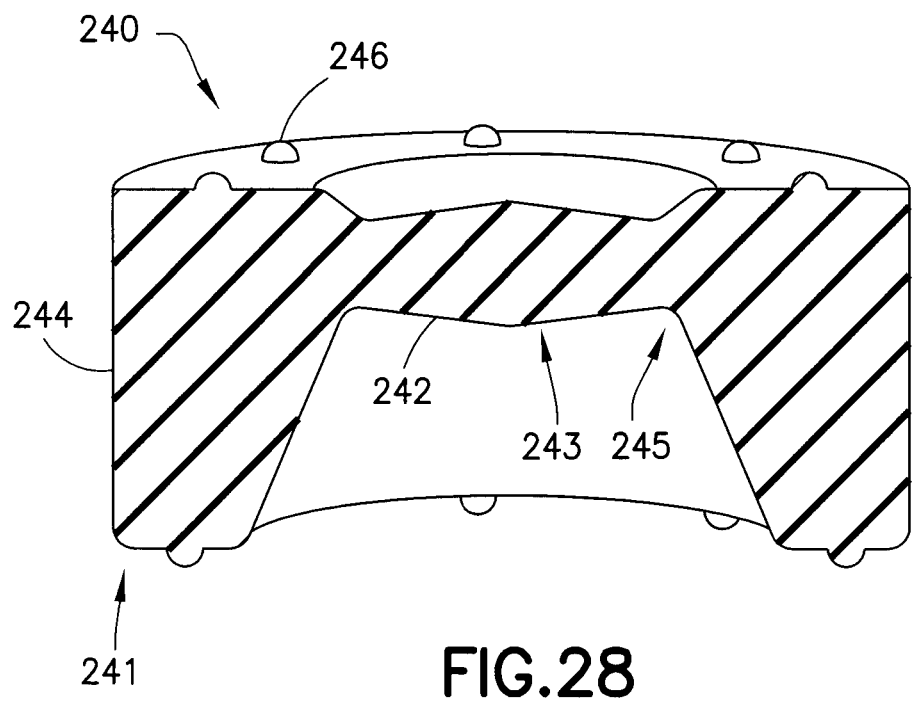
FIGS. 28 and 29 are perspective, cross-sectional vies of respective septa in accordance with exemplary embodiments of the present invention.

As shown in FIG. 28, the septum 240 has a peripheral portion 241 with a substantially straight external side or outer face 244. The peripheral portion 241 is the thickest portion of the septum 240. The peripheral portion 241 surrounds a web portion or central web 242. The web portion 242 has a central portion 243 surrounded by a connecting portion 245 that connects the central portion 243 with the peripheral portion 241. The central portion 243 has a maximum central thickness that is substantially less than the thickness of the peripheral portion. Additionally, the maximum thickness of the central portion 243 is greater than a minimum thickness of the connecting portion 245.

Similar to the septa of FIGS. 24-27, the septum 240 of FIG. 28 has a thicker central web 242 than the septa of FIGS. 20-23. In contrast to those septa, however, the web portion 242 is not located at a vertical center of the septum 240. Instead, the web portion 242 is much closer to the top of the septum 242. According to one embodiment, this promotes sealing with a penetrating blunt cannula. In addition to the positioning of the web 242, in comparison to the septa of FIGS. 24-27, the outer face 244 is substantially straight and vertical. According to one embodiment, however, the outer face 244 can have a slight taper at its ends.

The septum 240 also has at least one nub 246 on its top and at least one nub 246 on its bottom. The plurality of nubs 246 disposed on the top and bottom of the septum 240 can aid manufacturing by helping to keep the septa 240 separate in a container or bin. Additionally, the number of nubs 246 on top of the septum 240 can be different than the number of nubs 246 on the bottom of the septum 240, thus permitting visual inspection (including automated visual inspection) during the assembly process to determine if an asymmetric septum is correctly oriented in the base.

Further, according to one embodiment, during installation of the septum 240 in a base, the septum 240 designed to be radially compressed by about 0.012 inches to 0.018 inches (about 0.305 mm to 0.457 mm). This interference between the septum 240 and the base improves septum seal integrity, both when the fluid connector is attached and when it is detached. Additionally, according to one embodiment, this interference between the septum 240 and the base slightly puckers the web portion 242 to improve re-sealing of the septum 240 when the cannula is removed. Moreover, it is believed that the design of septum 240 provides reliable fluid path connections without the use of a lubricant on the cannula. In addition, according to one embodiment, the design of the septum 240 allows for a height of only about 0.05 inches (1.35 mm), thereby providing the ability to reduce the overall height of the infusion set.

Figure 29:
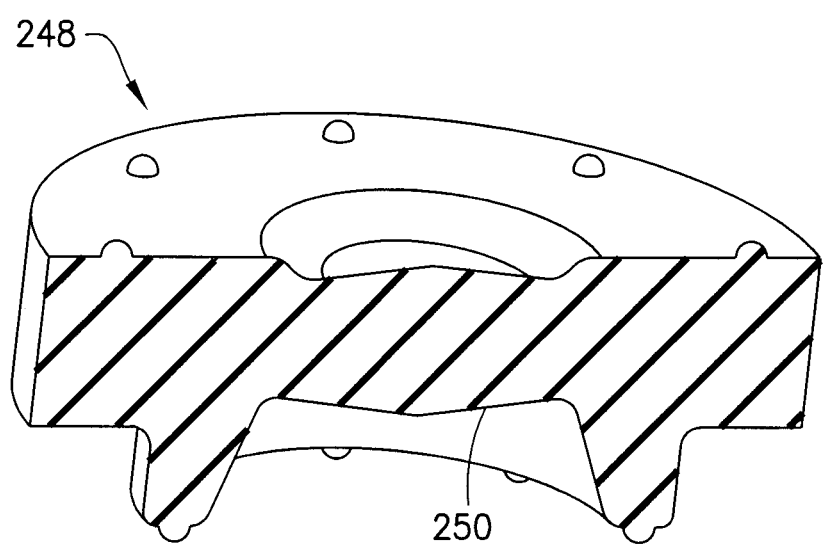

The top of the septum 248 of FIG. 29 is substantially similar to the top of septum 240 of FIG. 28, and the bottom of the septum 248 is substantially similar to the bottom of septum 161 of FIGS. 20 and 21. This results is a slightly thicker central web 250.

The septa of FIGS. 12-29 can be pre-slit. Alternatively, the septa of FIGS. 12-29 can be formed without having a slit. Additionally, the septa of FIGS. 12-29 can be made of silicones, SBR rubber, bromobutyl rubber, and various polyisoprene formulations.

Figure 30:
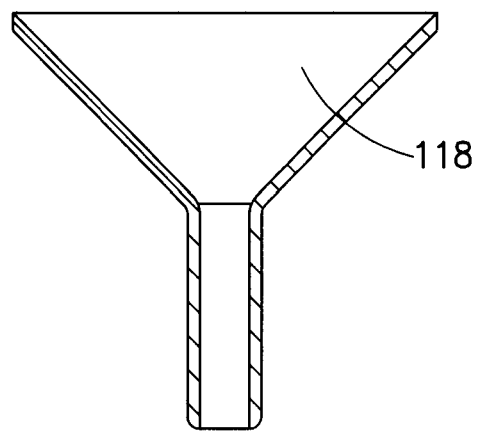
FIG. 30 is a cross-sectional view of a wedge used with the base of FIG. 5 in accordance with an exemplary embodiment of the present invention.

FIG. 30 illustrates the metal wedge 118 alone. As described above in greater detail, the catheter 108 fits over the small diameter of the wedge 118 and both components are then inserted into the receiving cavity 116 in the base 102. According to one embodiment, the catheter 108 is held in place through a press-fit between these three components. Some catheter material may bunch up during assembly into the base 102. Therefore, a receiving space 122 in the base 102 accommodates this extra material so as not to interfere with the desired axial positioning of the wedge 118 when assembled. According to one embodiment, the septum contacts the wedge 118 when installed. According to another embodiment, the septum does not contract 118 when installed.

Figure 31:
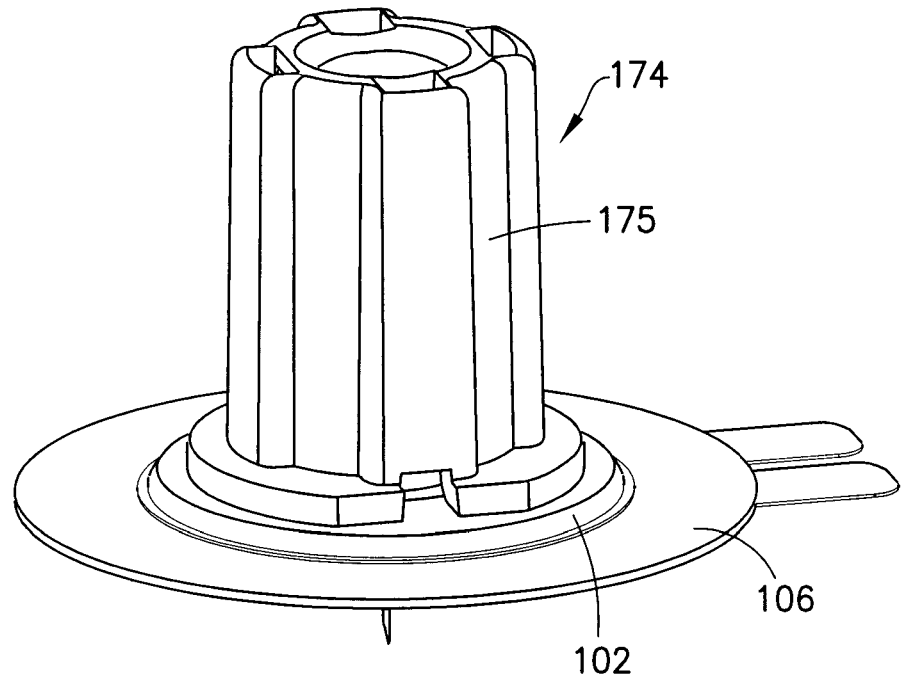
FIG. 31 is a perspective view of a needle shield device in accordance with an exemplary embodiment of the present invention.
Figure 32:
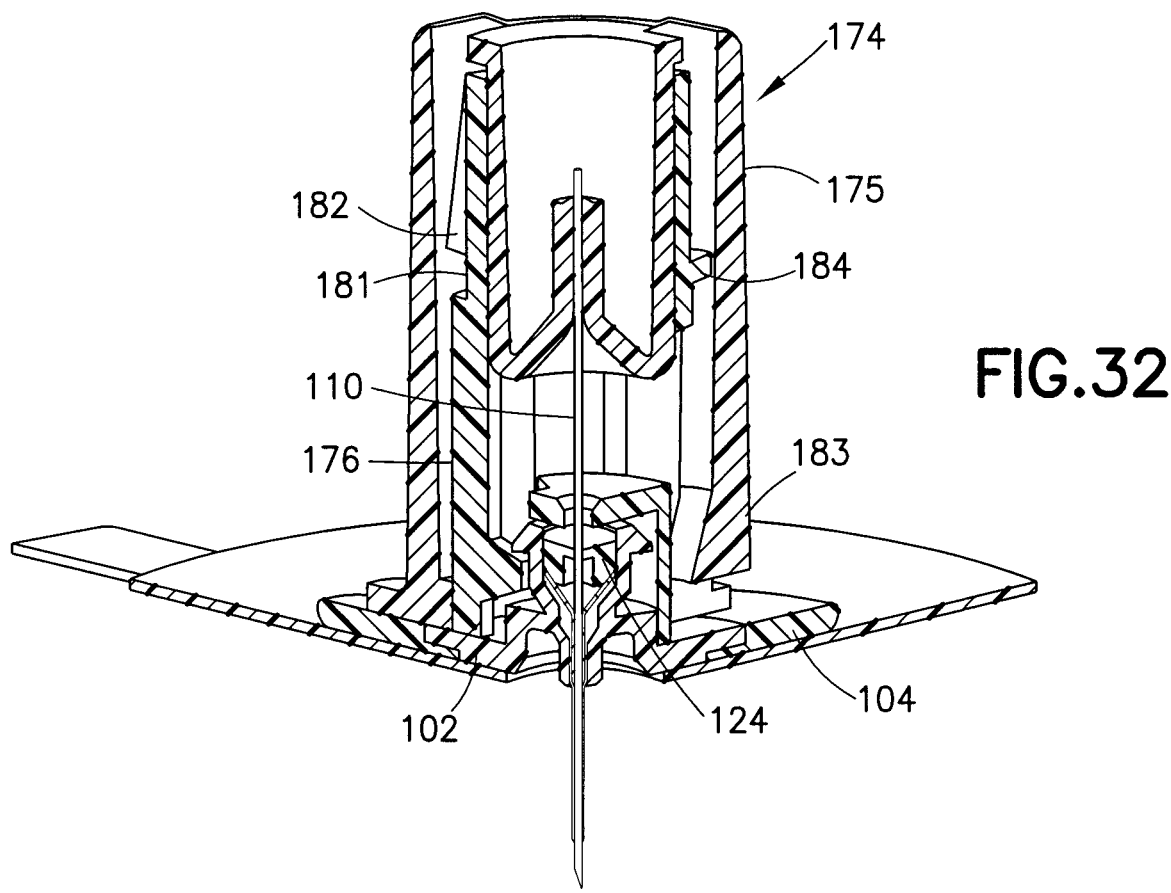
FIGS. 32-36 are perspective cross-sectional views illustrating operation of the needle shield device of FIG. 31.

FIG. 31 illustrates a passive needle shield device 174 connected to the base 102 and ready for placement on the skin. FIG. 32 is a cross-sectional view of the needle shield device 174 fully engaged with the base 102, piercing the septum 124 and the catheter 108 with the introducer needle 110. The needle shield device 174 includes a needle hub or outer shield 175 which surrounds and encloses an inner shield 176 and the introducer needle 110.

FIGS. 33-36 illustrate the sequence of steps that occur after the user has inserted the catheter 108. In other words, these figures illustrate the operation of removing the needle shield device 174 from the base 102. Briefly, the user simply pulls on the outer shield 175 in a direction away from the base 102 to remove the introducer needle 110. According to one embodiment, the outer shield 175 and inner shield 176 are both made of rigid plastic materials that have some degree of flexibility.

Figure 33:
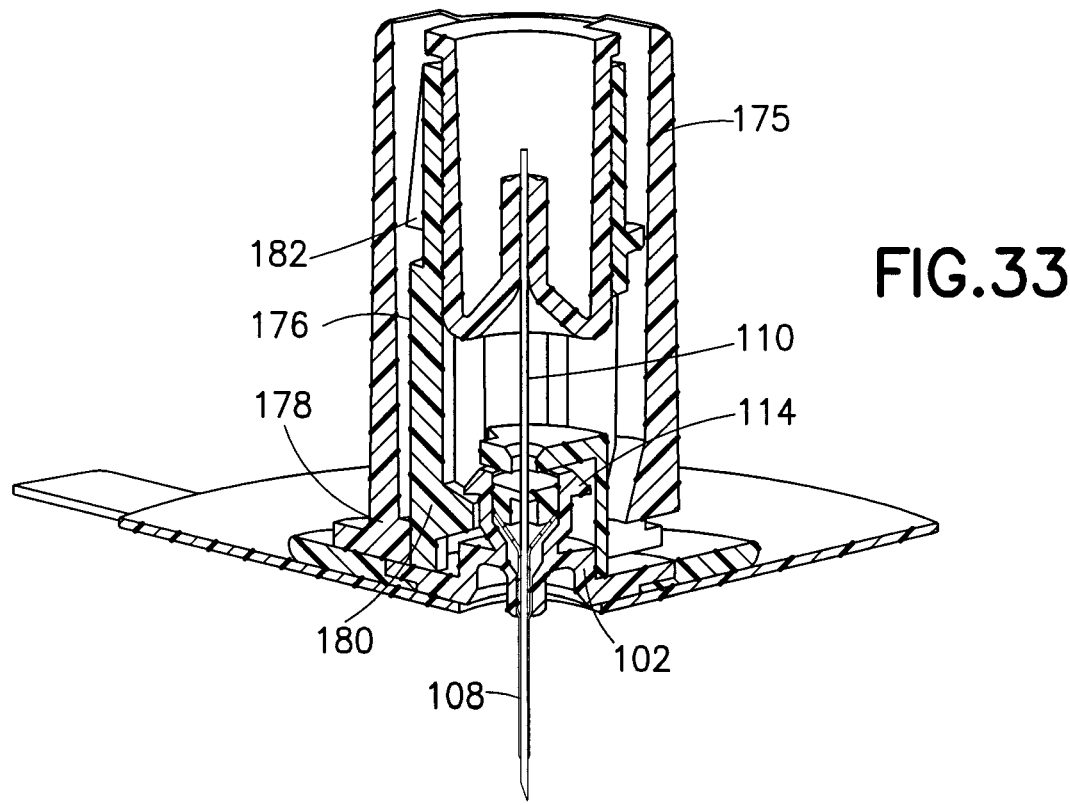

In more detail, FIG. 33 is a quarter-sectional view illustrating an initial state of the needle shield device 174 and a first position of the outer shield 175 relative to the inner shield 176, in which an outer shield hub latch 178 contacts the base 102 and also contacts a cantilevered latch beam 180 of the inner shield 174 to maintain engagement of the latch beam 180 with the base 102 beneath the base latch 114. According to one embodiment, the hub latch 178 biases the latch beam 180 radially inward.

Figure 34:
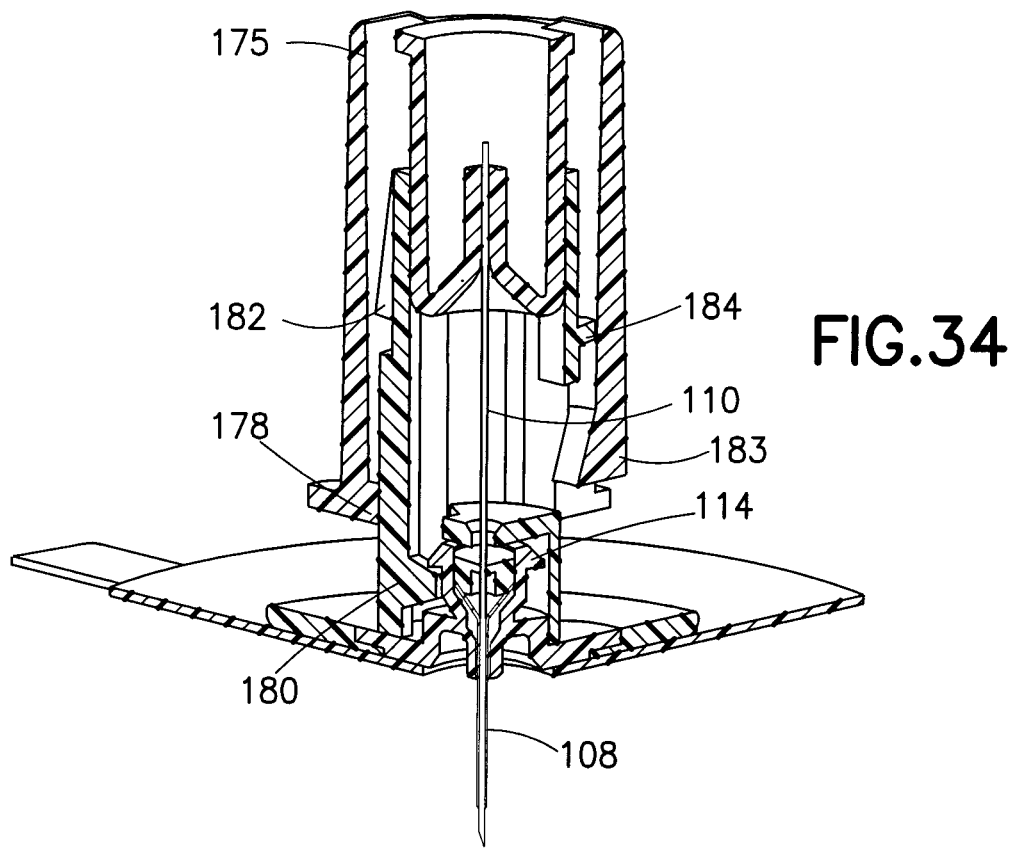

FIG. 34 illustrates the orientation of the needle shield device 174 while the user is axially displacing the outer shield 175, but before it has completed its stroke relative to the inner shield 176. In this state, the outer shield 175 continues to prevent the latch beam 180 from disengaging from the base 102. More specifically it is the hub latch 178 that holds the latch beam 180 in place against the base 102. Therefore, according to one embodiment, the inner shield 176 is locked onto the base 102 while the outer shield 175 is being axially displaced relative to the inner shield 176.

Figure 35:
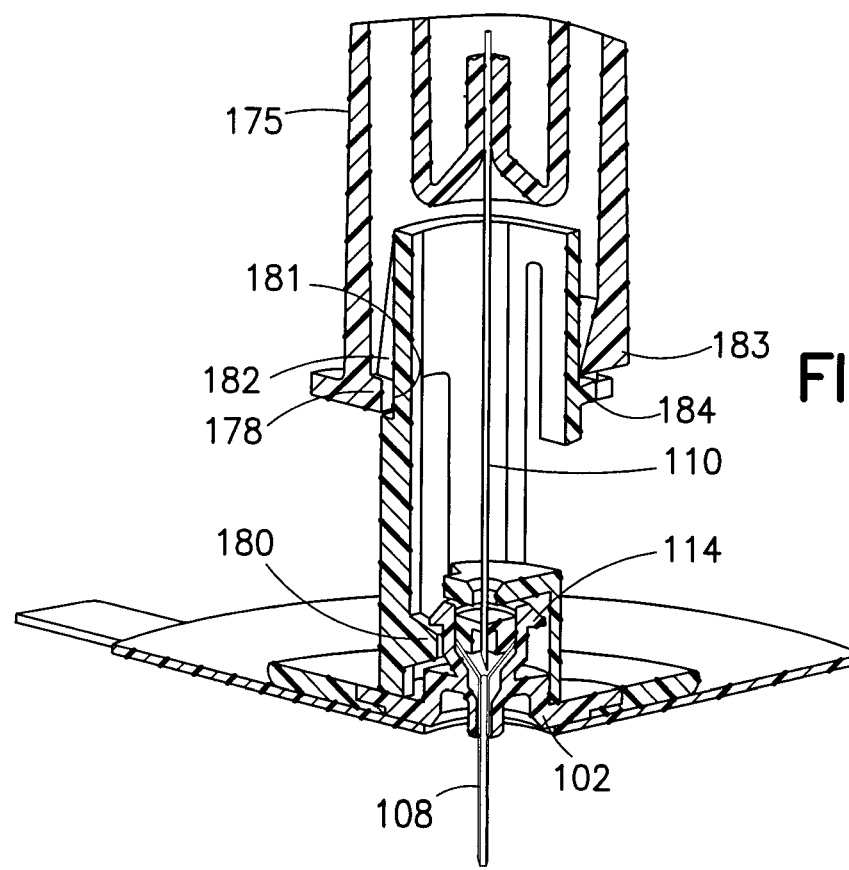

FIG. 35 illustrates the completely displaced position of the outer shield 175 with respect to the inner shield 176. In this state, the hub latch 178 no longer prevents the latch beam 180 from disengaging from the base 102. The hub latch 178 is instead disposed in an indent 181 (best shown in FIG. 32) on the inner shield 176 and engaged with a shield latch 182 formed on the inner shield 176. The shield latch 182 engages a top side of the hub latch 178, thereby preventing further proximal displacement of the outer shield 175 relative to the inner shield 176. Additionally, because the hub latch 178 is no longer pressing on the latch beam 180, the latch beam 180 can disengage from the base 102.

Further, a hub beam or outer shield latch 183 rides over an inner shield latch 184 and the bottom of the hub beam 183 engages the top of the inner shield latch 184 to prevent distal displacement of the outer shield 175 relative to the inner shield 176. According to one embodiment, the hub beam 183 is cantilevered.

The latch beam 180 is free to radially displace and disengage from the base 102 once the user continues to distally displace the needle shield device 174. The engagement of the shield latch 182 with the hub latch 178 and the engagement of the hub beam 183 with the inner shield latch 184 shields the introducer needle 110 and thereby reduces the possibility of an accidental needle stick.

According to one embodiment, the inner shield latch 184 is fixedly disposed on the inner shield 176. According to another embodiment, the inner shield latch 184 is disposed on a cantilevered inner shield latch beam 416 so that both the inner shield latch beam 416 and the hub beam 183 are cantilevered. According to yet another embodiment, the inner shield latch 184 is disposed on a cantilevered inner shield latch beam 416 and the hub beam is fixedly disposed on the outer shield 175.

In another alternative embodiment, the needle shield device 174 can also be attached to a fluid connector 126 and the base 102. Such an embodiment allows a user to prime the infusion set while it is outside the body and insert and remove the introducer needle 110 with the fluid connector 126 attached the entire time.

Figure 36:
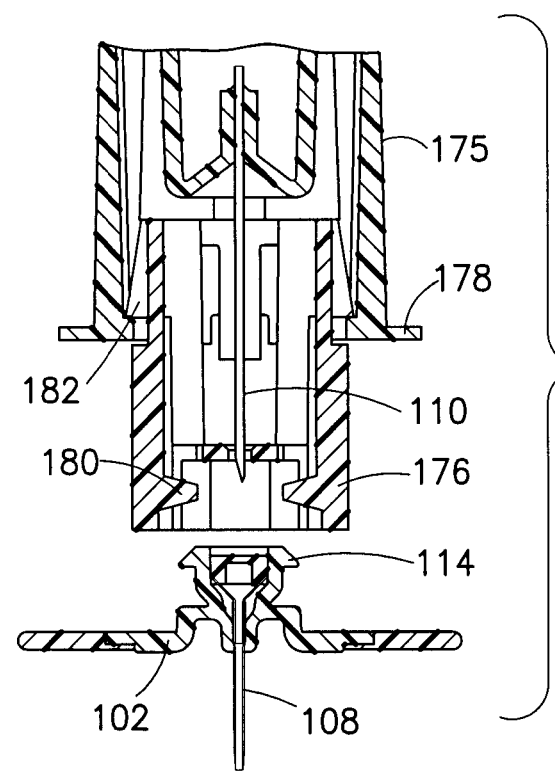

FIG. 36 illustrates a completely deployed needle shield device 174. The latch beam 180 is removed from the base 102 as the user continues to pull on the outer shield 175.

Figure 37:
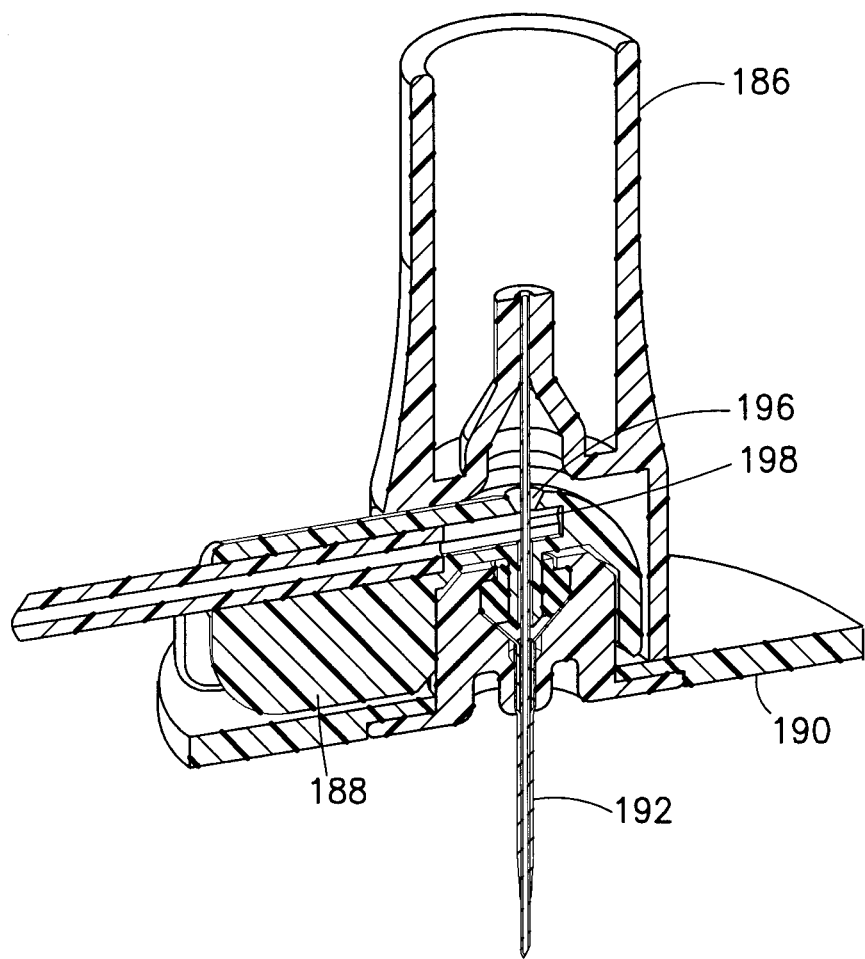
FIG. 37 is a perspective and cross-sectional view of an infusion device with an introducer needle hub in accordance with an exemplary embodiment of the present invention.

In accordance with another embodiment of the present invention, FIG. 37 illustrates an infusion device with an introducer needle hub 186 that is ready for insertion into the skin of a user. FIG. 37 is a cross-sectional view of the introducer needle hub 186, a fluid connector 188, and a base 190. Although the introducer needle hub 186 secures and introduces an introducer needle 192 in substantially the same way as the introducer needle hub 100 of FIG. 1, the introducer needle hub 186 is configured to engage the fluid connector or fluid connector hub 188 and introduce the introducer needle 192 through the fluid connector 188 before penetrating the base 190. The introducer needle hub 186 includes a fluid connector slot 194 that receives a portion of the fluid connector 188 extending away from the base 190. The fluid connector 188 also differs from the previously disclosed fluid connector 126 of FIG. 7 in that the top surface of the fluid connector 188 includes an aperture 196 for receiving the introducer needle 192. Additionally, to maintain a sealed fluid path, a second septum (a first septum being located in the base) is secured in a cavity 198 immediately adjacent to the aperture. The arrangement shown in FIG. 37 allows the infusion set to be inserted into the user's skin with the fluid connector already connected to the base.

Figure 38:
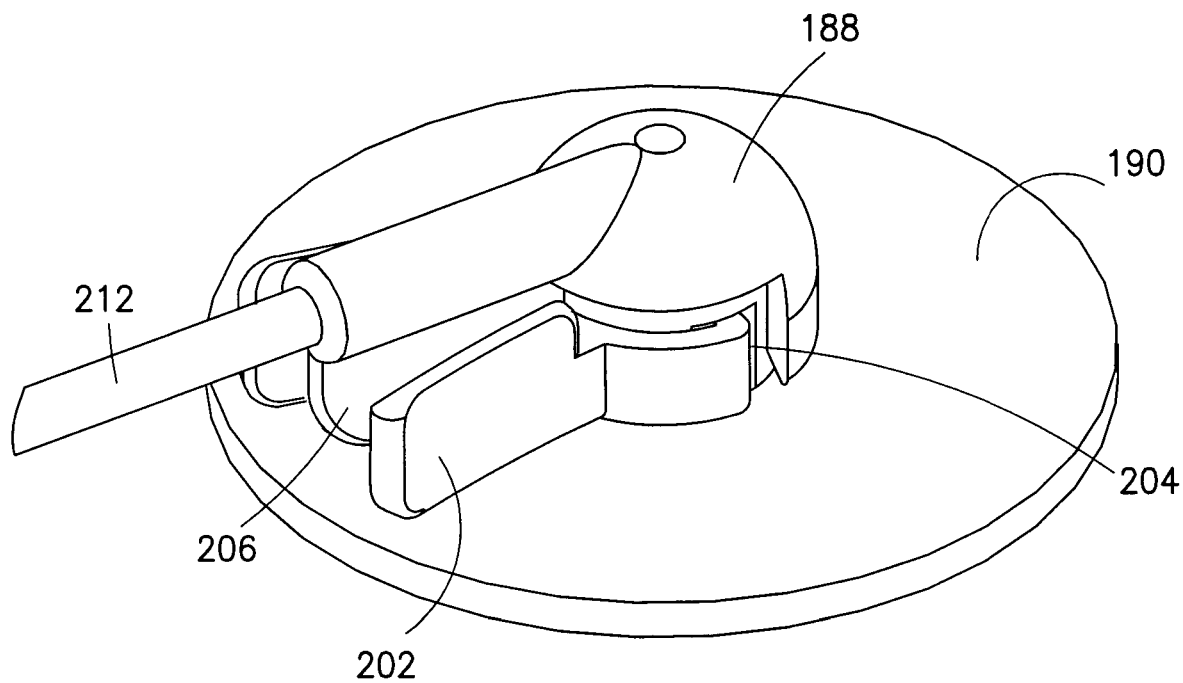
FIG. 38 is a perspective view of a fluid connector and base fully engaged in accordance with an exemplary embodiment of the present invention.

FIG. 38 illustrates the fluid connector 188 and base 190 fully engaged. The fluid connector 188 includes activation levers 202, fluid connector latches 204, and a rigid stop 206, each made of plastic and functioning similarly to the corresponding parts of the previously described embodiment. In contrast to the previously described fluid connector 126 of FIG. 7, however, in this particular embodiment, the activation levers 202 and the fluid connector latches 204 are molded as part of the fluid connector 188 and pivot about a living hinge. This single-piece fluid connector configuration can be utilized to simplify manufacturing. The rigid stop 206, as disclosed in the previously described embodiment, ensures that both of the fluid connector latches 204 travel far enough to completely disengage, and provides a stable anchor for the activation levers 202 during the handling of the fluid connector 188.

Figure 39:
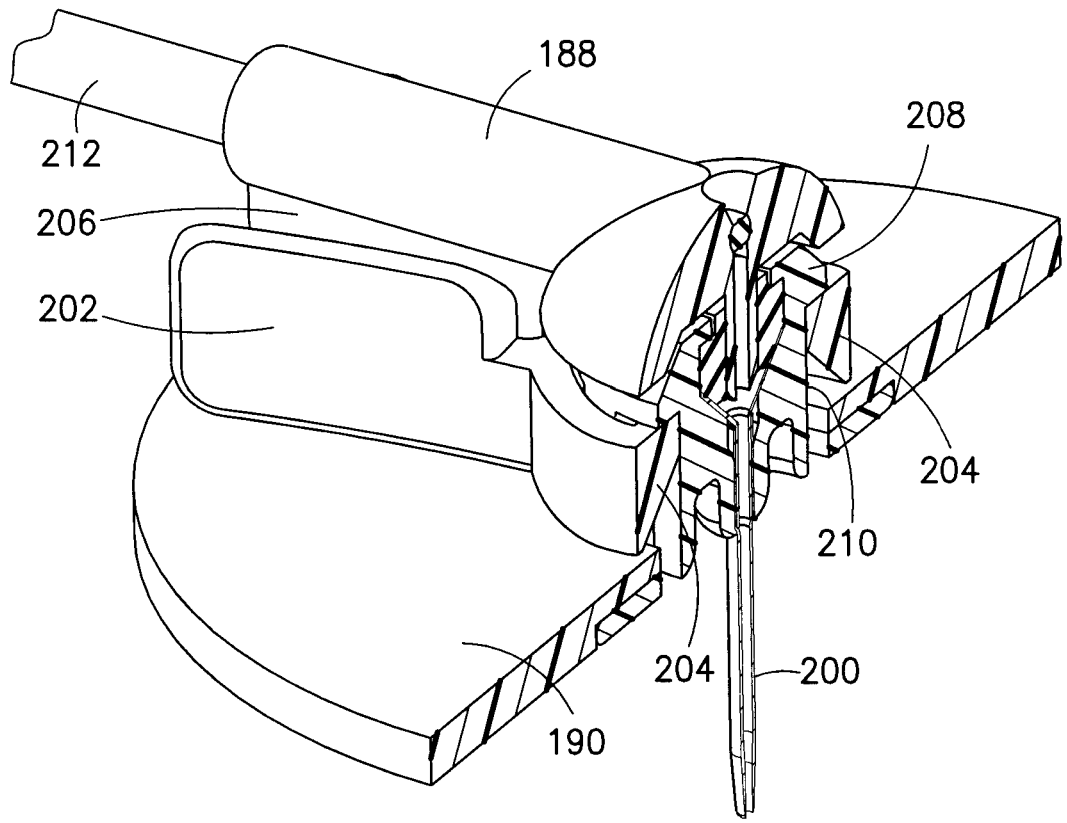
FIGS. 39-41 illustrate latching between the fluid connector and base latches of FIG. 38.
Figure 40:
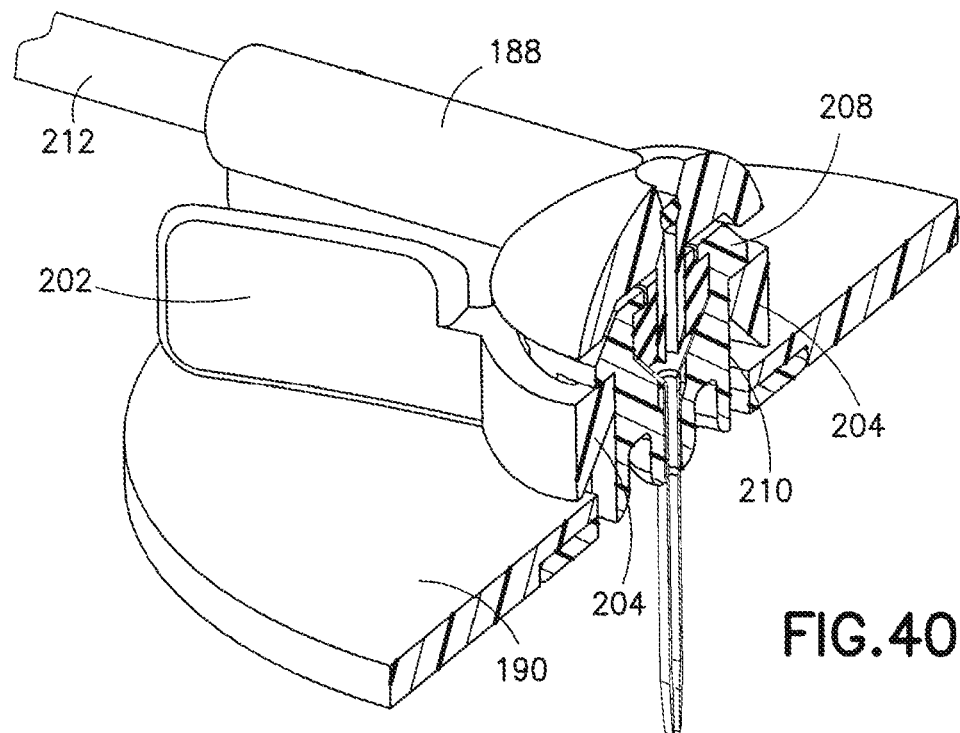
Figure 41:
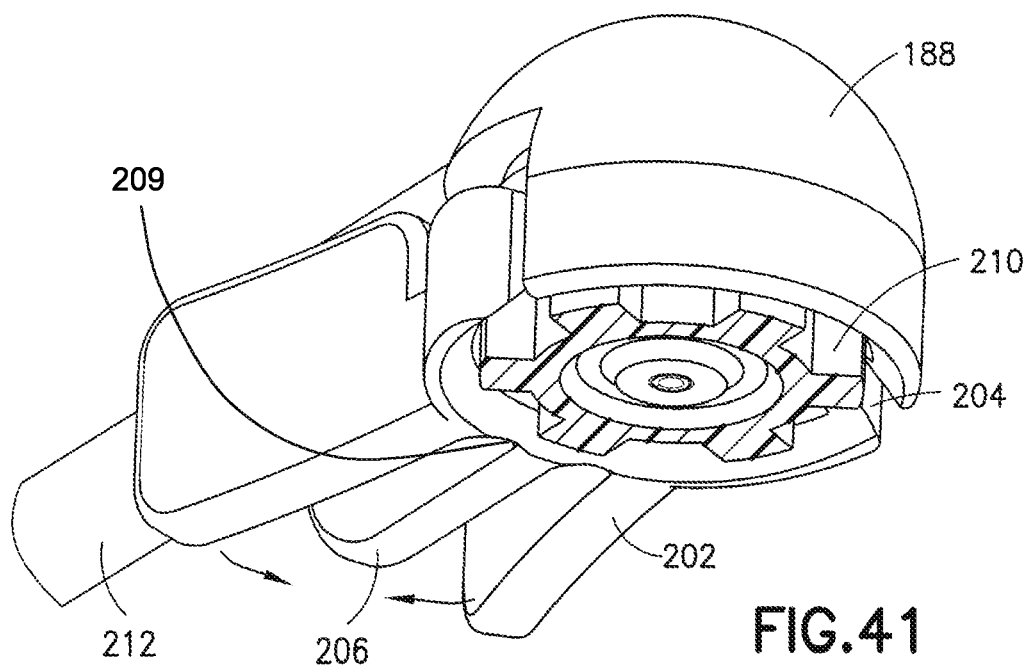
Figure 42:
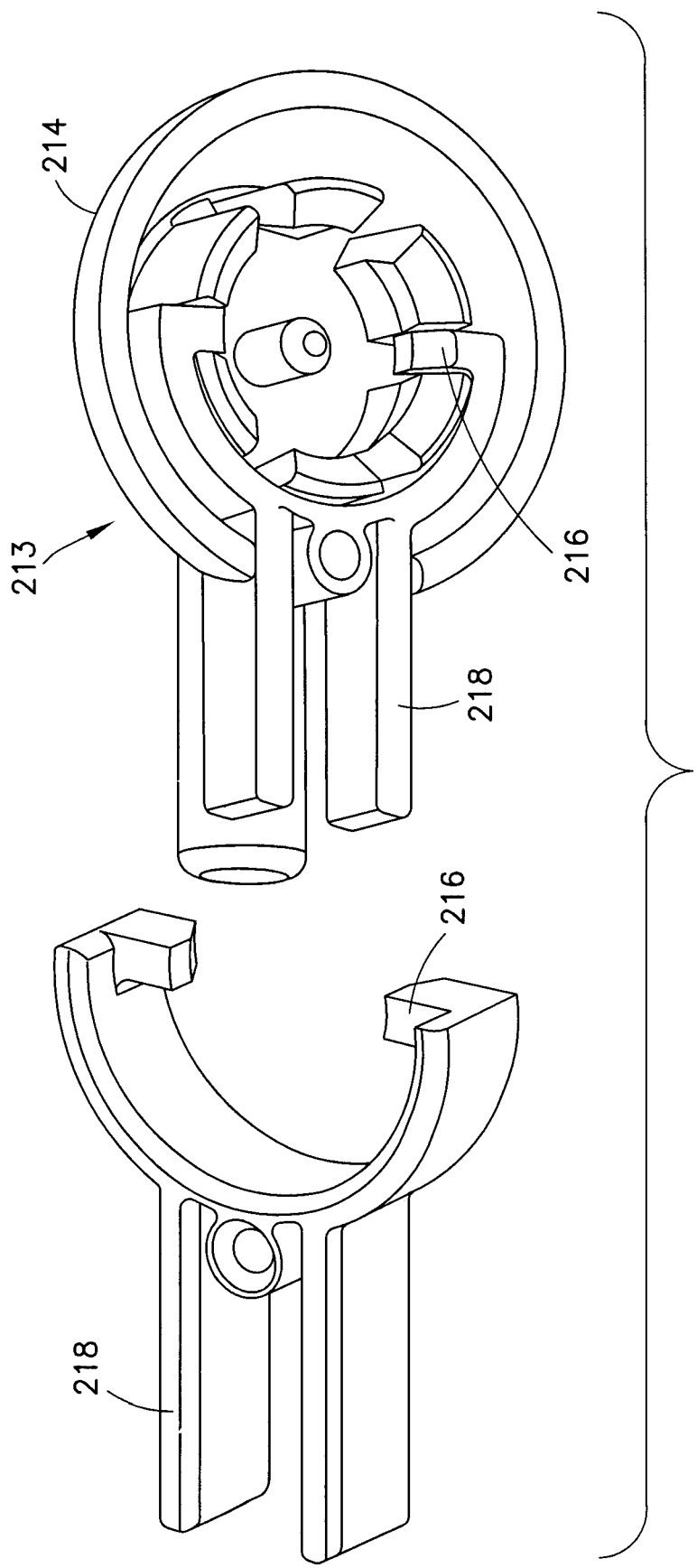
FIGS. 42-44 illustrate components of a fluid connector, fluid connector latches, and activation levers in accordance with an exemplary embodiment of the present invention.
Figure 43:
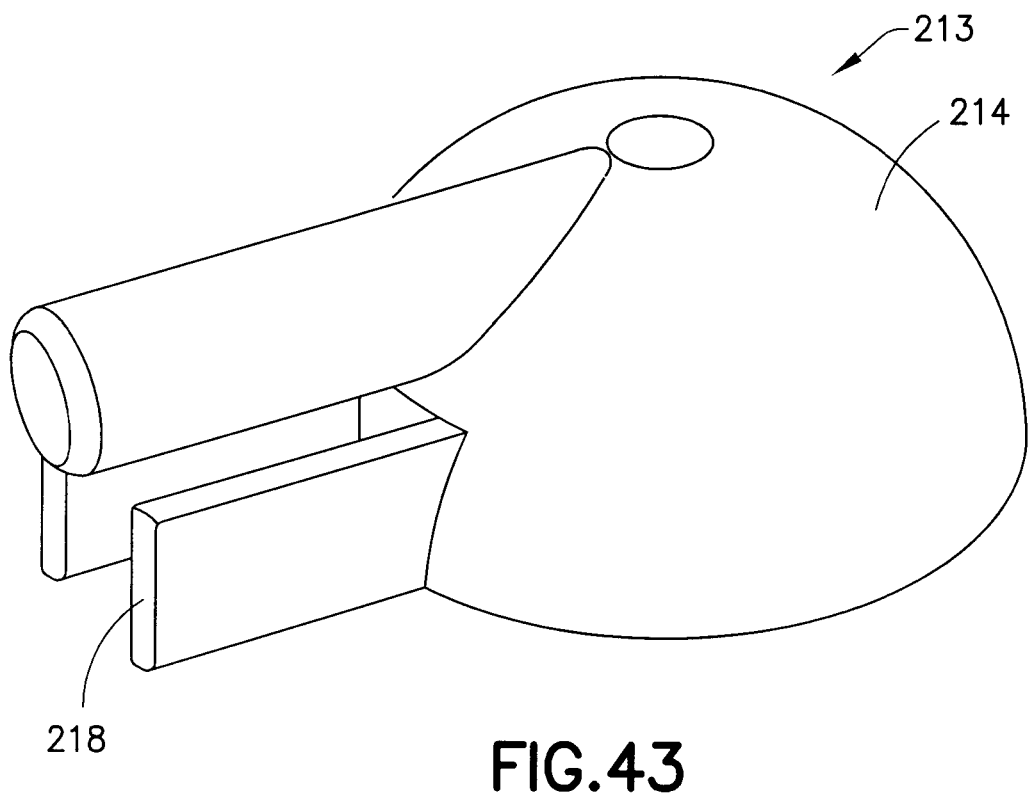
Figure 44:
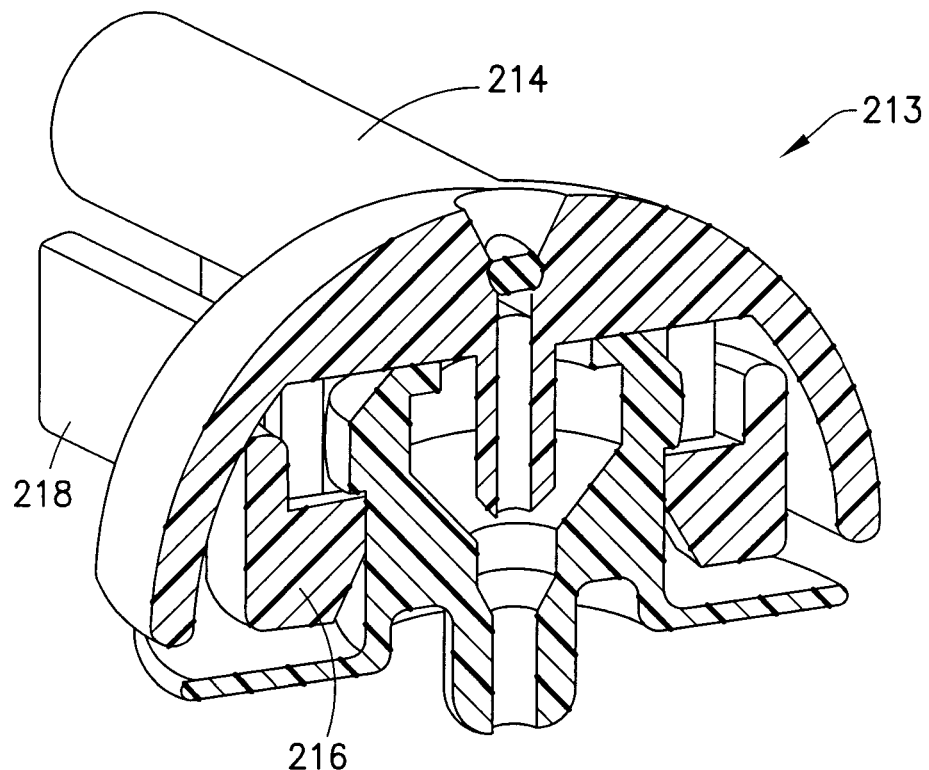

FIGS. 39-41 illustrate how the fluid connector latches 204 mate with the base latches 208. In this exemplary embodiment, the fluid connector 188 is latched against rotation with respect to the base 190. The rotation prevention is facilitated by the fluid connector latches 204 dropping into corresponding base latch slots 210 provided on the column of the base 190. For clarity, only a portion of the base 190 is shown in FIGS. 39-41. During connection of the fluid connector 188 to the base 190, but before full engagement, the user can rotate an extension tubing 212 and the fluid connector 188 so that fluid connector 188 can be conveniently attached to the infusion pump. If the fluid connector latches 204 do not immediately drop into the base latch slots 210, slight rotation of the fluid connector 188 can enable the fluid connector latches 204 to drop into position, thereby locking the fluid connector 188 against removal and further rotation.

If it becomes necessary or desirable to rotate the fluid connector 188 and the extension tubing 212, the user simply presses the activation levers 202 together (as shown in FIG. 41) to disengage the fluid connector latches 204 from the base latch slots 210. Then, the user repositions the fluid connector 188 to a more desirable rotational or circumferential position, and releases the activation levers 202 to lock the fluid connector latches 204 into the corresponding base latch slots 210. FIG. 41 also illustrates a living hinge 209 upon which the fluid connector latches 204 and activation levers 202 rotate.

In contrast to the embodiment illustrated in FIGS. 39-41, FIGS. 42-44 illustrate another embodiment of a fluid connector 213 that includes two molded plastic components that comprise the fluid connector cover 214, fluid connector latches 216 and activation levers 218. Although this embodiment includes two separately molded components, the fluid connector cover 214, fluid connector latches 216, and activation levers 218 function in much the same way as the respective components illustrated in the embodiment illustrated in FIGS. 39-41. The two molded plastic components may be utilized, in contrast to a single molded component, for cosmetics or to simplify manufacturing.

FIGS. 45-55 disclose multiple embodiments of release liner slit designs for peeling the adhesive backing off of an adhesive patch connected to an infusion device. Each of the embodiments avoids potential contact of the release liner with the needle and/or catheter penetrating the center of the release liner.

Figure 45:
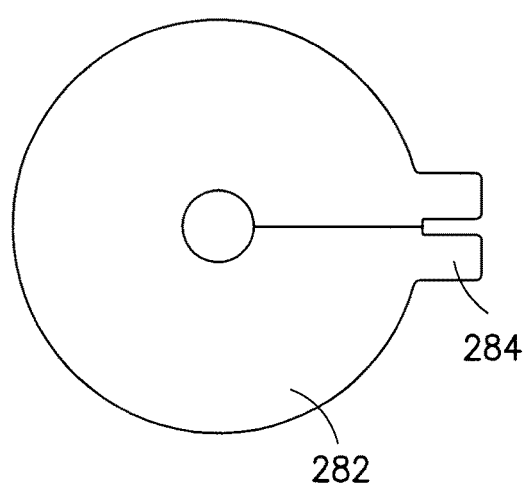
FIGS. 45-55 illustrate release liner slit designs for peeling the adhesive backing off of an adhesive patch connected to an infusion device in accordance with another exemplary embodiment of the present invention.
Figure 46:
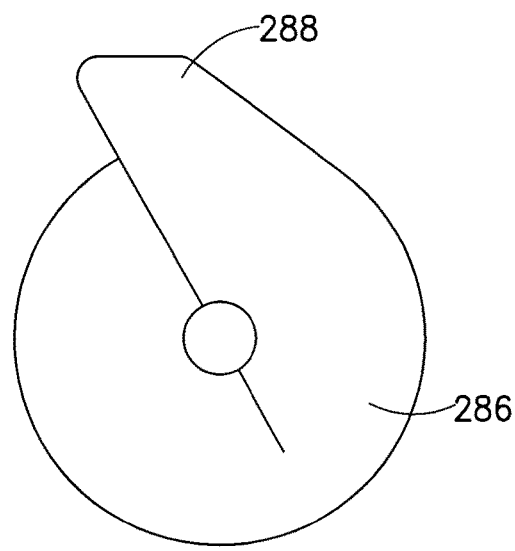
Figure 47:
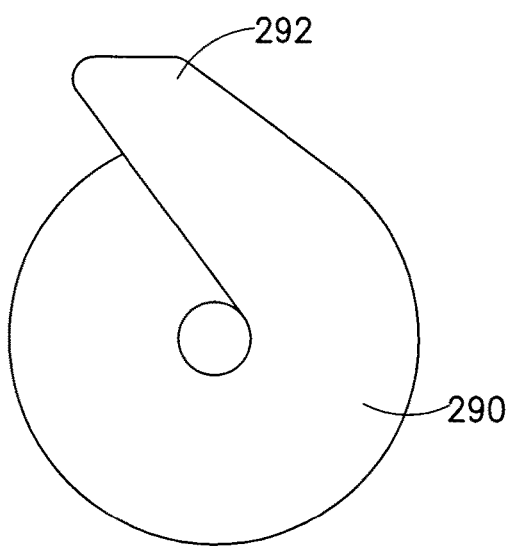
Figure 48:
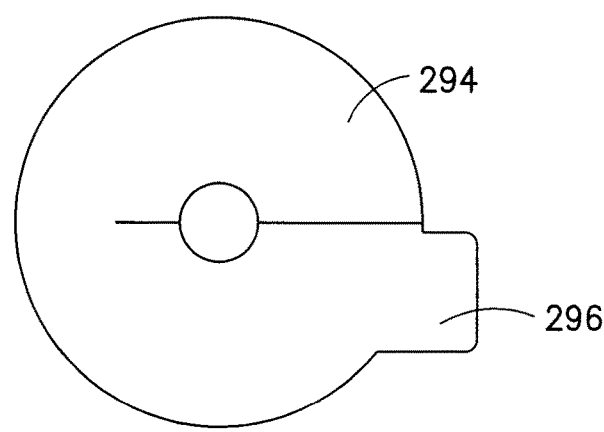
Figure 49:
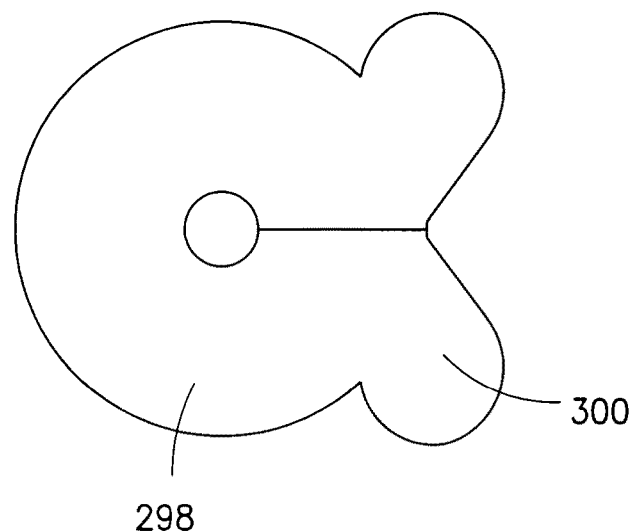
Figure 50:
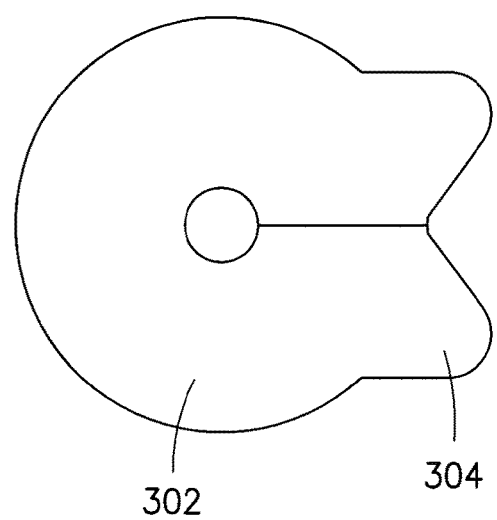
Figure 51:
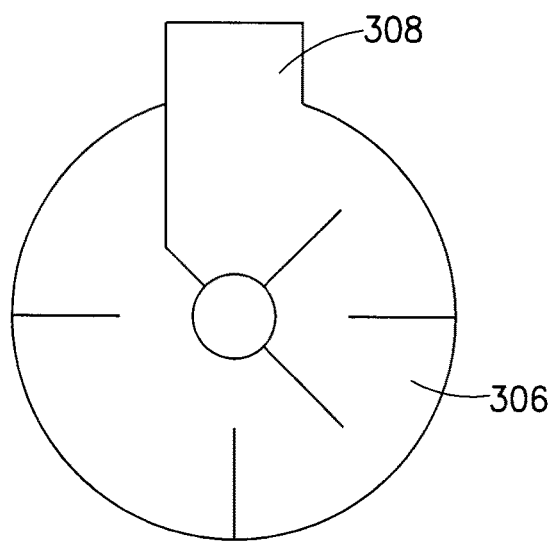
Figure 52:
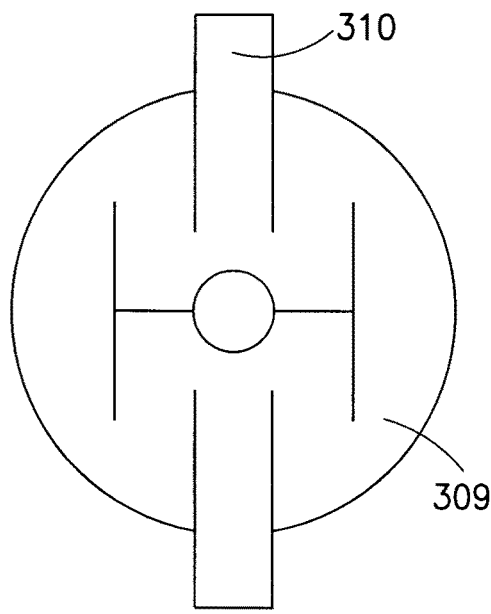
Figure 53:
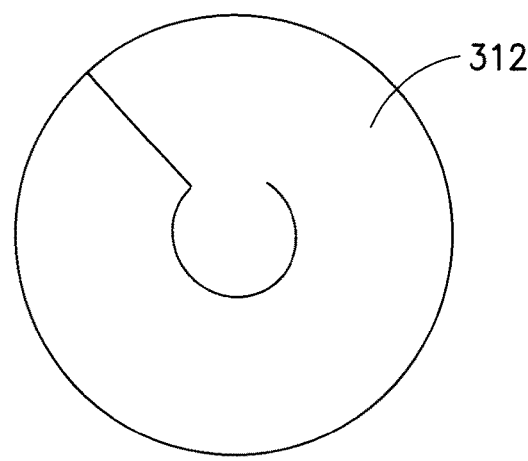
Figure 54:
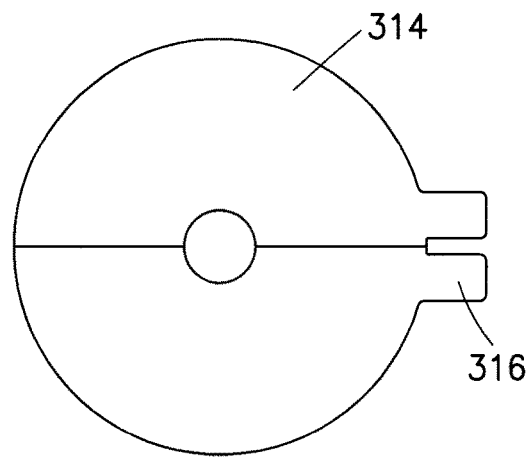
Figure 55:
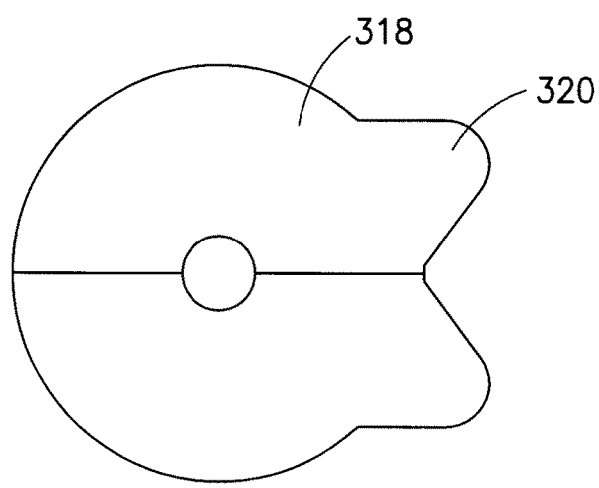

FIG. 45 illustrates a first release liner embodiment 282 formed from a single piece and having two pull tabs 284. In contrast, FIG. 46 illustrates a second release liner embodiment 286 formed from a single piece and having single pull tab 288 and an extended slit. Similarly, FIG. 47 illustrates a third release liner embodiment 290 formed from a single piece and having a single pull tab 292 and an off-center slit. FIG. 48 illustrates a fourth release liner embodiment 294 formed from a single piece and having a single pull tab 296 with an extended slit. FIG. 49 illustrates a fifth release liner embodiment 298 formed from a single piece and having two pull tabs 300 extending substantially 90 degrees from the center slit. FIG. 50 illustrates a sixth release liner embodiment 302 formed from a single piece and having two pull tabs 304 extending substantially parallel with the center slit. FIG. 51 illustrates a seventh release liner embodiment 306 formed from a single piece and having a single pull tab 308 and multiple slits. FIG. 52 illustrates an eighth release liner embodiment 309 formed from a single piece and having multiple slits and two pull tabs 310 extending from opposite sides of the release liner and multiple slits. FIG. 53 illustrates a ninth release liner embodiment 312 formed from a single piece, and having no extending tabs and only a single slit. FIG. 54 illustrates a tenth release liner embodiment 314 formed from two pieces and having two pull tabs 316. FIG. 55 illustrates an eleventh release liner embodiment 318 formed from two pieces and having two pull tabs 320 extending substantially parallel to the slit separating the two pieces.

According to one embodiment, the flexible disc base (for example, base 102) can be perforated to increase moisture and air permeability and increase patient comfort. In another embodiment skin adhesive material can be coated directly onto the base, eliminating the need for a separate adhesive patch. In yet another embodiment, the adhesive patch can be made from either non-woven or woven adhesive-backed material.

Figure 56:
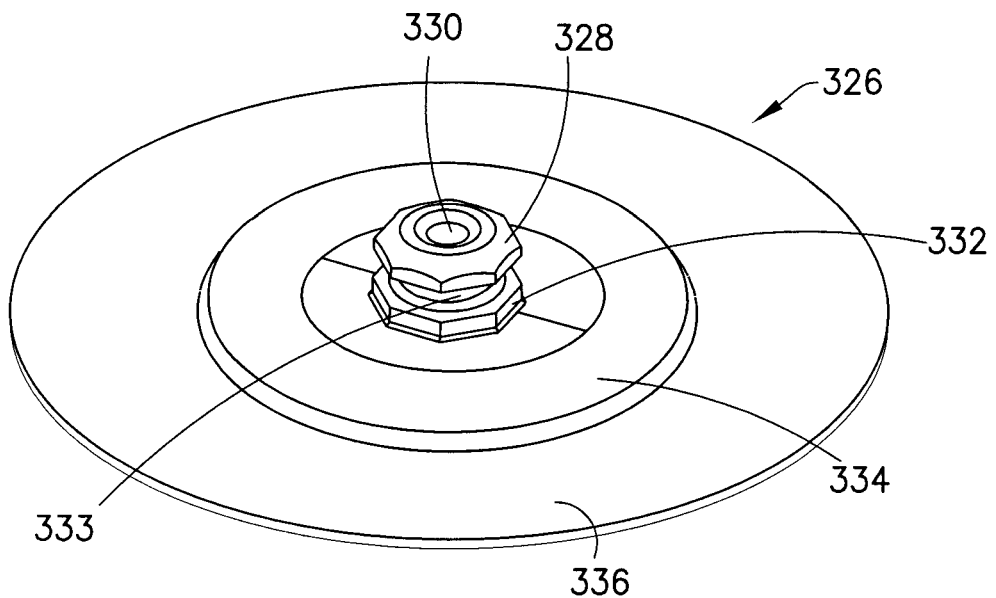
FIG. 56 is a perspective view of a base in accordance with an exemplary embodiment of the present invention.
Figure 58:
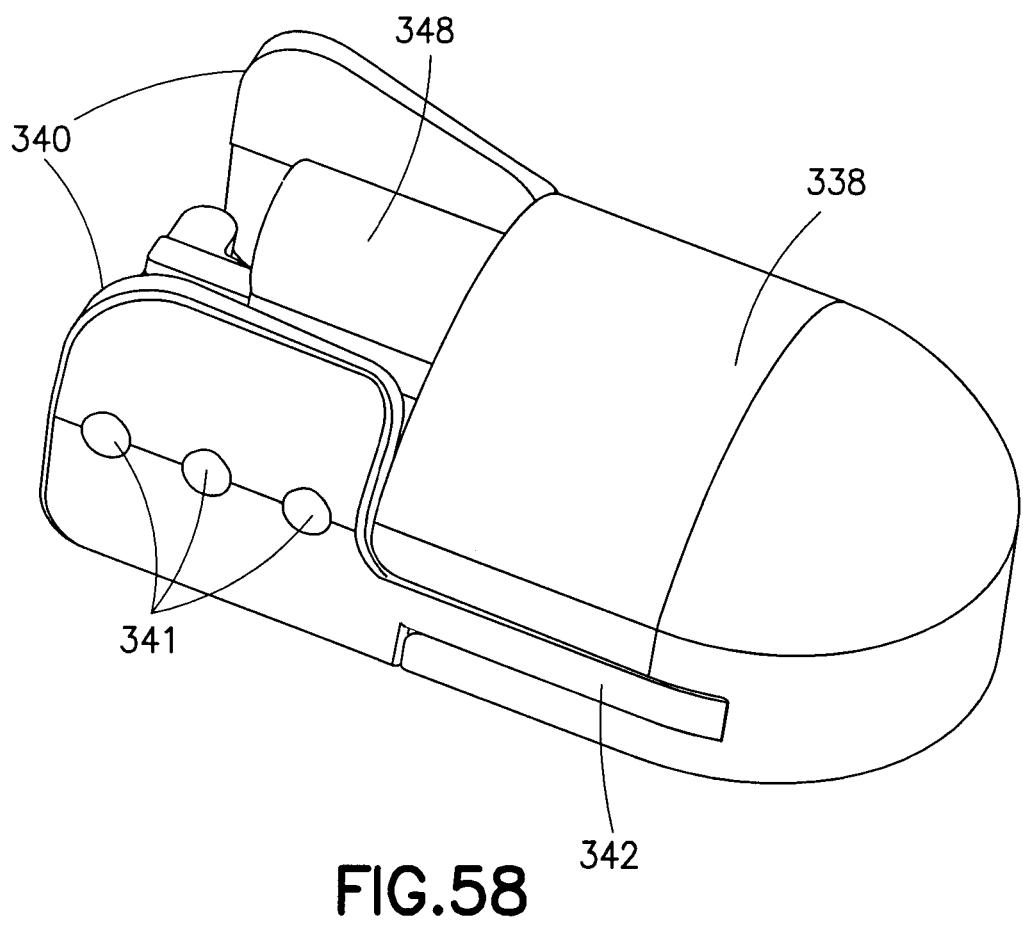
FIG. 58 is an assembled perspective view of the fluid connector of FIG. 57.
Figure 57:
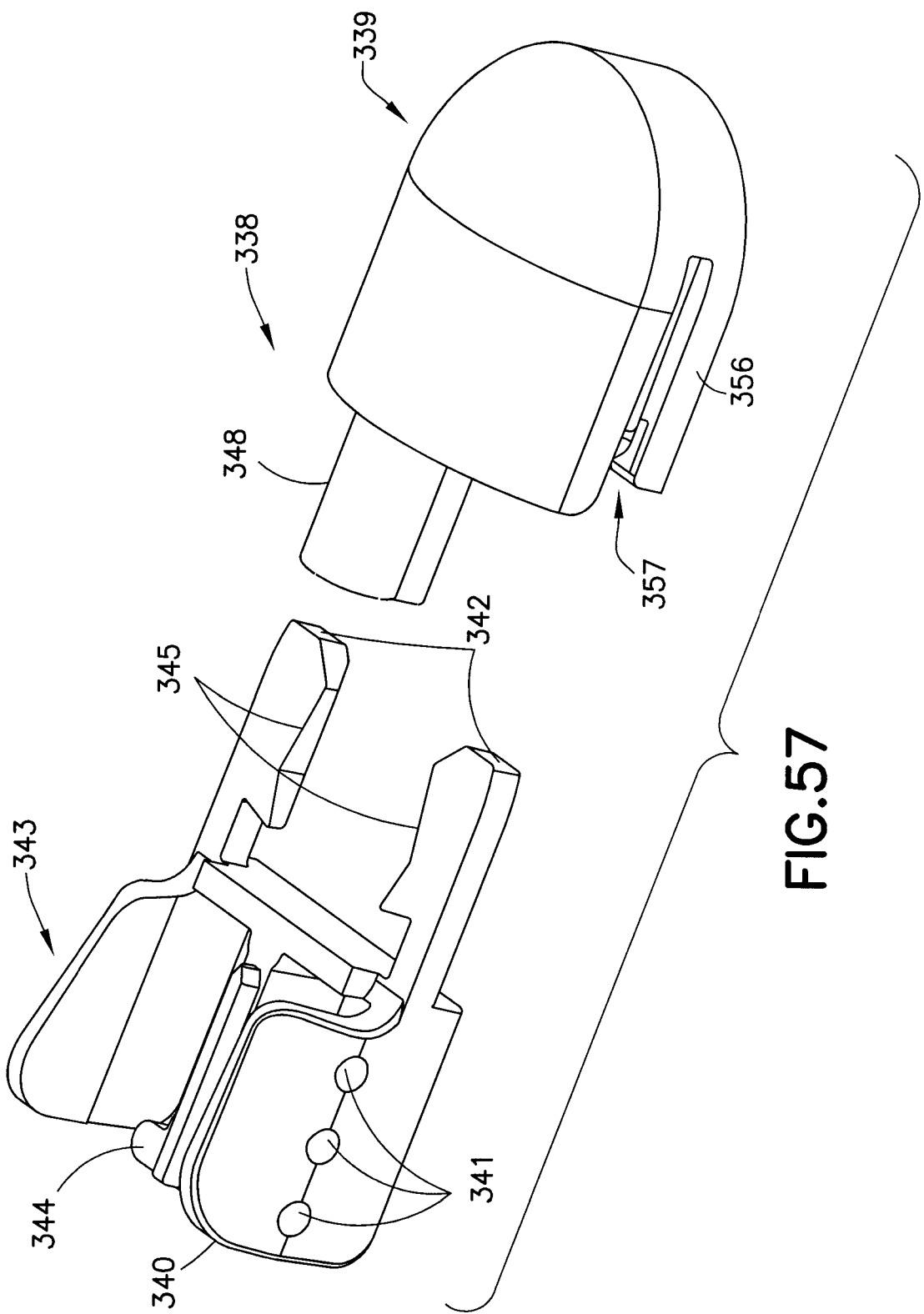
FIG. 57 is an exploded, perspective view of a fluid connector in accordance with an exemplary embodiment of the present invention.

FIG. 56 illustrates features of an exemplary embodiment of a base 326. The base 326 includes a base latch 328 surrounding an internal cavity 330. As illustrated, the base latch 328 is formed in an octagonal shape, having eight flat perimeter side surfaces or facets. The base 326 also includes a base section 332 that also includes a plurality of flat side surfaces or facets that correspond to the facets of the base latch 328. The flat side surfaces of the base section 332 are also substantially coplanar with the corresponding flat side surfaces of the base latch 328. Alternatively, the base latch 328 and base section 332 can each be formed having any number of side surfaces, each corresponding to a discrete rotational or circumferential position. For example, the base latch 328 and the base section 332 can have three facets. According to another embodiment, the base latch 328 can have eight or more facets. According to another embodiment, the base latch 328 and the base section 332 can have eight or more facets.

Disposed between the base latch 328 and the base section 332 is a latching portion 333 having a reduced diameter compared to the base latch 328 and the base section 332. According to one embodiment, the latching portion 333 is a substantially cylindrical column.

According to one embodiment, the base 326 engages a flexible disc 334 positioned between the base 326 and the user. The flexible disc 334 moves with the user during physical activity while minimizing contact of the rigid portions of the base 326 with the user. The flexible disc 334 can be attached to an adhesive patch 336 having an adhesive backing, which can be used to secure the base 326 to the user's skin.

FIGS. 57-63 illustrate another exemplary embodiment of a fluid connector 338. In comparison to previously-described fluid connectors, this exemplary embodiment reduces the overall height and profile of the fluid connector 338, thus reducing interference and potential irritation to the user. The fluid connector 338 includes two components: a fluid path portion 339, and a latching portion 343. The latching portion 343 includes activation levers 340, fluid connector latches 342, and a rigid stop 344.

According to one embodiment, the activation levers 340, fluid connector latches 342, and the rigid stop 344 are integrally formed as a unitary structure. Additionally, the activation levers 340 form arms with their respective fluid connector latches 342. These arms are displaceable relative to the fluid path portion. The fluid connector latches 342 are displaceable to a latching position in which the at least a portion of he fluid connector latch 342 is disposed within the fluid path portion 339. Further, the arms are resiliently biased toward the latching position.

The fluid path portion 339 includes a tubing connector portion 348 for connecting the fluid connector 338 with tubing. The fluid path portion 339 can be secured to the latching portion 343 via snap-fit engagement and in according to one embodiment, the fluid path portion 339 and the latching portion can be made of the same material.

The user attaches the fluid connector 338 to the base 326 by pressing distally (down), incrementally forcing the fluid connector latches 342 outward, and snapping it in place, due to the inward resilient bias of the fluid connector latches 342. The user can also attach the fluid connector 338 to the base 326 by pressing the activation levers 340 together until they engage the rigid stop 344, and then pressing the distally until internal facets in the fluid path portion 339 engage the base latch 328 and the base portion 332, as subsequently described in greater detail. Then, the user releases the fluid connector latches 342 so they snap and engage the latching portion 333 and the underside of the base latch 328 to resist proximal displacement of the fluid connector. Once engaged, the user may remove his or her fingers from the activation levers 340, and the fluid connector 338 will be securely latched to the base 326. It will be understood by one skilled in the art that in case the fluid connector 338 gets caught on something, to prevent injury or discomfort to the user, the fluid connector 338 can be designed to pull off of the base at a specified force level without using the activation levers 340 due to the flexibility of the fluid connector latches 342.

To release the fluid connector 338 from the base 326, the user squeezes the activation levers 340 until they contact the rigid stop 344, thereby disengaging the fluid connector latches 342 from the latching portion 333 by pivoting and displacing the fluid connector latches 342 radially outward sufficiently to clear the base latch 328. Then, the user lifts the fluid connector 328 proximally off of the base 326.

According to one embodiment, the activation levers 340 have finger bumps 341 to aid the user in locating and using the activation levers 340. Alternatively, the finger bumps 341 can be replaced with a ridge or divots that can provide tactile feedback to the user regarding where to press to release the fluid connector 338 from the base 326. According to another embodiment, the activation levers 340 can have a different color than the fluid connector 338 to provide a visual indicator for the same purpose.

The fluid connector latches 342 include angled planar surfaces 345 that correspond to and engage with the latching portion 333, locking the fluid connector 338 against proximal displacement and each pair of angled planar surfaces 345 contact the latching portion 333 at two distinct locations. The angled planar side surfaces 345 are also substantially parallel to the longitudinal axis of the latching portion 333. The fluid connector latches also include distal beveled surfaces 335 (best shown in FIG. 62) that engage a top surface of the base latch 328 during initial connection. As subsequently described in greater detail, the engagement of the internal facets of the fluid connector 326 with the base latch 328 and the base section 332 prevents rotational movement when the fluid connector 326 is engaged with the base 326. In this exemplary embodiment, the activation levers 340 and the fluid connector latches 342 (together as one) are molded as a separate plastic component from the fluid path portion 339. The activation levers 340 and fluid connector latches 342 pivot on a living hinge. The rigid stop 344 ensures that both of the fluid connector latches 342 travel far enough to completely disengage from the base 326, and also provides a stable anchor for the activation levers 340 during the handling of the fluid connector 338. Additionally, the rigid stop 344 helps prevent rocking of the fluid connector when it is attached to the base 326.

Figure 59:
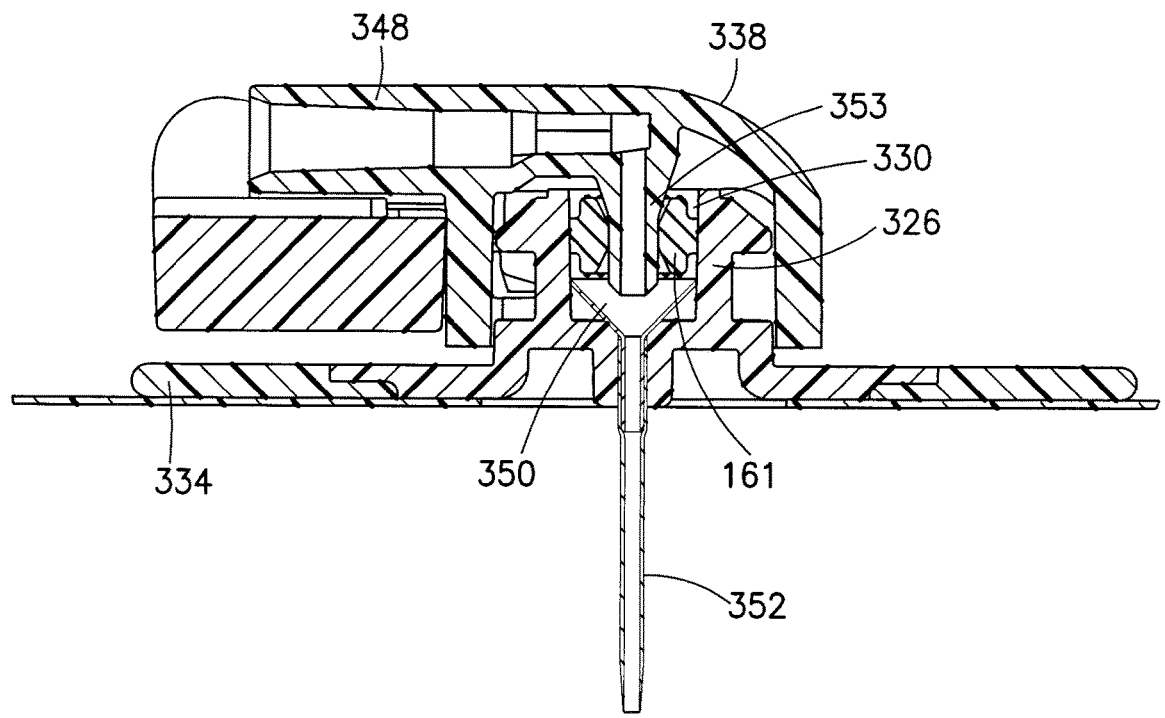
FIG. 59 is an assembled cross-sectional view of the base of FIG. 56 and the fluid connector of FIG. 57.

As shown in FIG. 59, the internal cavity 330 of the base 326 receives a metal wedge 350 and a catheter 352. The wedge 350 has a funnel shape with a hollow center portion that narrows from a broad end to a narrow end. The narrow end of the wedge 350 has a tapered edge used to receive a terminal end of the catheter 352. The catheter 352 is forced up the narrow end of the wedge 350 to form a sealed fluid connection. A pre-slit septum 161 is also retained within the internal cavity 330 of the base 326, to receive a cannula 353 of the fluid connector 338. According to an exemplary embodiment, the septum 161 is held in place within the base 326 by a press fit, which provides a friction force between the septum 161 and the base 326. The septum 161 (as shown in greater detail in FIGS. 20 and 21) includes symmetric concave surfaces on both the top and bottom surfaces that aide in centering the cannula 353 through the slit in the septum 161 during assembly and improve the sealing ability of the septum 161.

Figure 60:
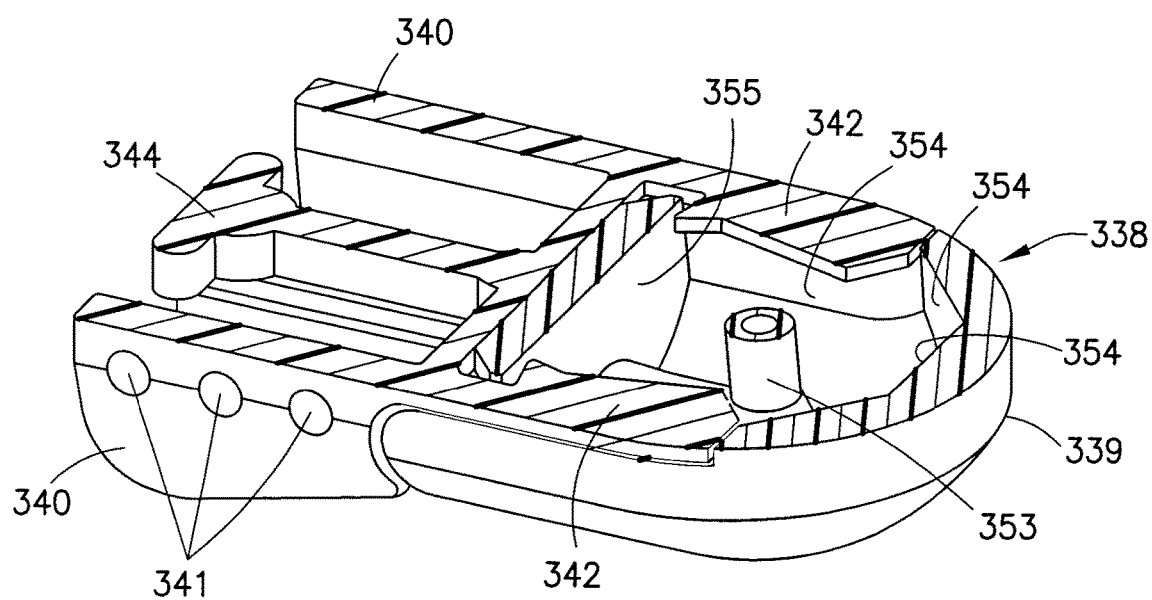
FIG. 60 is a perspective cross-sectional view of the fluid connector of FIG. 57.
Figure 61:
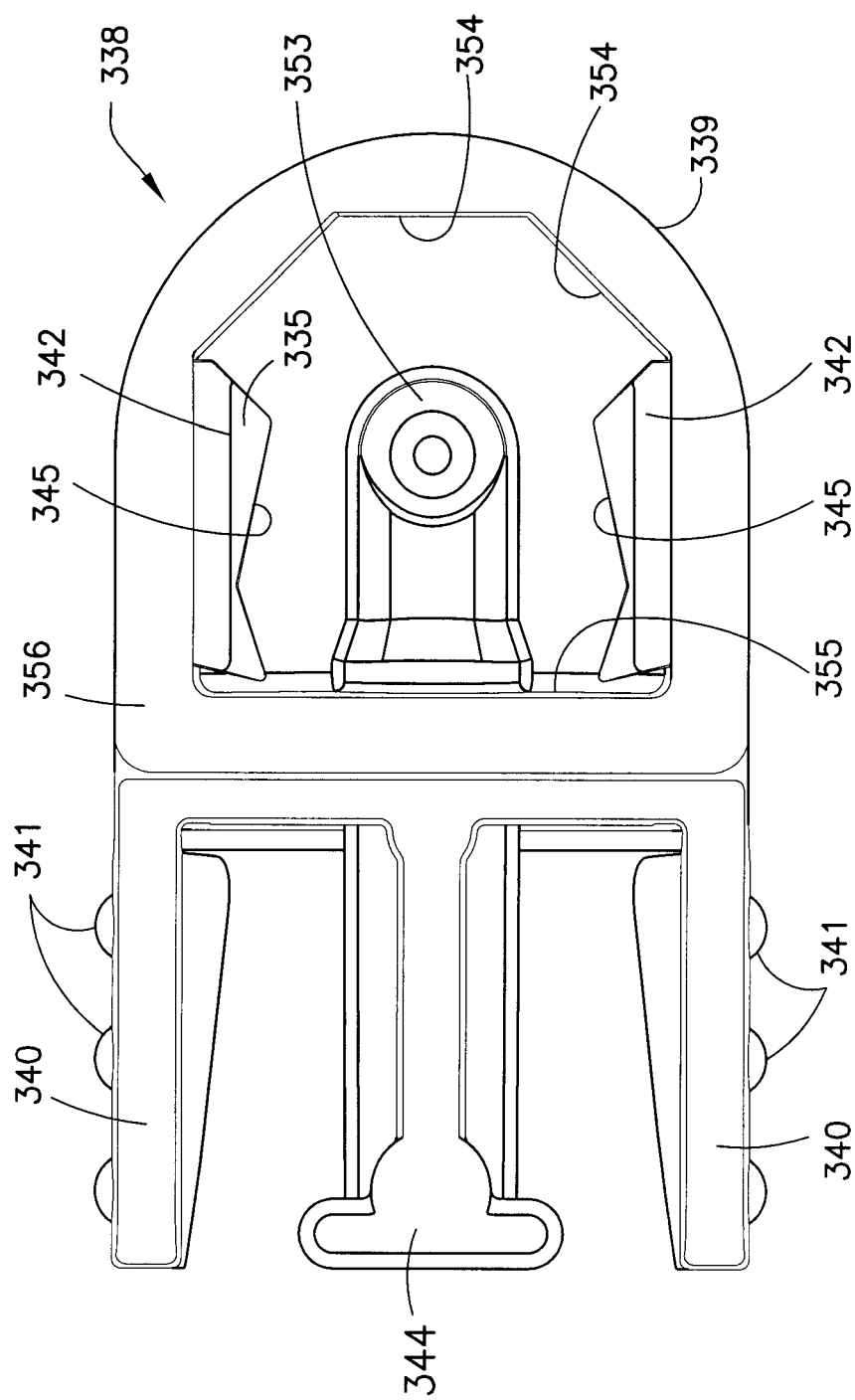
FIG. 61 is a bottom view of the fluid connector of FIG. 57.
Figure 62:
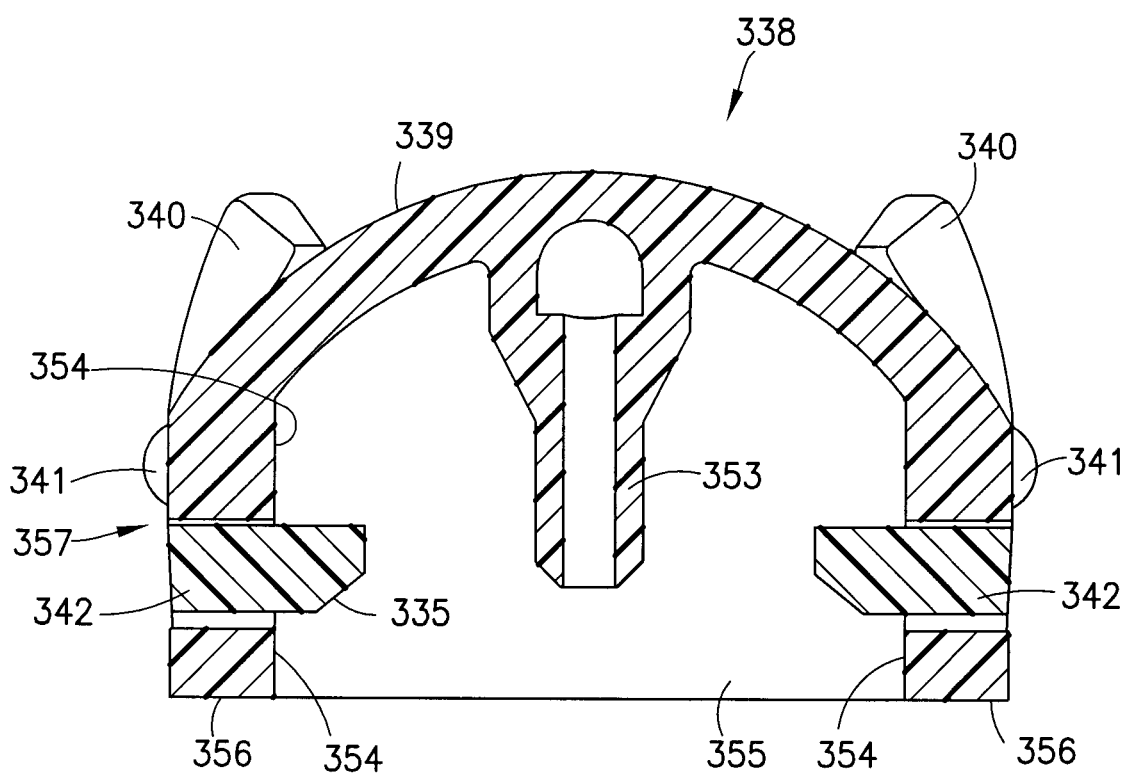
FIG. 62 is a front cross-sectional view of the fluid connector of FIG. 57.
Figure 63:
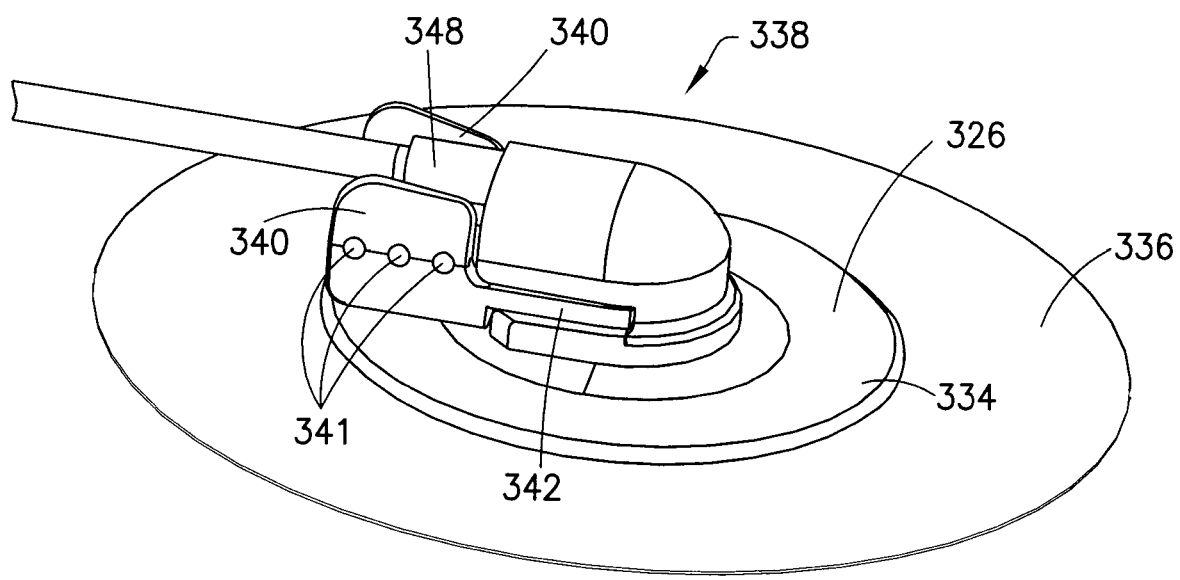
FIG. 63 is an assembled perspective view of the base of FIG. 56 and the fluid connector of FIG. 57.

FIGS. 60-62 illustrate various views of the fluid connector 338. FIG. 60 is a perspective, cross-sectional view, FIG. 61 is a bottom plan view, and FIG. 62 is a front, cross-sectional view. As shown in FIGS. 60-62, the fluid path portion 339 has a back wall 355 and a plurality of internal walls or faces or facets 354. The side walls of the fluid path portion 339 include respective slots 357 (best shown in FIG. 57) through which the fluid connector hub latches 342 move. As best shown in FIG. 62, the top of the interior of the fluid path portion 339 is substantially dome-shaped and the internal facets 354 and the back wall 355 extend all the way to the bottom face 356, even the side walls, which are interrupted by the slots 357.

Referring to FIGS. 56 and 59-62, as the user moves the fluid connector 338 distally toward the base 326, the downward sloped, mushroom shape of the top of the base latch 328 helps center the fluid connector 338 so that the cannula 353 aligns with the slit in the septum 161. As the bottom face 356 passes the facets on the base latch 328, the internal facets 354 and back wall 355 engage the facets of the of the base latch 328, thereby fixing the rotational or circumferential orientation of the fluid connector 338 relative to the base 326. According to one embodiment, the internal facets 354 and back wall 355 engage the facets of the base latch 338 prior to the cannula 353 penetrating the septum 161.

As the user continues to distally displace the fluid connector 338, the internal facets 354 and the back wall 355 engage the facets of the base section 332 to enhance the stability of the connection with the base 326. According to one embodiment, the bottom face 356 of the fluid path portion 339 and the bottom face of the rigid stop 344 contact the base 326 to further enhance the stability of the connection of the fluid connector 338 with the base 326.

Figure 64:
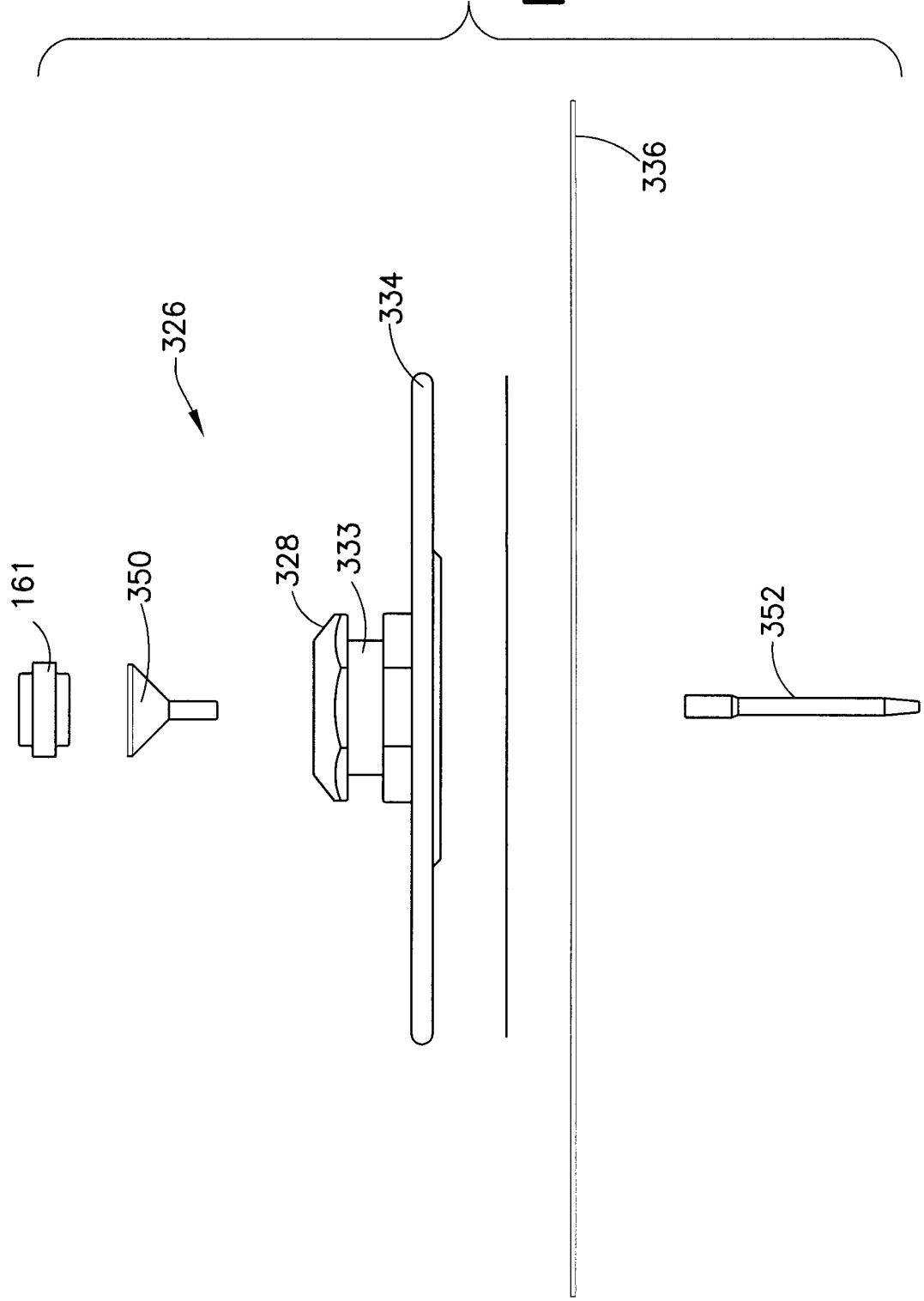
FIGS. 64 and 65 are exploded and cross-sectional views, respectively, of the base of FIG. 56.
Figure 65:
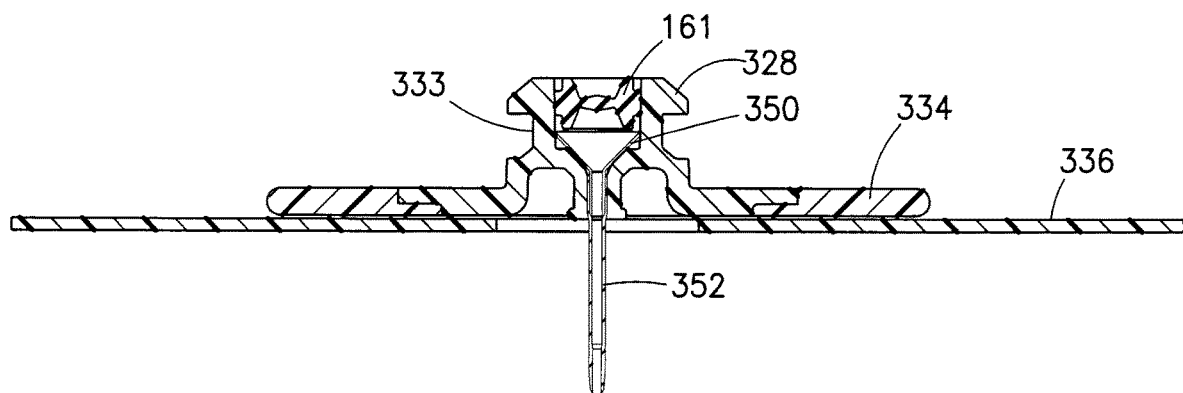

FIGS. 64 and 65 respectively illustrate an exploded view and an assembled cross-sectional view of the base 326, the wedge 350, the septum 351, and the cannula 352 described above.

Figure 66:
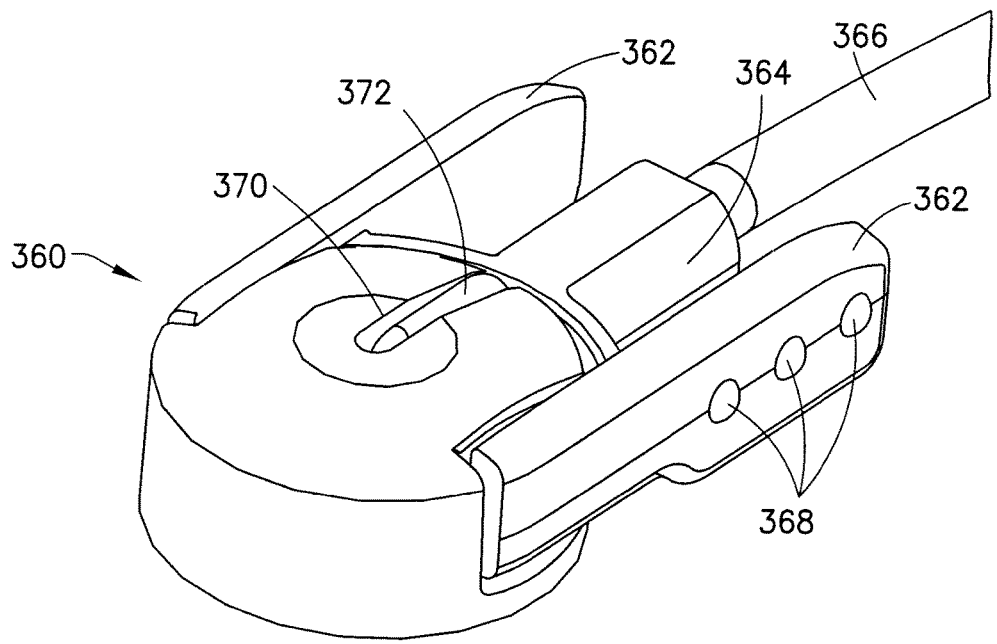
FIG. 66 is a perspective view of a fluid connector having a finger grip release mechanism in accordance with another exemplary embodiment of the present invention.

FIG. 66 illustrates another exemplary embodiment configured to reduce the overall height and profile of the fluid connector 360. Fluid hub 360 differs from previous embodiments by including a substantially planar top surface, as opposed to having a dome-like shape. The shape of the fluid connector 360 substantially reduces the overall height of the device. Similar to the embodiment disclosed in FIGS. 57-65, the fluid connector 360 includes activation levers 362 and a rigid stop 364. Due to the lower profile of the fluid connector 360, the rigid stop 364 also serves as a tube port 364 for engaging tubing 366. The activation levers 362 have finger bumps 368 to aid the user in locating and using the activation levers 362. Alternatively, the finger bumps 368 can be replaced with other exemplary embodiments discussed previously. The fluid connector 360 also includes a groove 370 that receives a bent cannula 372 (more clearly visible in FIG. 92). The bent cannula 372 has a bent shape that corresponds to the outer perimeter of the fluid connector 360 and is received inside the tube port 364, providing a fluid path between the tubing 366 and a base 374.

Figure 67:
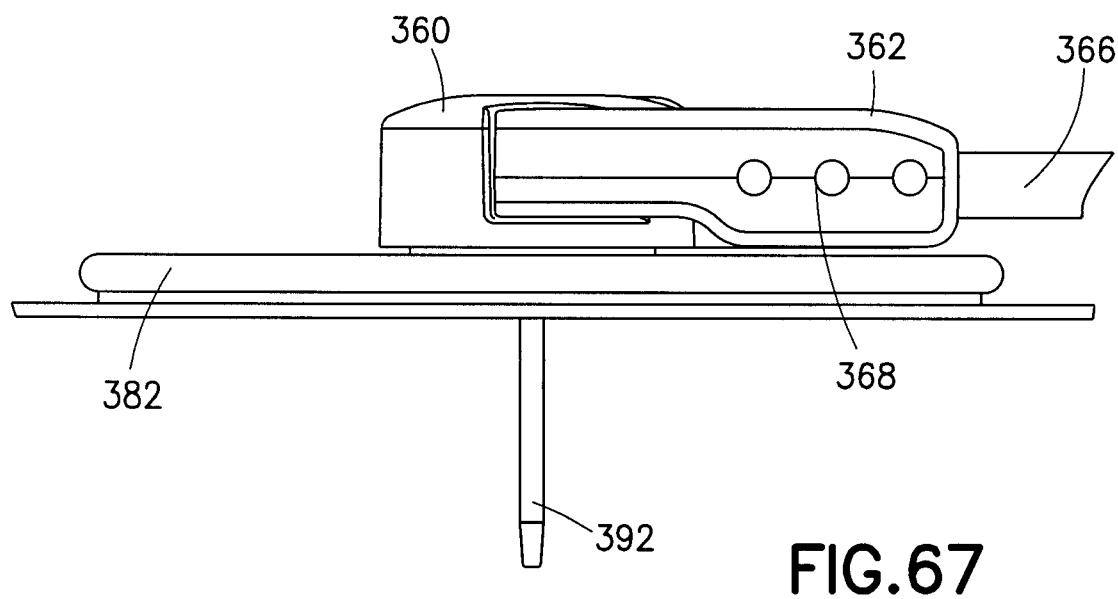
FIG. 67 is a side view of the fluid connector of FIG. 66 connected with a base in accordance with exemplary embodiment of the present invention.
Figure 68:
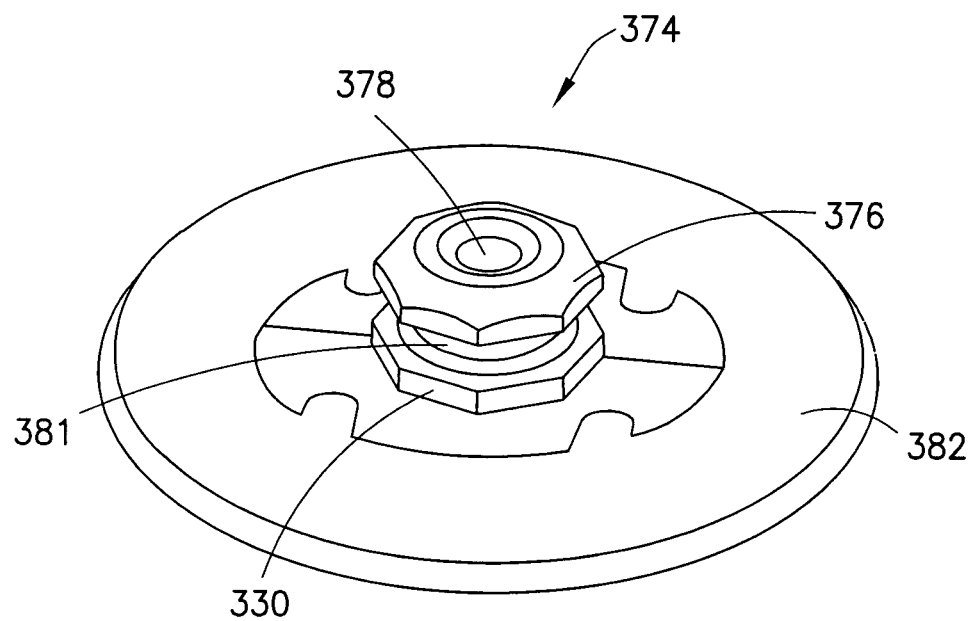
FIG. 68 is a perspective view of the base of FIG. 67.
Figure 69:
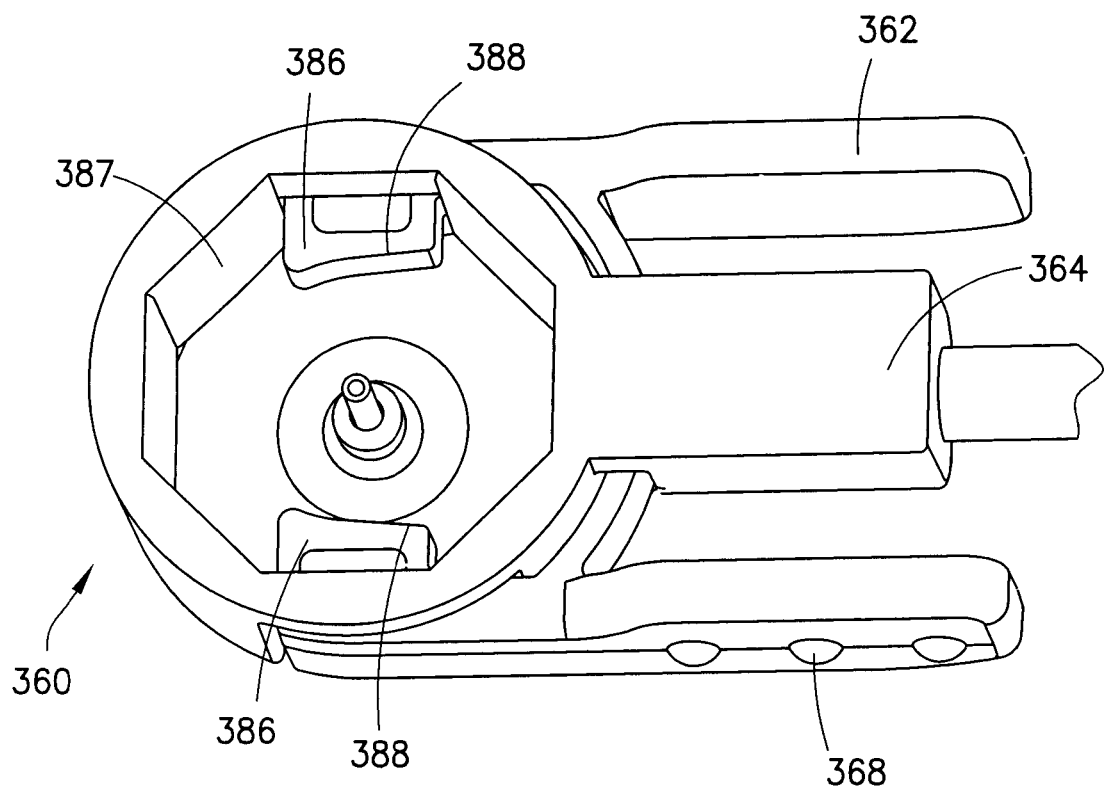
FIG. 69 is a perspective, bottom view of the fluid connector of FIG. 66.
Figure 70:
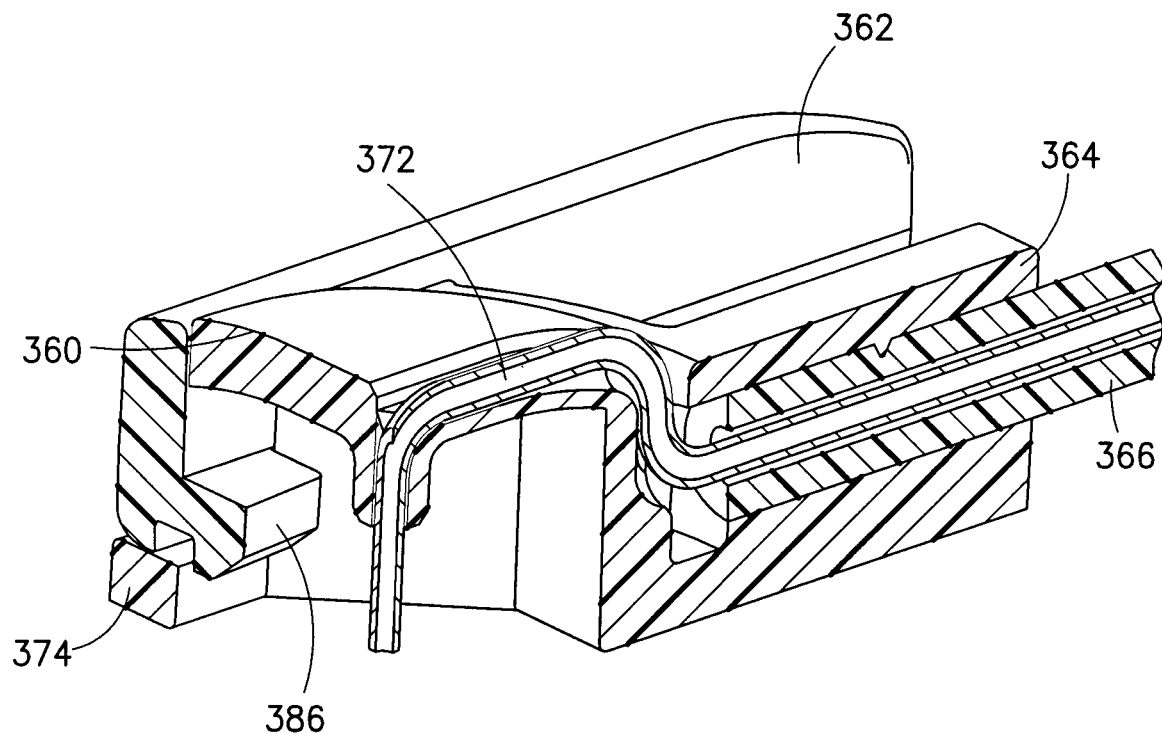
FIG. 70 is a perspective, cross-sectional view of the fluid connector of FIG. 66.
Figure 71:
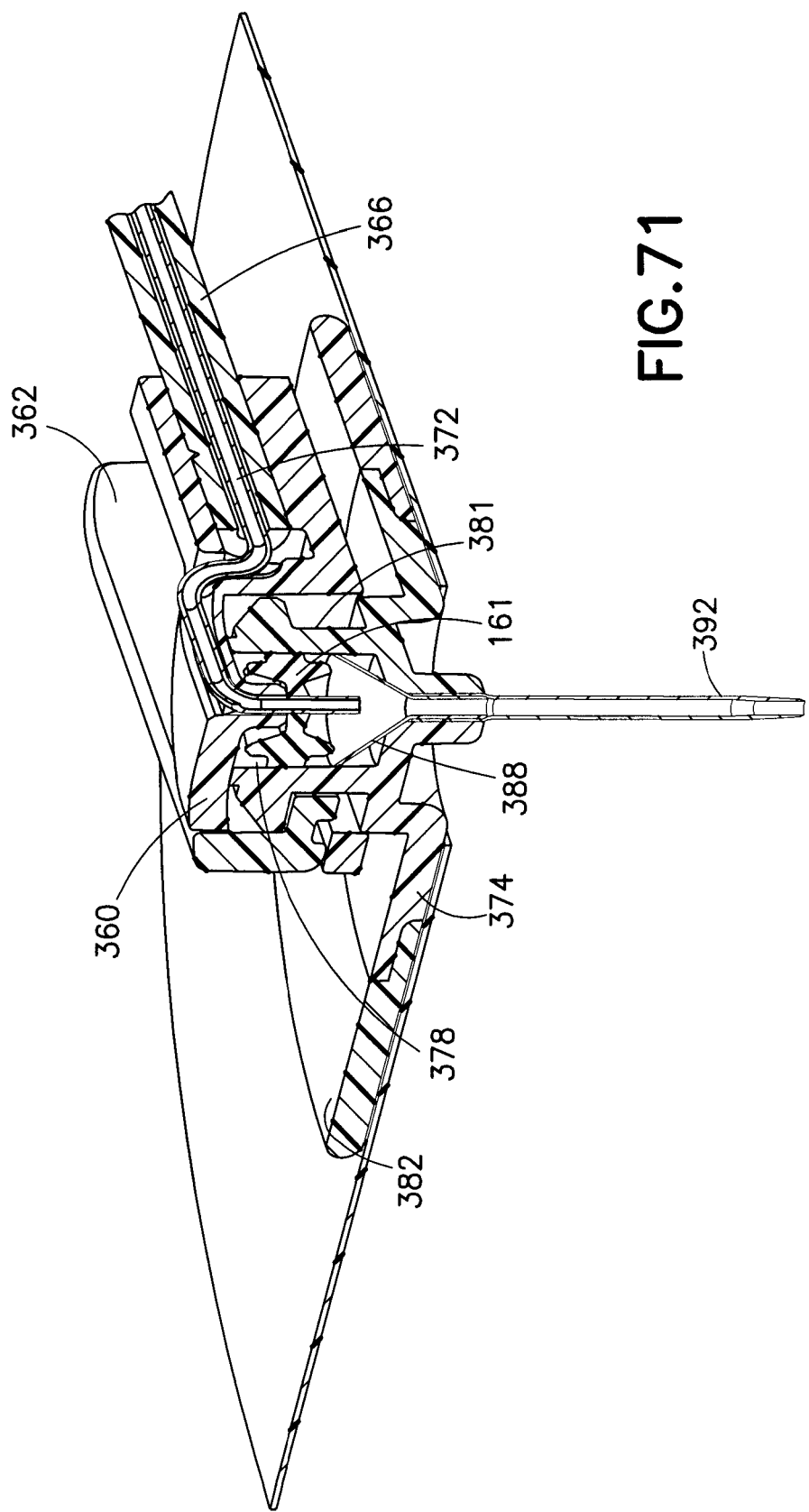
FIG. 71 is a perspective, cross-sectional view of the fluid connector of FIG. 66 connected with the base of FIG. 67.
Figure 72:
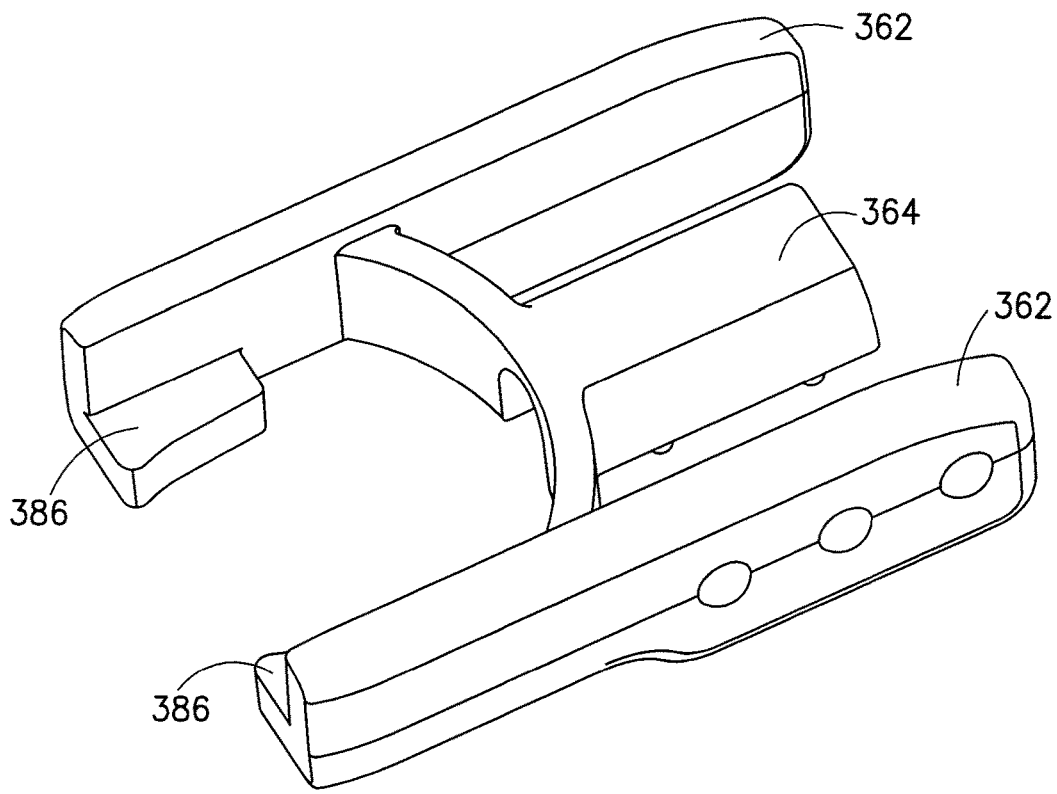
FIG. 72 is a perspective view of a latching portion of the fluid connector of FIG. 66.

The base 374 is substantially similar to that disclosed in FIGS. 56-65. As shown in FIGS. 67, 68, and 71, the base 374 includes a base latch 376 surrounding an internal cavity 378. As illustrated, the base latch 376 is formed in an octagonal shape, having eight perimeter side surfaces or facets. The base 374 also includes a base section 380 that includes a plurality of side surfaces that correspond to the side walls of the base latch 380, each facet corresponding to a different rotational or circumferential position with respect to the fluid connector 360. Alternatively, the base latch 376 and base section 380 can each be formed having a different number of side surfaces. According to one embodiment, the base 374 engages a flexible disc 382 positioned between the base 374 and the user. The flexible disc 382 can be attached to an adhesive patch 384 having an adhesive backing, which can be used to secure the base 374 to the user's skin.

FIGS. 67-72 illustrate additional views of the fluid connector 360 and the base 374. The fluid connector 360 includes fluid connector latches 386 which extend from the activation levers 362. The user attaches the fluid connector 360 to the base 374 by snapping it in place or by pressing the activation levers 362 together until they engage the rigid stop 364, moving the fluid connector 360 distally, and then moving fluid connector latches 376 to a position where they snap and engage the base 374 via engagement with the latching portion 381 (see FIG. 68). Once engaged, the user may remove his or her fingers from the activation levers 362, and the fluid connector 360 will be securely latched to the base 374.

The fluid connector latches 386 include angled planar surfaces 388 that correspond to and engage with the latching portion 381. The internal facets 387 of the fluid connector 360 engage the facets of the base latch 376 and the base portion 380, thereby locking the fluid connector 386 against rotational movement when the fluid connector 360 is engaged with the base 374. The activation levers 362 and fluid connector latches 386 pivot on a living hinge. By contacting the rigid stop 364 with the activation levers 362, rigid stop 364 ensures that both of the fluid connector latches 386 travel far enough to completely disengage from the base 374, and provides a stable anchor for the activation levers 362 during the handling of the fluid connector 360. Additionally, the rigid stop 364 helps prevent the fluid connector 360 from rocking when attached to the base 374.

As shown in FIG. 71, the internal cavity 378 of the base 374 receives a metal wedge 388, a septum 161, and catheter 392. The wedge 388 has a funnel shape with a hollow center portion that narrows from a broad end to a narrow end. In contrast to other wedges recited herein, wedge 388 has a shorter profile funnel portion, thus enabling a more compressed assembly with the septum cavity 378. The narrow end of the wedge 388 has a tapered edge used to receive a terminal end of the catheter 392. The septum 161 is pre-slit and is retained within the internal cavity 378 of the base 374, and receives the bent cannula 372. The septum 161 may be held in place within the base 374 by a press fit, or other exemplary means known in the art or disclosed herein, such as an adhesive. The septum 161 includes symmetric concave surfaces on both the top and bottom surfaces which aide in centering the cannula 372 through the slit in the septum 161 during assembly and improves the sealing ability of the septum 161 with respect to the cannula 372. A central horizontal portion or web of the septum 161 includes a convex top and bottom surface that contain the slit. These convex surfaces provide additional sealing pressure, keeping the slit sealed, particularly when external forces are applied to the septum 161 when the fluid connector 386 is disconnected from the base 374.

Figure 73:
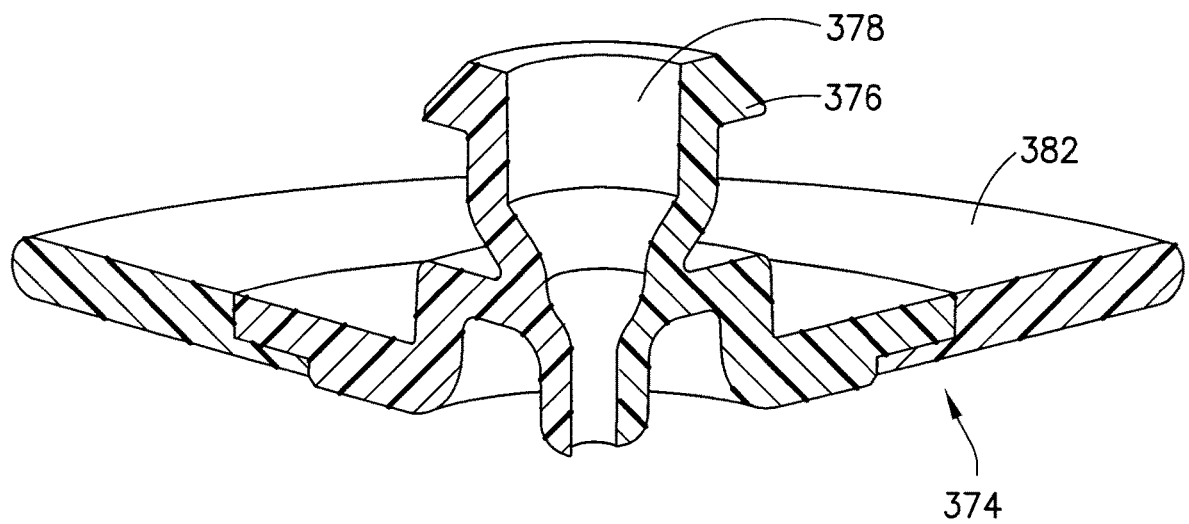
FIG. 73 is a perspective, cross-sectional view of the base of FIG. 67.

FIG. 73 illustrates a sectional view of the base 374.

Figure 74:
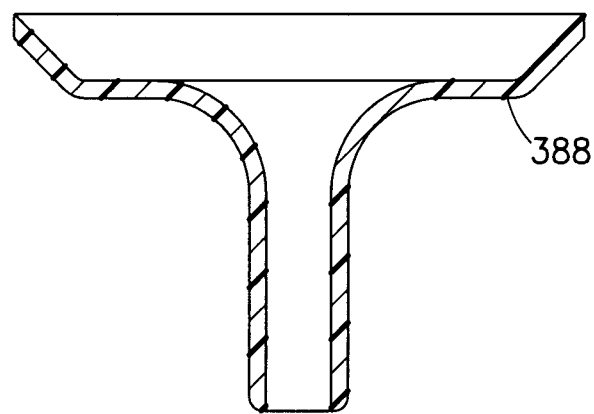
FIG. 74 is a cross-sectional view of a wedge in accordance with an exemplary embodiment of the present invention.

FIG. 74 is a cross-sectional view of the wedge 388 illustrating the low profile and margarita-glass-like form.

Figure 75:
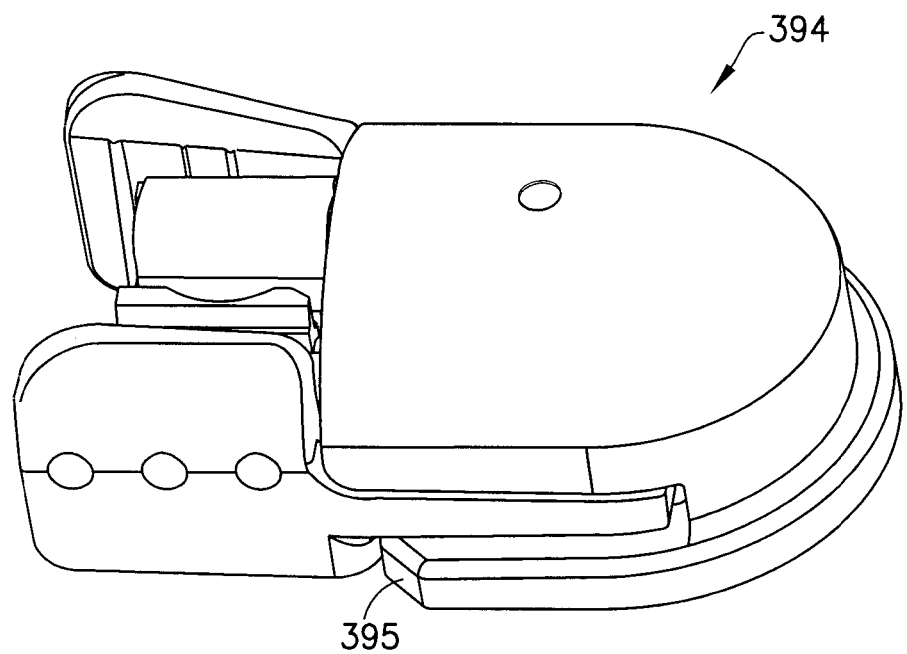
FIGS. 75 and 76 are perspective top and bottom views, respectively, of a fluid connector in accordance with another exemplary embodiment of the present invention.
Figure 76:
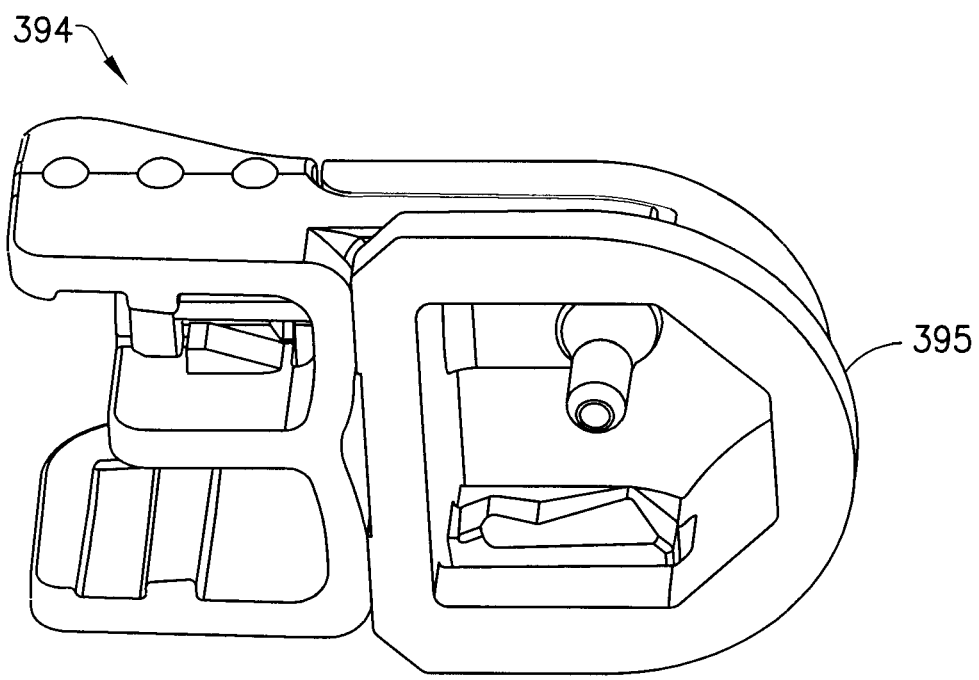

FIGS. 75 and 76 illustrate an embodiment of a fluid connector 394 in which a lower rim 395 of the fluid path portion extends radially relative to the outer side wall rather than being substantially coplanar with the outer side wall. This configuration provides greater stability when the fluid connector 394 is connected to a base.

Figure 77:
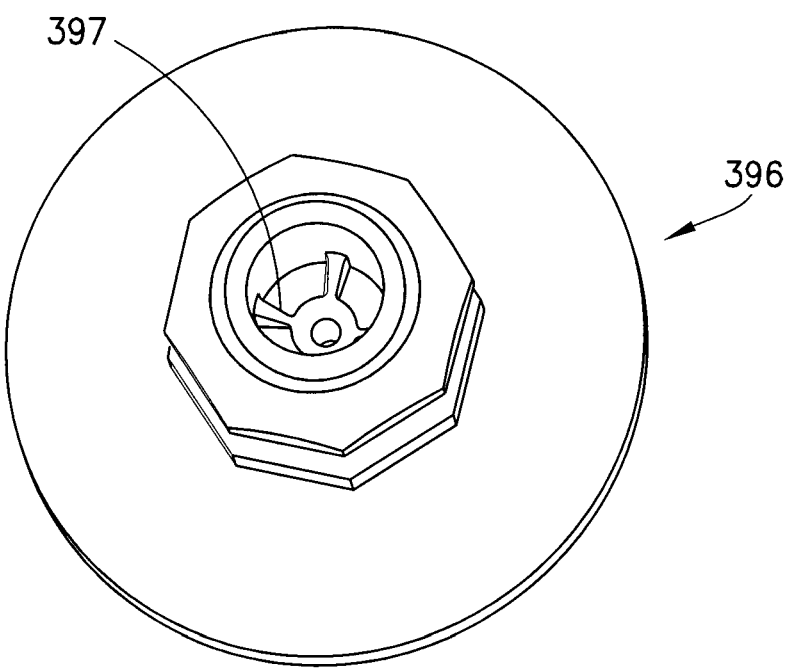
FIG. 77 is a perspective view of a base in accordance with another exemplary embodiment of the present invention.

FIG. 77 is a perspective view of a base 396 in accordance with an embodiment of the present invention. In an interior, the base 396 includes a plurality of support ribs 397. According to one embodiment, the support ribs 397 are sloped. According to another embodiment, the support ribs 397 are concave. The support ribs provide additional support for a wedge to be inserted in the base 396. According to one embodiment, the shape of each of the support ribs is complimentary to the shape of the wedge to support the wedge along substantially all of the support rib. Alternatively, the support ribs can be shaped so that they contact the wedge at discrete points.

FIGS. 78-81 are cross-sectional views of alternative bases. In particular, these embodiments vary in their internal structure for receiving and supporting the wedge. In FIG. 78, the interior of the base 398 is beveled 399 and stepped 400 to transition to a convex tapered portion 401. These features can create a "well" to catch and collect debris created during wedge installation. Such a well can be useful to insure proper seating of the wedge and flexible cannula. Similarly, the base 402 of FIG. 79 also has a well, but the transition portion 404 from the cylindrical portion 403 to the convex tapered portion 405 is concave and is not stepped.

The base 406 of FIG. 80 is similar to the base 402 of FIG. 79, except the transition 407 is convex. The base 408 has a flat step 409 that transitions to a convex tapered portion 410. In an alternative embodiment, the portion 410 is substantially conical.

It is also noted that in comparison with the embodiment of FIG. 65, in the embodiments of FIGS. 78-81, the annular space surrounding the central, distal, columnar protrusion (or central column) extends proximally further into the base. Additionally, the distal columnar protrusion extends beyond the primary distal surface of the base. As discussed in greater detail below, these differences can accommodate different needle guards for protecting an introducer needle.

Figure 82:
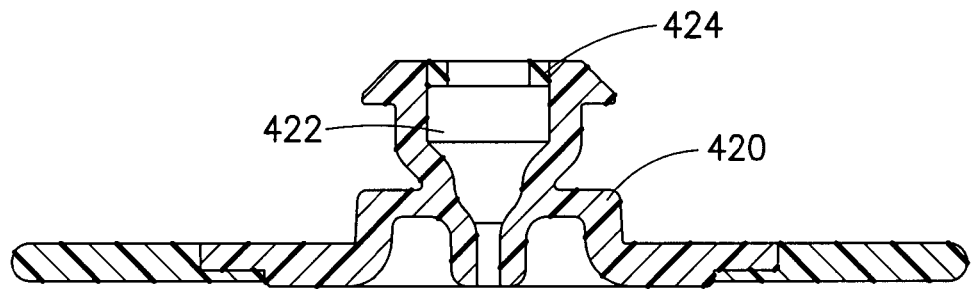
FIG. 82 is a cross-sectional view of a base in accordance with another exemplary embodiment of the present invention.

FIG. 82 illustrates a cross-sectional view of another exemplary embodiment of a base 420. Features of the base 420 can be interchangeable with each of the other exemplary bases previously discussed. Base 420 includes an interior cavity 422 which can retain a septum (not shown) and facilitate a fluid flow path between a fluid connector (not shown) and a catheter (not shown), as previously discussed in more detail. Base 420 includes a retention ring 424 located on a top portion of the base 420. The retention ring 424 can be fastened to the base 420 via swaging heat, ultrasonic welding, an adhesive, or by any other fastening means known in the art. The retention ring 424 prevents the septum from slipping out of the interior cavity 422 of the base 420 (for example, when the fluid connector is removed) by decreasing the diameter of the opening of the base 420. The retention ring can extend completely around the perimeter of the base opening. Alternatively the retention ring 424 can be a partial or discontinuous ring. Alternatively, the retention ring can be fastened to the top surface of the base 420, so that the retention ring at least partially overlaps the opening of the base 420, effectively retaining the septum within the interior cavity 422 of the base 420. As another alternative, the septum can be retained within the interior cavity by swaging the material of the base 420 to form an integrated retaining ring.

Figure 83:
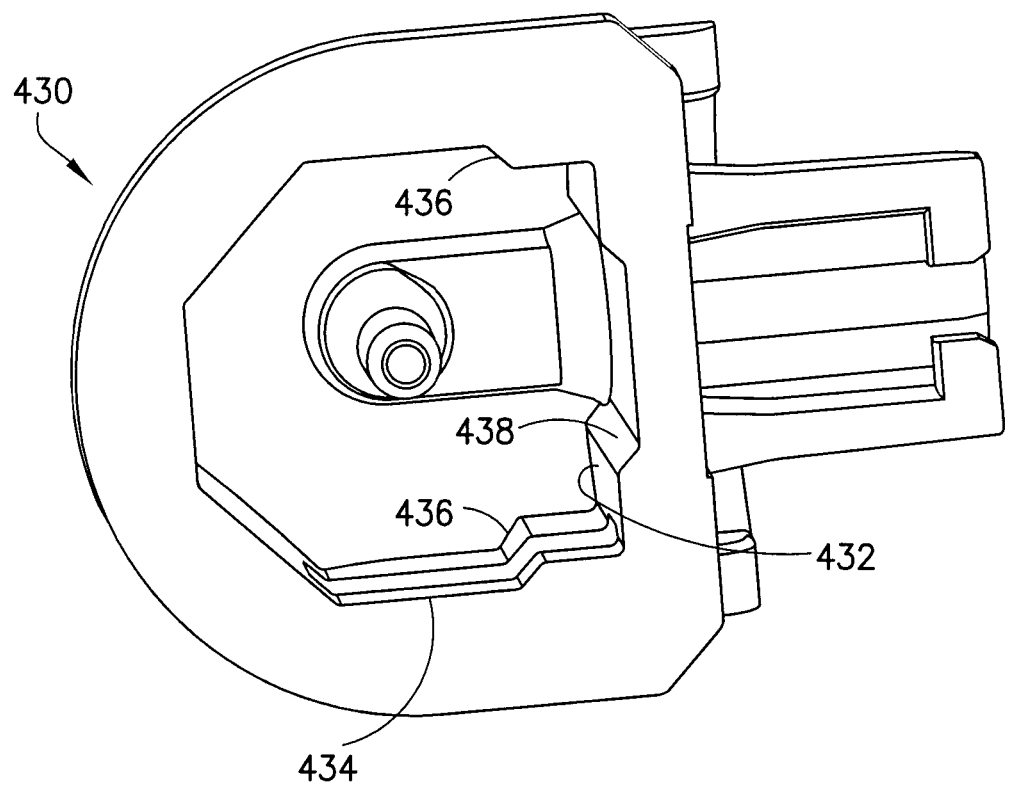
FIG. 83 is a bottom perspective view of a fluid path portion of a fluid connector in accordance with another exemplary embodiment of the present invention.

FIG. 83 is a perspective bottom view of a fluid path portion 430 of a fluid connector in accordance with an embodiment of the present invention. In comparison t the fluid path portion 339 of FIG. 60, the fluid path portion 430 has a stepped rear interior wall 432 and stepped interior side walls 434. This configuration can increase the stability of the connection with the base by providing additional facets 436 and 438 for contacting facets of the base latch and base portion of the base.

Figure 84:
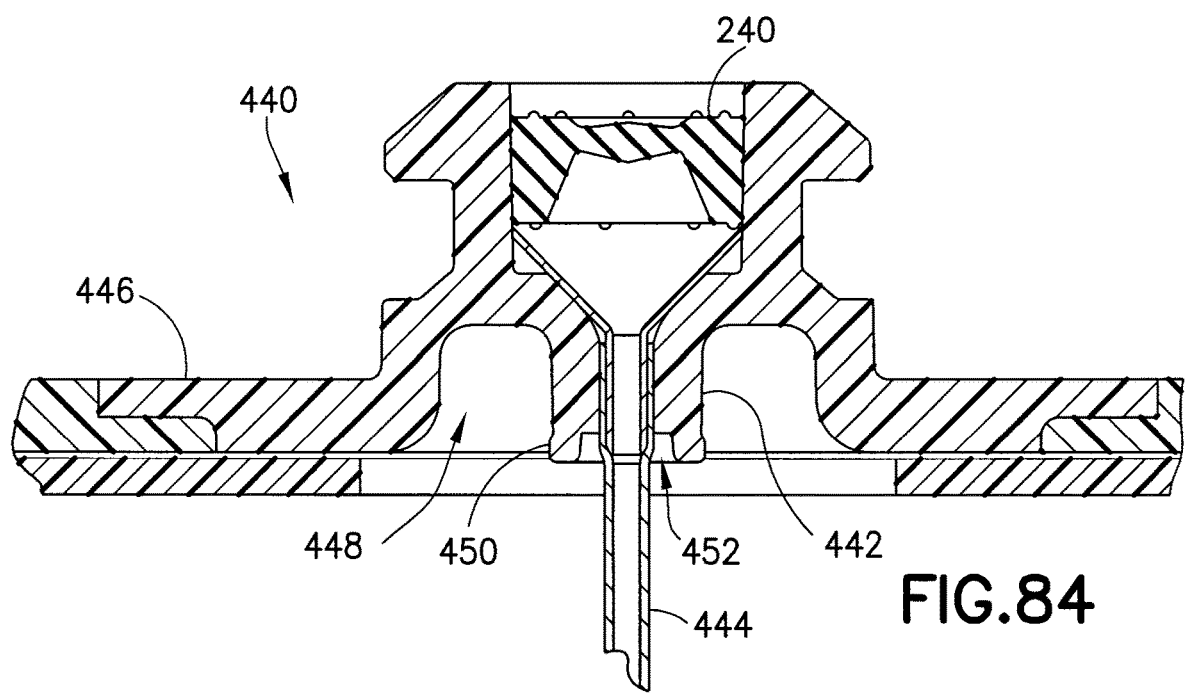
FIG. 84 is a partial cross-sectional view of a base in accordance with another exemplary embodiment of the present invention.

FIG. 84 is a cross-sectional view of a base 440 in accordance with an embodiment of the present invention. Like the bases of FIGS. 78-81, on its distal side, the base 240 has a central column 442 from which the soft catheter 444 protrudes, and the central column 442 extends distally below the primary distal surface 446 of the base 440. Additionally, the annular space 448 surrounding the central column 442 extends proximally further into the base than the base of FIG. 65. The base 440, however, also has a lip 450 at the distal end of the central column 442 and an annular recess 452 on its distal face surrounding the soft catheter 444. The lip 450 and annular space 448 can accommodate a needle guard to protect an introducer needle, as subsequently discussed in greater detail. The annular space 452 can provide flexibility for the soft catheter 444 and reduce instances of tearing during installation of the soft catheter 444 into the base 440.

Figure 85:
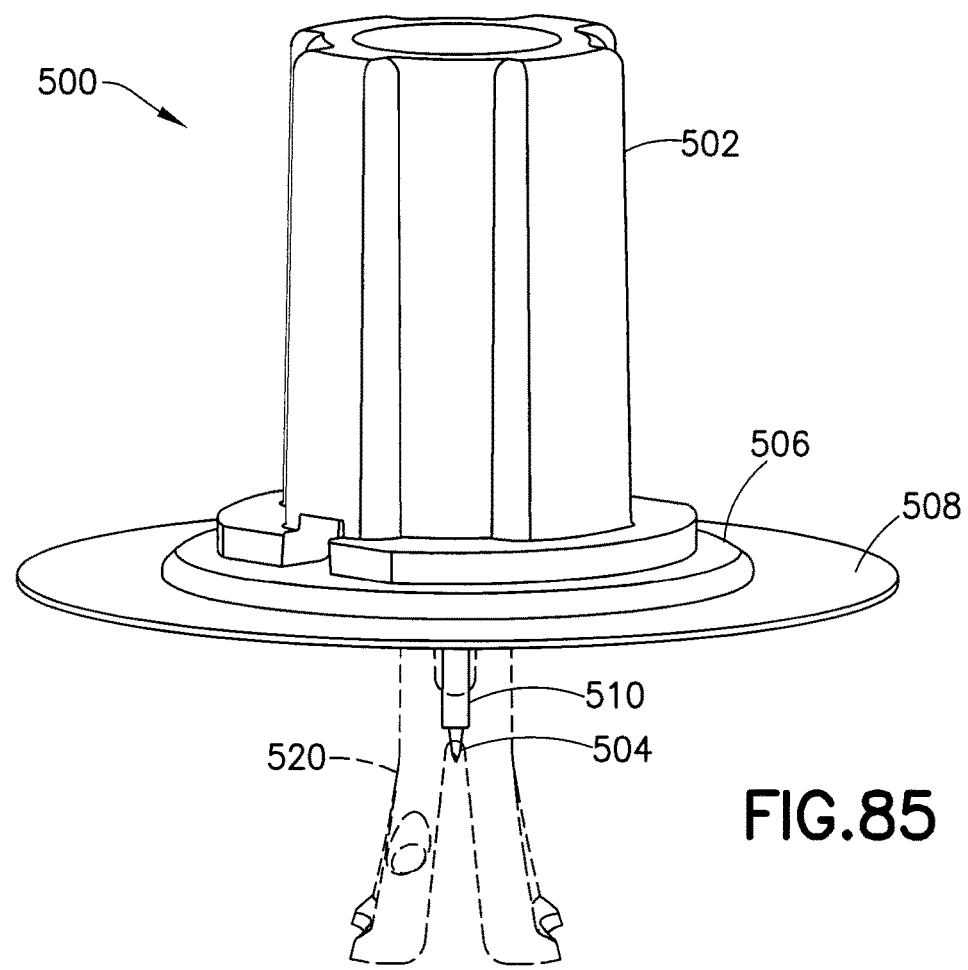
FIG. 85 is a perspective view of an infusion set assembly in accordance with an embodiment of the present invention.

FIG. 85 is a perspective view of an infusion set assembly 500 in accordance with an embodiment of the present invention. The assembly includes an insertion hub 502 with a hollow introducer needle 504 connected thereto, and an infusion set base 506 that is connected to the insertion hub 502. The base 506 includes an adhesive pad 508 to secure the base 506 to the skin of a patient, and a hollow base cannula 510. According to one embodiment, the base cannula is a soft plastic catheter 510. In this embodiment, the introducer needle 504 passes through the soft catheter 510 and extends beyond the proximal end of the soft catheter 510. It will be understood by one skilled in the art, however, that the present invention is not limited to a soft catheter. For example, the base cannula 510 may be a rigid metal cannula, in which case a separate introducer needle is not required. The assembly 500 also includes a needle guard 520, which is shown in dotted lines in FIG. 85 for clarity.

As shown in FIGS. 86-91, according to one embodiment, the needle guard 520 is an integral, one-piece plastic structure that includes an upper or proximal portion 522 for connecting to the base 506 and a lower or distal portion 524 for user or patient interaction. In other words, according to one embodiment, the needle guard 520 is integrally formed as a unitary structure.

Although other users can use the infusion set insertion assembly 500 (for example, a health care professional), for brevity the user will be referred to as "the patient" hereinafter. As best shown in FIGS. 86-88, the distal portion 524 includes touch points 526 that are sculpted in a manner to guide the patient in squeezing the lower portion 524. For example, the touch points 526 are wide and curved in a concave shape for comfortable interaction with the patient's fingers. Additionally, according to one embodiment, the distal portion 524 of the needle guard 520 includes a plurality of support ribs 528 on the interior thereof to increase the structural rigidity of the distal portion.

As will be described in greater detail below, the proximal portion 522 has a pair of opposing, inward cantilevered gripping portions 530 for selective connection with the base 506. In addition, both the proximal and distal portions 522 and 524 have axial cutouts (532 and 534, respectively) therein that effectively divide the needle guard 520 into right and left sides. According to one embodiment, the proximal axial cutouts 532 and the distal axial cutouts 534 are axially aligned, thereby forming pairs of aligned cutouts. Disposed between the cutouts and joining the right and left sides of the needle guard 520 is a pair of fulcrum webs 536.

The fulcrum webs 536 also provide a fulcrum for relative rotation of the right and left sides of the needle guard 520, as permitted by the flexibility of the plastic material of which it is made. As shown, for example, in FIG. 89, as the patient presses the touch points 526 of the distal portion 524 radially inward, the proximal portion 522 correspondingly displaces radially outward (arrows A in FIG. 89) about the fulcrum webs 536. Conversely, as the biasing force is removed (i.e., the patient releases the radially inward pressing force), the distal portion 524 displaces radially outward about the fulcrum webs 536 and returns to its initial, unbiased position, and the proximal portion 522 correspondingly displaces radially inward about the fulcrum webs 536 to its initial, unbiased position (arrows B shown in dotted line).

As noted, the needle guard 520 is preferably made of a rigid but flexible plastic, such as, polypropylene. According to one embodiment, the needle guard 520 has a height of about 0.65" (16.5 mm), a width of about 0.18" (4.5 mm) at the proximal portion, and widths of about 0.34" (8.6 mm) and 0.45" (11.4 mm) at the distal end of the needle guard 520.

Figure 92:
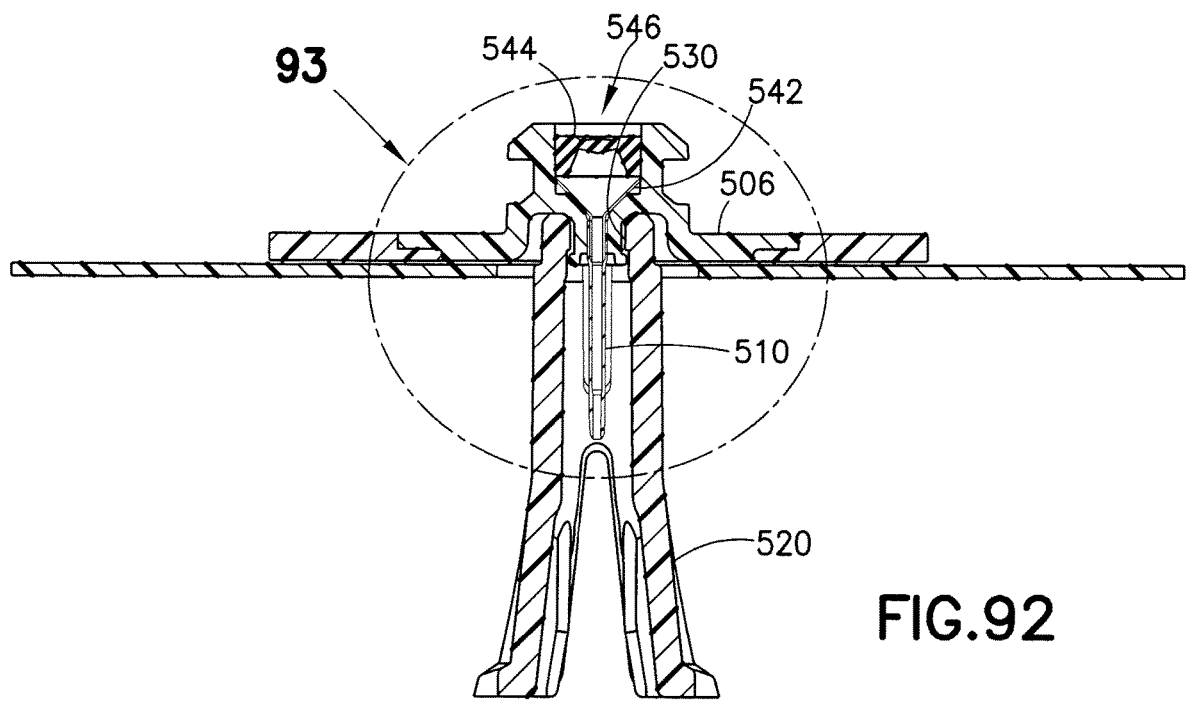
FIGS. 92 and 93 are cross-sectional views of the needle guard of FIG. 86 shown connected to a base of an infusion set.
Figure 93:
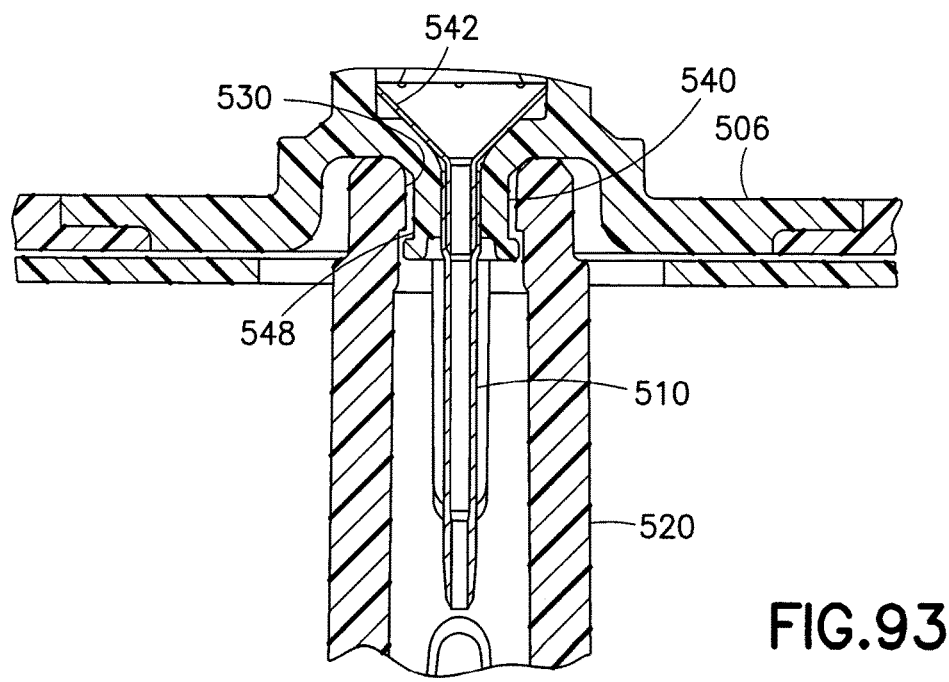

FIG. 92 is a cross-sectional view of the needle guard 520 connected to the base 506 and FIG. 93 is an enlarged view of a portion of FIG. 92. The insertion hub 502 and the introducer needle 504 are omitted from FIGS. 93 and 94 for clarity. On its distal side, the base 506 has a central column 540 from which the soft catheter 510 protrudes distally. One skilled in the art will appreciate, however, that embodiments of the present invention are not limited to the column being centrally located with respect to the base. According to one embodiment, the soft catheter is held in the central column 540 by a metal wedge 542, the proximal side of which is covered by a septum 544 that seals the proximal end of a port 546. The central column 540 has a middle portion that is undercut, thereby forming a lip 548. According to one embodiment, the base 506 has an annular space surrounding the central column 540. During use, the gripping portions 530 of the needle guard 520 engage the lip 548 of the central column 540 to retain the needle guard 520 on the base 506. According to on embodiment, as shown in FIG. 93, when connected with the base 506, a proximal portion of the needle guard 520 contacts the proximal celling of the annular space surrounding the central column 540.

Preferably, the external diameter of the lip 548 is slightly larger than the internal diameter of the gripping portions 530, and thus, when installed on the base 506, the gripping portions are displaced or deflected radially outward about the fulcrum webs 536 and thereby (due to the resilience of the plastic material of which the needle guard 520 is made) provide a radially-inward-directed gripping force to retain the needle guard 520 on the base 506. Additionally, as best shown in FIG. 93, the distal portions of the gripping portions 530 engage the proximal portion of the lip 548 to prevent undesired axial displacement of the needle guard 520 relative to the base. But because the surface area of engagement is so small, the amount of outward rotation of the gripping portions about the fulcrum webs 536 necessary to disengage the needle guard from the base 506 is also small.

The needle guard 520 is attached to the base 506 prior to shipping, to protect the introducer needle 504 and the base cannula 510. Therefore, prior to inserting the infusion device into the skin, the patient must first remove the needle guard 520. As described previously, the user presses the touch points 526 together, thereby rotating the gripping portions 530 radially outward about the fulcrum webs 536 and disengaging the gripping portions 530 from the central column 540 of the base 506. Subsequent to the disengagement, the patient completely removes the needle guard 520, thereby exposing the introducer needle 504 and readying the infusion device for insertion.

Thus, little or no axial force is required to separate the needle guard 520 from the base 506. Further, by selecting materials and the dimensions of the fulcrum webs 536, the needle guard 520 requires only a small amount of lateral force by the patient to disengage the gripping portions 530 from the central column 540. Further, embodiments of the present invention allow the needle guard 520 to be removed without dulling or causing damage to the introducer needle 504. Additionally, because little or no axial force is required to disengage the needle guard 520 from the base, the needle guard can be removed without inadvertently activating an introducer needle shielding mechanism. Further still, embodiments of the present invention permit higher manufacturing variation tolerances to reduce creep/aging affects and high stress levels in the part while retaining sufficient holding force to prevent the needle guard 520 from being accidentally removed. Embodiments of the present invention provide a controlled deflection of the gripping portions 530 to produce a consistent retaining force with a large tolerance and low removal force requirement. Moreover, in comparison with other commercially available needle guards, one benefit of embodiments of the present invention is that the patient has more control when removing the needle guard. For example embodiments of the present invention reduce the risk of a potential needle stick or damage to the needle and/or cannula by eliminating the sometimes "jerky" motion of simply overcoming friction and pulling the needle guard free.

Figure 94:
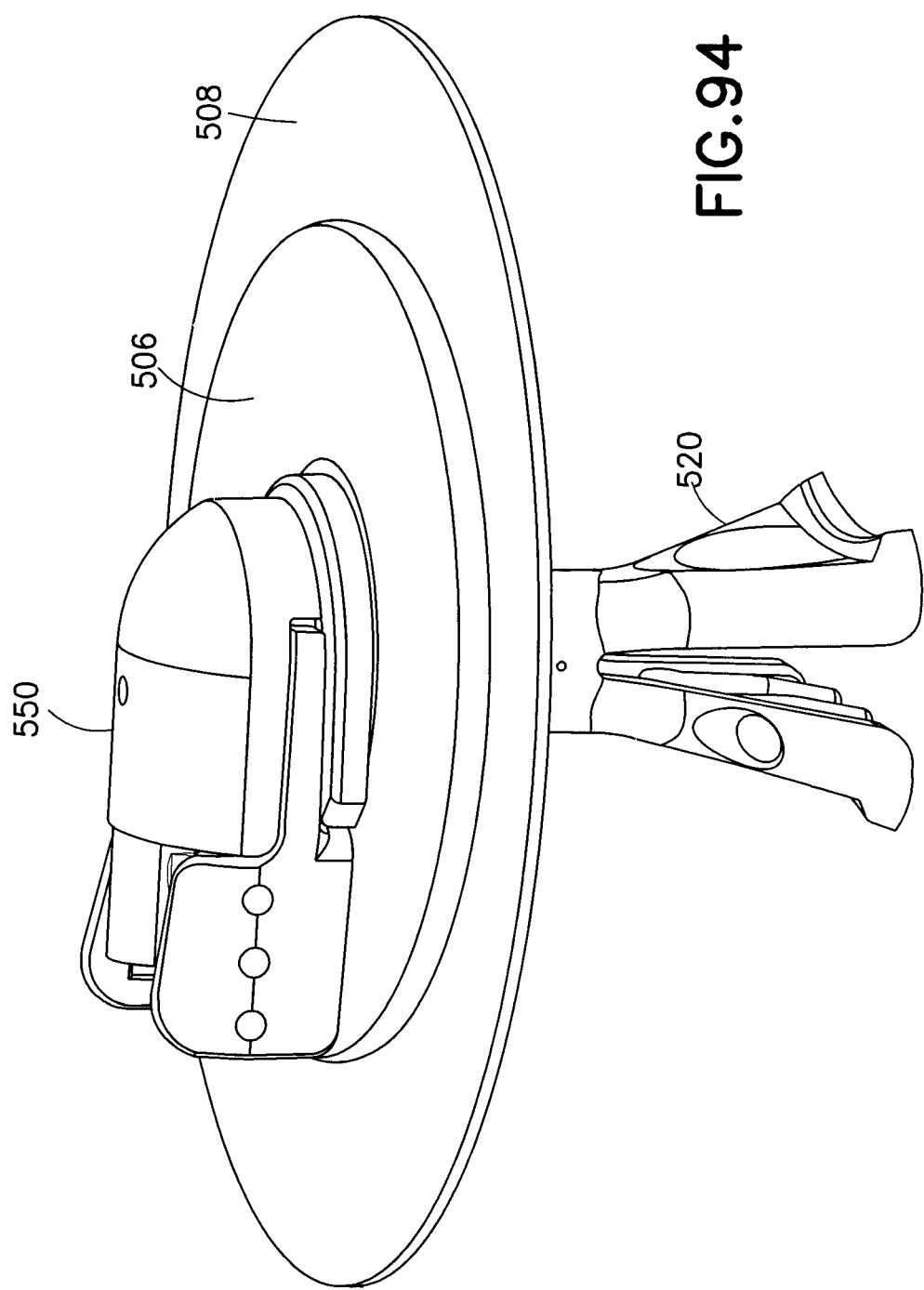
FIG. 94 is a perspective view of a fluid connector connected with to base of FIG. 92, which is connected to the needle guard of FIG. 86.

FIG. 94 illustrates how the patient can reattach the needle guard 520 to the base 506 after withdrawal of the base 506 from the skin, even if the base 506 remains connected with a fluid connector 550 (fluid connector tubing is omitted for clarity).

Figure 95:
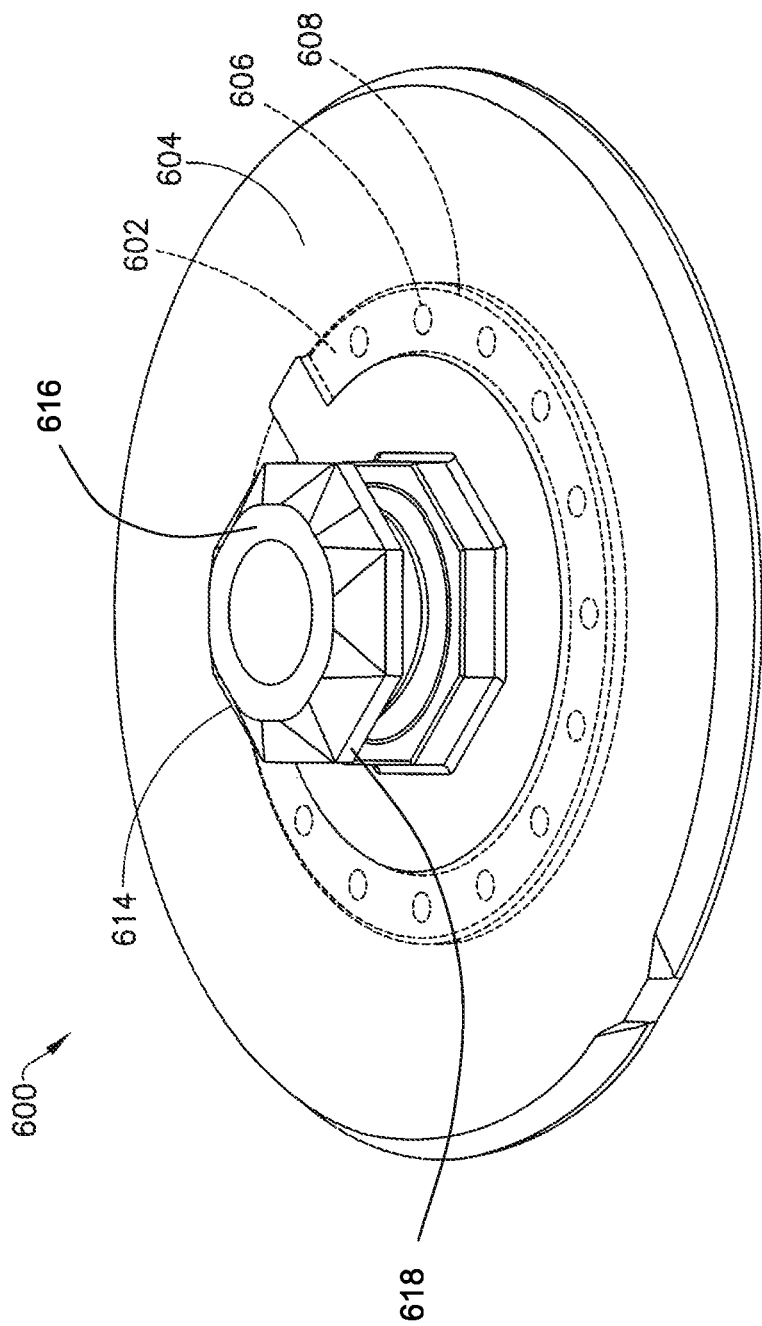
FIGS. 95-97 illustrate an infusion base 600 in accordance with another embodiment of the present invention.
Figure 96:
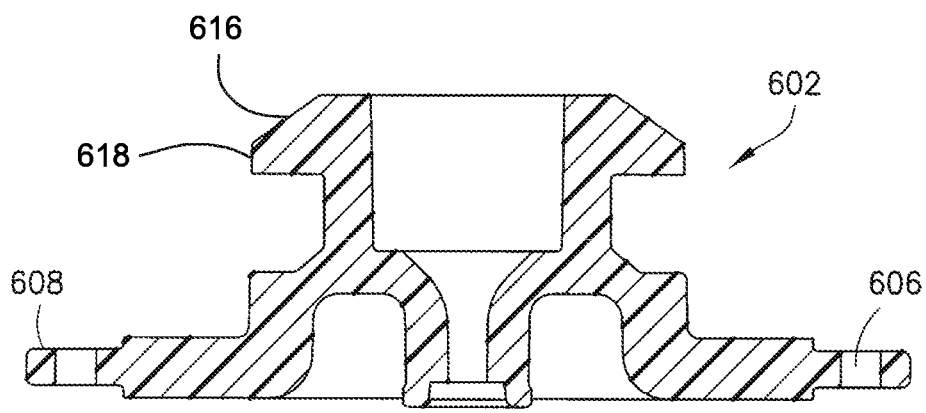
Figure 97:
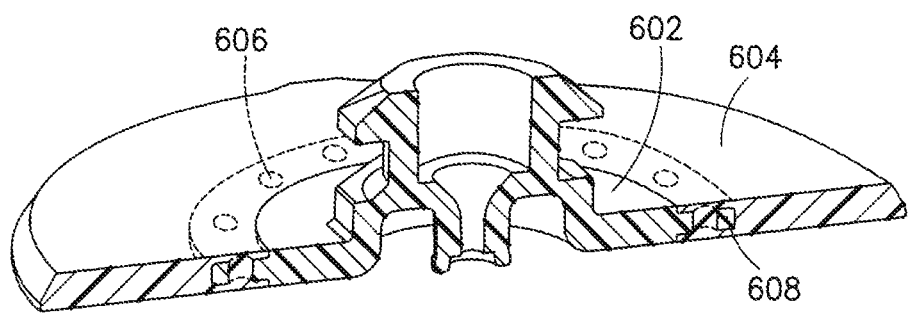

FIGS. 95-97 illustrate an infusion base 600 in accordance with another embodiment of the present invention. As shown in FIGS. 95-97, the infusion base 600 has a base portion 602 and a disc portion 604. The horizontal distal portion of the base portion 602 has a an outer portion 608 that has a reduced thickness in comparison to the reset of the horizontal distal portion. In additional the outer portion 608 has a plurality of through holes 606, as subsequently discussed in greater detail.

According to one embodiment, the disc portion 604 is a flexible disc portion 604, and the holes 606 and reduced thickness of the outer portion 608 facilitate bonding between the base portion 602 and the flexible disc portion 604. More specifically, the base portion 602 is molded in a first shot, and the flexible disc portion 604 is molded in a second shot, during which the material of the flexible disc portion 604 flows around the outer portion 608 and through the holes 606. The shape of the outer portion 608 provides a double overlapping joint with the material of the flexible disc portion 604 and the holes 606 provide additional bonding surface area, as well as an additional mechanical interlock. In contrast, the embodiment of FIG. 4 has only a single overlapping joint for bonding.

In addition, as shown best in FIG. 95, the base portion 602 has facets 614 on the top of the base latch 616. These facets 614 allow the flat vertical sides 618 of the base latch 616 to be thicker than in previously-described embodiments, for example, the embodiment of FIG. 56, in which the top surface of the base latch 328 is rounded. This increased thickness provides increased surface area, and thus, the flat vertical sides 618 provide stronger engagement between the base 600 and a fluid connector, and stronger resistance to rotational torque between the fluid connector and the base 600.

Figure 98:
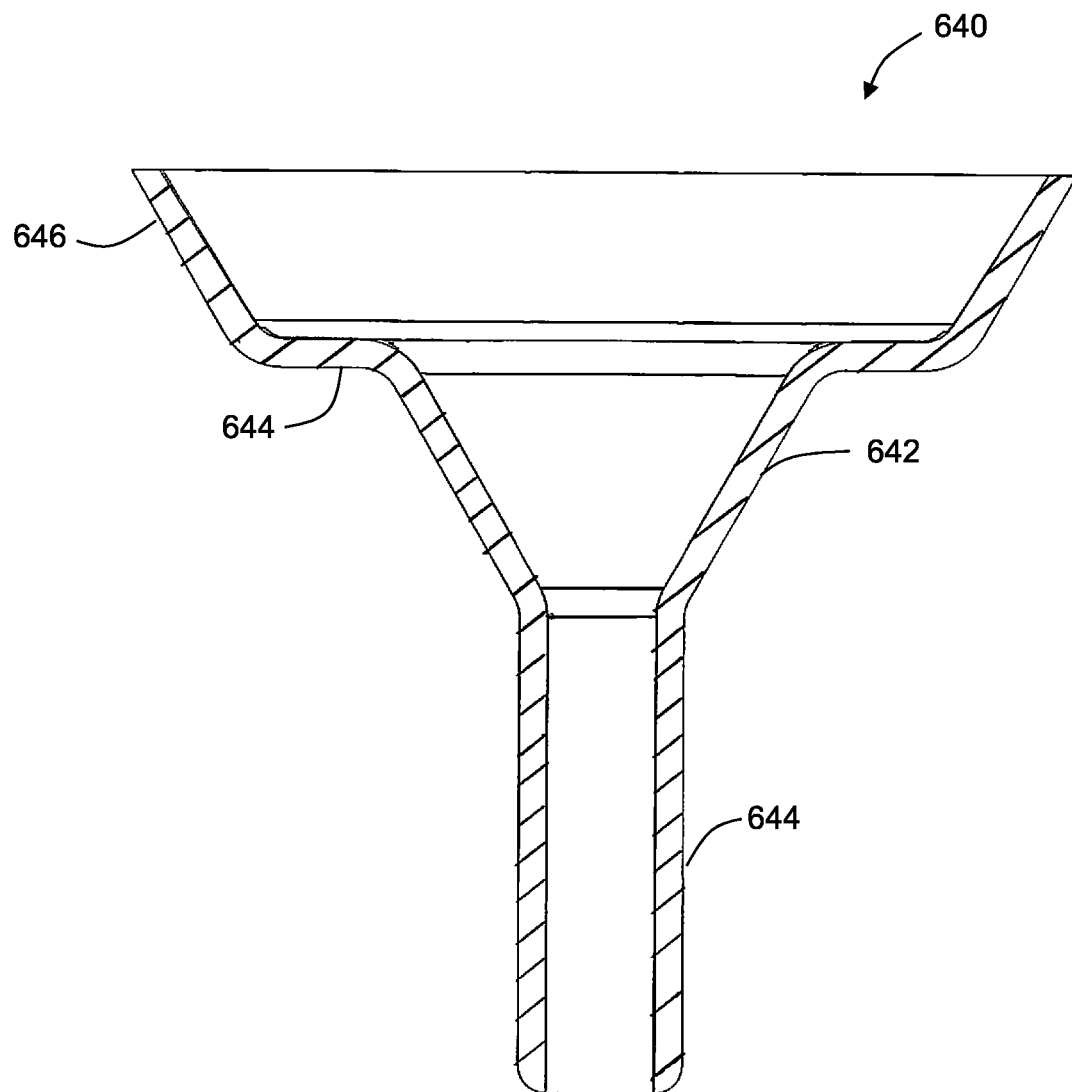
FIG. 98 is a cross-sectional view of a metal wedge 640 in accordance with an embodiment of the present invention.

FIG. 98 is a cross-sectional view of a metal wedge 640 in accordance with an embodiment of the present invention. The wedge 640 is used for securing a flexible catheter to a base. The wedge 640 has an initial flared portion 642 adjacent to a nose portion 644. A flat portion 644 is proximally adjacent to the initial flared portion 642, and a secondary flared portion 646 is proximally adjacent to the flat portion 644. In comparison to some of the previously-discussed wedges, the wedge 640 has a steeper angle to the initial flared portion 642. Generally, during assembly, contact of the introducer needle with the wedge (and thus, dulling of the introducer needle) may occur some percentage of the time due to positional variation of the needle relative to the wedge when passing the introducer needle through the wedge into the final assembled position. A steeper angle, however, such as that of the initial flared portion 642, immediately outside the nose portion 644 can minimize the impact to the introducer needle and help guide it through the wedge 640 and maintain sharpness during assembly.

In each of the herein disclosed embodiments and in other alternative embodiments, the components of the infusion set can be made of injection-molded polypropylene, polyethylene, acrylonitrile butadiene styrene polymers, polyesters such as polyethylene terephthalate or similar materials, and/or bio-based resins such as polylactide, starch-filled polypropylene, or polyhydroxyalkanoates. The catheter can be a separate component or it can be injection-molded as part of the base assembly, either as a single part or as a coinjection-molded part using two resins. Soft shot components can be of ethylene vinyl acetate, thermoplastic urethanes, styrenic thermoplastic elastomers, cellulosic elastomers, copolyester elastomers, or similar materials.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

What is claimed is:

1. A needle guard for guarding a sharp cannula of an infusion device, the needle guard comprising:
    a proximal portion for connecting to a base of the infusion device; and
    a distal portion for user interaction;
    wherein the proximal and distal portions each include at least one axial cutout that divides the needle guard into first and second lateral sides; and
    wherein a fulcrum web is disposed between the proximal and distal axial cutouts to join the first and second lateral sides of the needle guard and provide a fulcrum for relative rotation of the first and second lateral sides of the needle guard.

2. The needle guard according to claim 1, wherein the needle guard is integrally formed as a unitary structure.

3. The needle guard according to claim 1, wherein:
    the proximal portion includes a pair of axial cutouts;
    the distal portion includes a pair of axial cutouts;
    the proximal axial cutouts are substantially aligned with the distal axial cutouts, forming pairs of aligned cutouts; and
    the needle guard further comprises a pair of fulcrum webs respectively disposed between the pairs of aligned cutouts.

4. The needle guard according to claim 1, wherein the distal portion includes a pair of concave sculpted portions for interaction with the user's fingers.

5. The needle guard according to claim 1, wherein the distal portion includes a plurality of support ribs to increase the structural rigidity of the distal portion.

6. The needle guard according to claim 1, wherein the proximal portion includes a pair of opposing, inward-cantilevered gripping portions for connecting with the infusion device.

7. A combination, comprising:
    the needle guard according to claim 6; and
    the base of the infusion set, wherein the base includes distally-extending column from which a cannula protrudes distally; the column having an undercut middle portion, thereby forming a lip at its distal end;
    wherein the gripping portions of the needle guard engage the lip to selectively retain the needle guard on the base.

8. The combination according to claim 7, wherein when connected with the base, a proximal portion of the needle guard contacts a proximal ceiling of an annular space surrounding the column.

9. The combination according to claim 8, wherein the column extends distally beyond a substantially planar distal surface of the base.

10. The combination according to claim 7, wherein:
    the base includes an adhesive on a distal surface thereof; and
    the combination further comprises a one-piece release liner having an interior opening therethrough, an external tab, and a single cut extending substantially radially from the tab to the interior opening.

11. The combination according to claim 10, wherein the interior opening is substantially centered about the column.

12. The combination according to claim 7, wherein:
    the base includes an adhesive on a distal surface thereof; and
    the combination further comprises a one-piece release liner covering the adhesive, the release liner comprising:
        a flexible planar field portion having an interior opening therethrough, the field portion having a first measurement from a center of the field portion to a perimeter of the field portion; and
        a tab portion contiguous with the field portion and extending a second measurement from the center of the field portion to a perimeter of the tab portion, the second measurement being greater than the first measurement, the release liner having a single cut extending substantially linearly from the tab portion to the interior opening.

13. The needle guard according to claim 1, wherein the proximal portion of the needle guard connects directly to a distal portion of the base of the infusion device.

* * * * *